US011591350B2

(12) United States Patent
Anderson et al.

(10) Patent No.: US 11,591,350 B2
(45) Date of Patent: Feb. 28, 2023

(54) MODULATORS OF CYSTIC FIBROSIS TRANSMEMBRANE CONDUCTANCE REGULATOR

(71) Applicant: Vertex Pharmaceuticals Incorporated, Boston, MA (US)

(72) Inventors: Corey Don Anderson, Brighton, MA (US); Jeremy J. Clemens, San Diego, CA (US); Thomas Cleveland, San Marcos, CA (US); Timothy Richard Coon, Carlsbad, CA (US); Bryan Frieman, La Jolla, CA (US); Peter Grootenhuis, Del Mar, CA (US); Sara Sabina Hadida Ruah, La Jolla, CA (US); Jason McCartney, Cardiff by the Sea, CA (US); Mark Thomas Miller, San Diego, CA (US); Prasuna Paraselli, San Diego, CA (US); Fabrice Pierre, La Jolla, CA (US); Sara E. Swift, San Diego, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 122 days.

(21) Appl. No.: 16/992,448

(22) Filed: Aug. 13, 2020

(65) Prior Publication Data

US 2021/0047350 A1 Feb. 18, 2021

Related U.S. Application Data

(60) Provisional application No. 62/886,511, filed on Aug. 14, 2019.

(51) Int. Cl.
*C07F 7/30* (2006.01)
*C07F 7/08* (2006.01)
*A61K 31/404* (2006.01)
*A61K 31/47* (2006.01)
*A61K 45/06* (2006.01)

(52) U.S. Cl.
CPC .......... *C07F 7/0816* (2013.01); *A61K 31/404* (2013.01); *A61K 31/47* (2013.01); *C07F 7/30* (2013.01); *A61K 45/06* (2013.01); *C07B 2200/05* (2013.01)

(58) Field of Classification Search
CPC .................. C07F 7/30; C07F 7/0816
See application file for complete search history.

(56) References Cited

U.S. PATENT DOCUMENTS

| | | | |
|---|---|---|---|
| 2,677,682 A | 5/1954 | Fahrenbach et al. |
| 9,663,508 B2 | 5/2017 | Bregman et al. |
| 9,782,408 B2 | 10/2017 | Miller et al. |
| 9,981,910 B2 | 5/2018 | Altenbach et al. |
| 10,118,916 B2 | 11/2018 | Altenbach et al. |
| 10,131,670 B2 | 11/2018 | Strohbach et al. |
| 10,138,227 B2 | 11/2018 | Altenbach et al. |
| 10,208,053 B2 | 2/2019 | Strohbach et al. |
| 10,258,624 B2 | 4/2019 | Miller et al. |
| 11,066,417 B2 | 7/2021 | Clemens et al. |
| 2011/0098311 A1 | 4/2011 | Van Goor et al. |
| 2013/0317010 A1 | 11/2013 | Chowdhury et al. |
| 2013/0317001 A1 | 11/2013 | Andrez et al. |
| 2014/0073667 A1 | 3/2014 | Morgan et al. |
| 2018/0099932 A1 | 4/2018 | Altenbach et al. |
| 2018/0141954 A1 | 5/2018 | Strohbach et al. |
| 2018/0162839 A1 | 6/2018 | Abela et al. |
| 2018/0170938 A1 | 6/2018 | Strohbach et al. |
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0119253 A1 | 4/2019 | Dhamankar et al. |
| 2019/0153000 A1 | 5/2019 | Munoz et al. |
| 2019/0240197 A1 | 8/2019 | Chu et al. |
| 2019/0248809 A1 | 8/2019 | Clemens et al. |
| 2019/0269683 A1 | 9/2019 | Miller et al. |
| 2022/0041621 A1 | 2/2022 | Clemens et al. |
| 2022/0047564 A1 | 2/2022 | Altshuler et al. |
| 2022/0106331 A1 | 4/2022 | Clemens et al. |
| 2022/0127247 A1 | 4/2022 | Azimioara et al. |

FOREIGN PATENT DOCUMENTS

| | | |
|---|---|---|
| CL | 201902734 | 1/2020 |
| CL | 20200856 | 8/2020 |
| CN | 102227424 A | 10/2011 |
| CN | 106432213 A | 2/2017 |
| EP | 0 846 687 A1 | 6/1998 |
| JP | 2014-526500 A | 10/2014 |
| JP | 6916285 | 11/2020 |
| JP | 2020-541909 | 5/2021 |
| JP | 6896619 | 6/2021 |

(Continued)

OTHER PUBLICATIONS

Alberti, C. and Tironi, C. (1971) "Sulfanilammidi Pirazoliche," *Il Farmaco—Ed. Sc.* 26(1), 66-88.
Bastin, R.J. et al., "Salt selection and optimization procedures for pharmaceutical new chemical entities," *Org. Pro. Res. Dev.* 2000, 4(5), 427-435.
Braker, W. et al. (1947) "Substituted Sulfanilamidopyrimidines," *J. Am. Chem. Society*, 69, 3072-3075.
Chen, L. et al. (2014) "Synthesis and Antimicrobial Activity of the Hybrid Molecules between Sulfonamides and Active Antimicrobial Pleuromutilin Derivative," *Chemical Biology and Drug Design*, 86(2), 239-245.
Cherepakha, A.Y. et al. (2018) "Hetaryl Bromides Bearing the SO2F Group—Versatile Substrates for Palladium-Catalyzed C—C Coupling Reactions", *Eur J Org Chem*, 47: 6682-6692.

(Continued)

*Primary Examiner* — Shawquia Jackson
(74) *Attorney, Agent, or Firm* — Finnegan, Henderson, Farabow, Garrett & Dunner, LLP

(57) ABSTRACT

This disclosure provides modulators of Cystic Fibrosis Transmembrane Conductance Regulator (CFTR), pharmaceutical compositions containing at least one such modulator, methods of treatment of cystic fibrosis using such modulators and pharmaceutical compositions, and processes for making such modulators.

27 Claims, No Drawings

(56) References Cited

FOREIGN PATENT DOCUMENTS

| | | |
|---|---|---|
| JP | 7061115 | 4/2022 |
| TW | I173416 B | 8/2021 |
| WO | WO 2001/090092 A1 | 11/2001 |
| WO | WO 2005/049018 A1 | 6/2005 |
| WO | WO 2005/075435 A1 | 8/2005 |
| WO | WO 2006/002421 A2 | 1/2006 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/117715 A2 | 10/2007 |
| WO | WO 2007/134279 A2 | 11/2007 |
| WO | WO 2008/127399 A2 | 10/2008 |
| WO | WO 2008/154241 A1 | 12/2008 |
| WO | WO 2009/006315 A1 | 1/2009 |
| WO | WO 2009/038683 A2 | 3/2009 |
| WO | WO 2009/073757 A1 | 6/2009 |
| WO | WO 2009/076142 A2 | 6/2009 |
| WO | WO 2009/108657 A2 | 9/2009 |
| WO | WO 2010/019239 A2 | 2/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/108162 A1 | 9/2010 |
| WO | WO 2011/019413 A1 | 2/2011 |
| WO | WO 2011/072241 A1 | 6/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/133751 A2 | 10/2011 |
| WO | WO 2011/133951 A1 | 10/2011 |
| WO | WO 2012/027247 A2 | 3/2012 |
| WO | WO 2012/027731 A2 | 3/2012 |
| WO | WO 2012/170061 A1 | 12/2012 |
| WO | WO 2013/064984 A1 | 5/2013 |
| WO | WO 2013/070961 A1 | 5/2013 |
| WO | WO 2013/112804 A1 | 8/2013 |
| WO | WO 2013/130669 A1 | 9/2013 |
| WO | WO 2013/158121 A1 | 10/2013 |
| WO | WO 2013/160419 A1 | 10/2013 |
| WO | WO 2013/185112 A1 | 12/2013 |
| WO | WO 2014/014841 A1 | 1/2014 |
| WO | WO 2014/071122 A1 | 5/2014 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/160945 A1 | 10/2016 |
| WO | WO 2017/053455 A1 | 3/2017 |
| WO | WO 2013/038386 A1 | 5/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/080591 A1 | 5/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/113089 A1 | 6/2019 |
| WO | WO 2019/113476 A2 | 6/2019 |
| WO | WO 2019/152940 A1 | 8/2019 |
| WO | WO 2019/161078 A1 | 8/2019 |
| WO | WO 2019/191620 A1 | 10/2019 |
| WO | WO 2019/195739 A1 | 10/2019 |
| WO | WO 2019/200246 A1 | 10/2019 |
| WO | WO 2020/102346 A1 | 5/2020 |
| WO | WO 2020/128925 A1 | 6/2020 |
| WO | WO 2020/191227 A1 | 9/2020 |
| WO | WO 2020/206080 A1 | 10/2020 |
| WO | WO 2020/214921 A1 | 10/2020 |
| WO | WO 2020/242935 A1 | 12/2020 |
| WO | WO 2021/030552 A1 | 2/2021 |
| WO | WO 2021/030554 A1 | 2/2021 |
| WO | WO 2021/030555 A1 | 2/2021 |
| WO | WO 2021/030556 A1 | 2/2021 |
| WO | WO 2021/097054 A1 | 5/2021 |
| WO | WO 2021/097057 A1 | 5/2021 |
| WO | WO 2022/032068 A1 | 2/2022 |
| WO | WO 2022/036060 A1 | 2/2022 |

OTHER PUBLICATIONS

Chio, L. et al. (1996) "Identification of a Class of Sulfonamides Highly Active Against Dihydropteroate Synthase from Toxoplasma Gondii, Pneumocystis Carinii, and *Mycobacterium avium*," Antimicrobial Agents and Chemotherapy, American Society for Microbiology, 40(3), 727-733.

Donaldson, S.H. et al. (2017) "Tezacaftor/Ivacaftor in Subjects with Cystic Fibrosis and F508del/F508del-CFTR or F508del/G551D-CFTR", *Am. J. Respir. Crit. Care Med.*, 197(2): 214-224.

Gage, J. C. et al. (1947), "2-P-Aminobenzenesulphonamido-4 : 6-Dimethoxypyrimidine: Experimental Evaluation," British Journal of Pharmacology and Chemotherapy, 2(3), 149-162.

Ghorab, Mostafa at al. (2017) "Aromatase inhibitors and apoptotic inducers: Design, synthesis, anticancer activity and molecular modeling studies of novel phenothiazine derivatives carrying sulfonamide moiety as hybrid molecules," *Eur. J. Med. Chem.*, 134, 304-315.

Gomes, Paula et al. (2003) "Amino acids as selective sulfonamide acylating agents," Tetrahedron, 59(38), 7473-7480.

Hassan, H. H. A. M. and Soliman, R. (2000) "Synthesis and GC-EIMS Analyses of Optically Pure 3-Hydroxy-2-azetidinones Having N-sulfonamide Drugs Side Chain," *Synthetic Communications*, 30(14), 2465-2478.

International Patent Application No. PCT/US2019/018042: International Search Report and Written Opinion, dated Apr. 17, 2019 (10 pages).

International Patent Application No. PCT/US2019/061171: International Search Report and Written Opinion, dated Feb. 12, 2020 (14 pages).

International Patent Application No. PCT/U2020/026331: International Search Report and Written Opinion, dated May 29, 2020 (14 pages).

International Patent Application No. PCT/US2021/053853: International Search Report and Written Opinion, dated Dec. 21, 2021 (12 pages).

International Patent Application No. PCT/US2021/053855: International Search Report and Written Opinion, dated Jan. 3, 2022 (12 pages).

International Patent Application No. PCT/US2021/053856: International Search Report and Written Opinion, dated Dec. 22, 2021 (12 pages).

International Patent Application No. PCT/US2021/053858: International Search Report and Written Opinion, dated Mar. 17, 2022 (14 pages).

International Patent Application No. PCT/US2021/053860: International Search Report and Written Opinion, dated Dec. 23, 2021 (12 pages).

International Patent Application No. PCT/US2021/053861: International Search Report and Written Opinion, dated Dec. 22, 2021 (12 pages).

(56) References Cited

OTHER PUBLICATIONS

International Patent Application No. PCT/US2021/053862: International Search Report and Written Opinion, dated Dec. 22, 2021 (12 pages).
International Patent Application No. PCT/US2021/053863: International Search Report and Written Opinion, dated Feb. 4, 2022 (16 pages).
International Patent Application No. PCT/US2021/053864: International Search Report and Written Opinion, dated Mar. 15, 2022 (17 pages).
International Patent Application No. PCT/US2021/053865: International Search Report and Written Opinion, dated Jan. 26, 2022 (16 pages).
International Patent Application No. PCT/US2021/062687: International Search Report and Written Opinion, dated Apr. 4, 2022 (14 pages).
Kim, T. et al. (2018) "Sulfonamidation of Aryl and Heteroaryl Halides through Photosensitized Nickel Catalysis," *Agewandte Chemie*, 57, 3488-3492.
Newkome, G.R. et al. (1979) "Nicotinic Acid Crown Ethers. Synthesis, Reactions, and Complexation of Nicotinonitrile Macrocycles", *J Org Chem*, 44(15): 2639-2697.
Nishida, H. et al. (2017) "Exploration of pyrrole derivatives to find an effective potassium competitive acid blocker with moderately long-lasting suppression of gastric acid secretion", *Bioorg Med Chem*, 25(13): 3447-3460.
"A phase 1/2 study of VX-121 in healthy subjects and in subjects with cystic fibrosis", EU Clinical Trials Register, May 3, 2019 (May 3, 2019), XP055903414, Retrieved from the Internet: URL:https://www.clinicaltrialsregister.eu/ctr-search/trial/2018-000126-55/NL [retrieved on Mar. 21, 2022].
"A Phase 2 Study to Evaluate Efficacy and Safety of VX-561 in Subjects Aged 18 Years and Older With Cystic Fibrosis", ClinicatTials. gov, Apr. 11, 2019 (Apr. 11, 2019), XP055903562, Retrieved from the Internet: URL:https://clinicaltrials.gov/ct2/show/NCT03911713 [retrieved on Mar. 21, 2022].
Prashantha, G. et al. (2017) "Selective IKur Inhibitors for the Potential Treatment of Atrial Fibrillation: Optimization of the Phenyl Quinazoline Series Leading to Clinical Candidate 5-[5-Phenyl-4-(pyridin-2-ylmethylamino)quinazolin-2-yl]pyridine-3-sulfonamide", *J Med Chem*, 60(9): 3795-3803.
Rewcastle, G.W. et al. (1996) "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor", *J Med Chem*, 39(9): 1823-1835.
Raiziss, GW et al. (1942) "N1-Sulfanilylaminoalkylpyrimidines," *J. Am. Chem. Soc.* 64, 2340-2342.
Rose, F. L. et al. (1946) "P-Aminobenzenesulphonamide Derivatives of Pyrimidines as Antibacterial Agents," *J. Am. Chem. Soc.*, 81-85.
Sprague, JM et al. (1941) "Sulfonamido derivatives of thiazoles," *J. Am. Chem. Soc.* 63, 578-580.
Sprague, JM et al. (1941) "Sulfonamido derivatives of pyrimidines," *J. Am. Chem. Soc.* 63, 3028-3030.
"A Study to Evaluate the Safety and Efficacy of VX-121 Combination Therapy in Subjects with Cystic Fibrosis", ClinicalTrials. gov, Apr. 30, 2019 (Apr. 30, 2019), XP55903330, Retrieved from the Internet: URL:https://clinicaltrials.gov/ct2/show/NCT03912233 [retrieved on Mar. 21, 2022].
Sugasawa, S et al. (1949) "Reaction between sulfaguanidine and 1,3-keto aldehydes. I. Synthesis of 2-sulfanilamido-4-methylpyrimidine," 69, 82-85.
"Symdeko in Cystic Fibrosis Patients", ClinicalTrials.gov, Jul. 23, 2018 (Apr. 23, 2018), XP055661778, Retrieved from the Internet: URL:https://clinicaltrials.gov/ct2/show/record/NCT03506061 [retrieved on Jan. 24, 2020].
Tani, C et al. (1950) "Syntheses of sulfanilamide derivatives containing diphenylene oxide," *Journal of the Pharmaceutical Society of Japan*, 70, 126-127.
U.S. Appl. No. 17/600,829, filed Oct. 1, 2021, by Abela et al.
U.S. Appl. No. 16/992,419, filed Aug. 13, 2021, by Angell et al.
U.S. Appl. No. 16/992,441, filed Aug. 13, 2021, by Shi et al.
U.S. Appl. No. 16/992,448, filed Aug. 13, 2021, by Anderson et al.
U.S. Appl. No. 16/992,675, filed Aug. 13, 2021, by Abela et al.
U.S. Appl. No. 17/546,649, filed Dec. 9, 2021, by Borek et al.

MODULATORS OF CYSTIC FIBROSIS TRANSMEMBRANE CONDUCTANCE REGULATOR

This application claims priority from U.S. Provisional Application No. 62/886,511, filed Aug. 14, 2019, which is hereby incorporated by reference in its entirety.

This disclosure provides modulators of Cystic Fibrosis Transmembrane Conductance Regulator (CFTR), pharmaceutical compositions containing the modulators, methods of treatment of cystic fibrosis using such modulators and pharmaceutical compositions, and processes for making such modulators.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to increased mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence, and is commonly referred to as the F508del mutation. This mutation occurs in most of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease-causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$—$K^+$-ATPase pump and Cl— channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

A number of CFTR modulating compounds have recently been identified. However, compounds that can treat or reduce the severity of the cystic fibrosis and other CFTR mediated diseases, and particularly the more severe forms of these diseases, are still needed.

One aspect of the invention provides novel compounds, including compounds of Formulae (1), (2), (3), and (4), pharmaceutically acceptable salts thereof, and deuterated derivatives of any of the foregoing wherein the compounds each contain at least one silicon atom or at least one germanium atom.

For example, disclosed herein are compounds of Formula (1) and pharmaceutically acceptable salts and deuterated derivatives thereof:

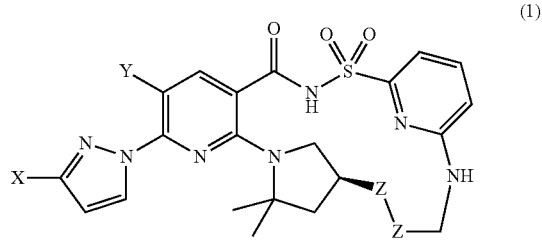

(1)

wherein:
X is selected from $Si(R)_3$, —$(O)_n$—$(C_1$-$C_8$ alkyl), —$(O)_n$—$(C_3$-$C_{10}$ cycloalkyl), wherein:
  n is 0 or 1,
  each $C_1$-$C_8$ alkyl is substituted with 0, 1, 2, or 3 groups selected from halogen, hydroxy, oxo, $C_3$-$C_{10}$ cycloalkyl, $C_1$-$C_4$ haloalkyl, and $Si(R)_3$ groups,
  each $C_3$-$C_{10}$ cycloalkyl is substituted with 0, 1, 2, 3, or 4 groups selected from halogen, $C_1$-$C_4$ haloalkyl, $C_1$-$C_4$ alkyl, and $Si(R)_3$ groups, and
  one —$CH_2$— in each $C_1$-$C_8$ alkyl is optionally replaced with —$Si(R)_2$—;
Y is selected from hydrogen and —$Si(R)_3$;
each Z is independently selected from —$CH_2$— and —$Si(R)_2$—; and each R is independently selected from phenyl and $C_1$-$C_6$ alkyl groups; and wherein each compound of Formula (1) contains at least one Si atom. In some embodiments, the compound of Formula (1) is selected from Compounds (1-1)-(1-11) and pharmaceutically acceptable salts and deuterated derivatives thereof.

In some embodiments, X in Formula (1) is selected from $Si(R)_3$,

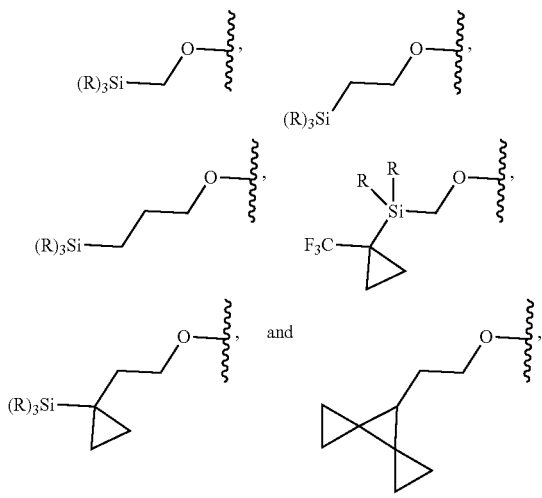

wherein
each R is independently selected from phenyl and $C_1$-$C_6$ alkyl groups.

Another embodiment provides compounds of Formula (2) and pharmaceutically acceptable salts and deuterated derivatives thereof:

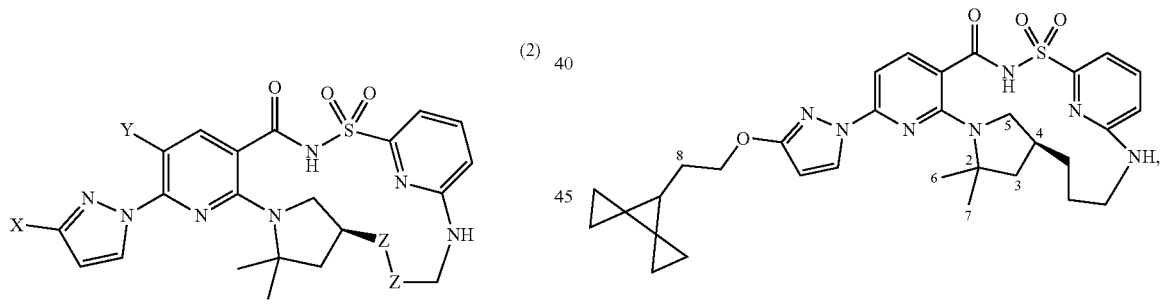

wherein:
X is selected from $Ge(R)_3$, —(O)$_n$—($C_1$-$C_8$ alkyl), —(O)$_n$—($C_3$-$C_{10}$ cycloalkyl), wherein:
  n is 0 or 1,
  each $C_1$-$C_8$ alkyl is substituted with 0, 1, 2, or 3 groups selected from halogen, hydroxy, oxo, $C_3$-$C_{10}$ cycloalkyl, $C_1$-$C_4$ haloalkyl, and $Ge(R)_3$ groups,
  each $C_3$-$C_{10}$ cycloalkyl is substituted with 0, 1, 2, 3, or 4 groups selected from halogen, $C_1$-$C_4$ haloalkyl, $C_1$-$C_4$ alkyl, and $Ge(R)_3$ groups, and
  one —$CH_2$— in each $C_1$-$C_8$ alkyl is optionally replaced with —$Ge(R)_2$—;
Y is selected from hydrogen and —$Ge(R)_3$;
each Z is independently selected from —$CH_2$— and —$Ge(R)_2$—; and
each R is independently selected from phenyl and $C_1$-$C_6$ alkyl groups; and wherein each compound of Formula (2) contains at least one Ge atom. In some embodiments, the compound of Formula (2) is selected from Compound (2-1) and pharmaceutically acceptable salts and deuterated derivatives thereof.

In some embodiments, X in Formula (2) is selected from $Ge(R)_3$,

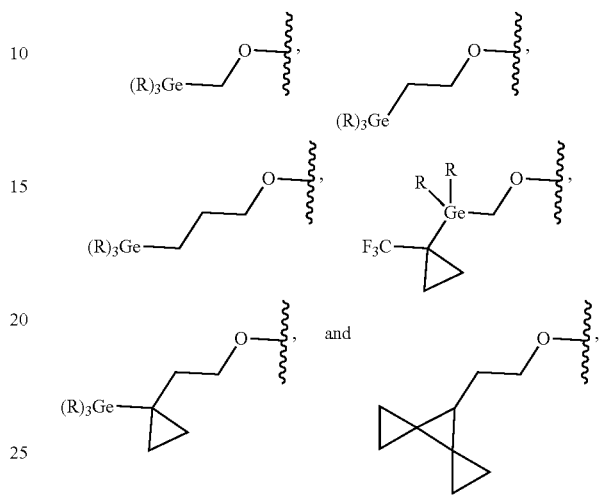

wherein
each R is independently selected from phenyl and $C_1$-$C_6$ alkyl groups.

A further embodiment of the invention includes compounds of Formula (3) and pharmaceutically acceptable salts and deuterated derivatives thereof:

(3)

pharmaceutically acceptable salts thereof, and deuterated derivatives of any of the foregoing,
wherein:
  the carbon atom at position 2 of Formula (3) is replaced by a silicon atom;
  at least one of the methyl groups at positions 6 and 7 of Formula (3) is replaced by a group chosen from —Si(R)$_3$ groups, —Si(R)$_2$(OR) groups, and —Si(R)(OR)$_2$ groups;
  at least one of the methylene groups at positions 3, 5, and 8 of Formula (3) is replaced by a group chosen from >Si(R)$_2$ groups and >Si(R)(OR) groups; and/or
  the methine group at position 4 of Formula (3) is replaced by a group chosen from ≡Si(R) groups and ≡Si(OR) groups; and
wherein each R, which may be identical or different, is independently chosen from hydrogen, phenyl, and $C_1$-$C_6$ alkyl groups.

A further embodiment of the invention includes compounds of Formula (4) and pharmaceutically acceptable salts and deuterated derivatives thereof:

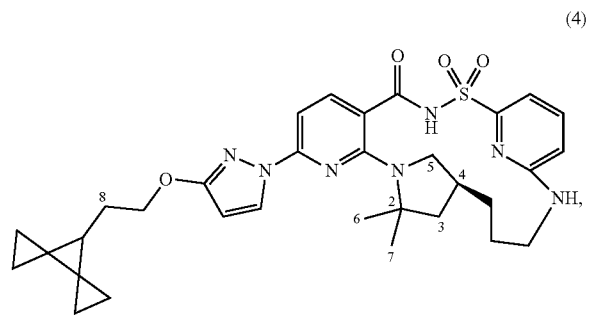 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

(4)

pharmaceutically acceptable salts thereof, and deuterated derivatives of any of the foregoing,
wherein:
the carbon atom at position 2 of Formula (4) is replaced by a germanium atom;
at least one of the methyl groups at positions 6 and 7 of Formula (4) is replaced by a group chosen from —Ge(R)$_3$ groups, —Ge(R)$_2$(OR) groups, and —Ge(R)(OR)$_2$ groups;
at least one of the methylene groups at positions 3, 5, and 8 of Formula (4) is replaced by a group chosen from >Ge(R)$_2$ groups and >Ge(R)(OR) groups; and/or
the methine group at position 4 of Formula (4) is replaced by a group chosen from ≡Ge(R) groups and ≡Ge(OR) groups; and wherein each R, which may be identical or different, is independently chosen from hydrogen, phenyl, and C$_1$-C$_6$ alkyl groups.

Another aspect of the invention provides pharmaceutical compositions comprising at least one compound chosen from the novel compounds disclosed herein, pharmaceutically acceptable salts thereof, and deuterated derivatives of any of the foregoing, and at least one pharmaceutically acceptable carrier, which compositions may further include at least one additional active pharmaceutical ingredient. Thus, another aspect of the invention provides methods of treating the CFTR-mediated disease cystic fibrosis comprising administering at least one of compound chosen from the novel compounds disclosed herein, pharmaceutically acceptable salts thereof, and deuterated derivatives of any of the foregoing, and at least one pharmaceutically acceptable carrier, optionally as part of a pharmaceutical composition comprising at least one additional component, to a subject in need thereof.

In certain embodiments, the pharmaceutical compositions of the invention comprise at least one compound chosen from Formulae (1), (2), (3), and (4), Compounds (1-1)-(1-11) (i.e., Compounds (1-1), (1-2), (1-3), (1-4), (1-5), (1-6), (1-7), (1-8), (1-9), (1-10), and (1-11)), Compound (2-1), and pharmaceutically acceptable salts and deuterated derivatives thereof. In some embodiments, compositions comprising at least one compound chosen from the Formulae (1), (2), (3), and (4), Compounds (1-1)-(1-11), Compound (2-1), and pharmaceutically acceptable salts and deuterated derivatives thereof may optionally further comprise (a) at least one compound chosen from Compound II and pharmaceutically acceptable salts and deuterated derivatives thereof; (b) at least one compound chosen from Compound III and pharmaceutically acceptable salts and deuterated derivatives thereof, such as Compound III-d; and/or (c) at least one compound chosen from Compound IV and pharmaceutically acceptable salts and deuterated derivatives thereof.

Another aspect of the invention provides methods of treating the CFTR-mediated disease cystic fibrosis comprising administering at least one compound chosen from the novel compounds disclosed herein, pharmaceutically acceptable salts thereof, and deuterated derivatives of any of the foregoing, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II), N-[2,4-bis(1,1-dimethylethyl)-5-hydroxyphenyl]-1,4-dihydro-4-oxoquinoline-3-carboxamide (Compound III) or N-(2-(tert-butyl)-5-hydroxy-4-(2-(methyl-d3)propan-2-yl-1,1,1,3,3,3-d6) phenyl)-4-oxo-1,4-dihydroquinoline-3-carboxamide (Compound III-d), and 3-(6-(1-(2,2-difluorobenzo[d][1,3]dioxol-5-yl)cyclopropane carboxamido)-3-methylpyridin-2-yl)benzoic acid (Compound IV), optionally as part of at least one pharmaceutical composition comprising at least one additional component, to a patient in need thereof. In some embodiments, Compound II and/or Compound III are in the form of a solid dispersion.

Definitions

"Compound II" as used herein, refers to (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, which can be depicted with the following structure:

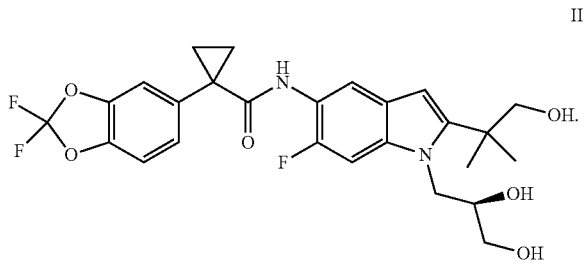 [SMILES: CC(C)(CO)c1cc2cc(NC(=O)C3(c4ccc5c(c4)OC(F)(F)O5)CC3)c(F)cc2n1C[C@@H](O)CO]

II

Compound II may be in the form of a pharmaceutically acceptable salt. Compound II and methods of making and using Compound II are disclosed in WO 2010/053471, WO 2011/119984, and WO 2015/160787, each incorporated hereing by reference.

"Compound III" as used throughout this disclosure refers to N-(5-hydroxy-2,4-di-tert-butyl-phenyl)-4-oxo-1H-quinoline-3-carboxamide which is depicted by the structure:

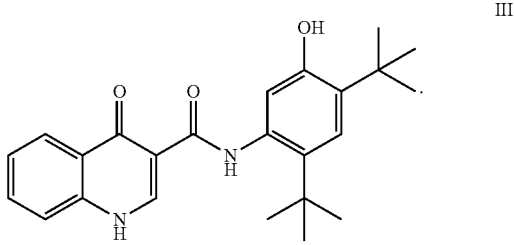 [SMILES: CC(C)(C)c1cc(C(C)(C)C)c(NC(=O)c2c[nH]c3ccccc3c2=O)cc1O]

III

Compound III may also be in the form of a pharmaceutically acceptable salt. Compound III and methods of making and using Compound III are disclosed in WO 2006/002421, WO 2007/079139, and WO 2010/019239, each incorporated herein by reference.

In some embodiments, a deuterated derivative of Compound III (Compound III-d) is employed in the compositions and methods disclosed herein. A chemical name for Compound III-d is N-(2-(tert-butyl)-5-hydroxy-4-(2-(methyl-d3) propan-2-yl-1,1,1,3,3,3-d6)phenyl)-4-oxo-1,4-dihydroquinoline-3-carboxamide, as depicted by the structure:

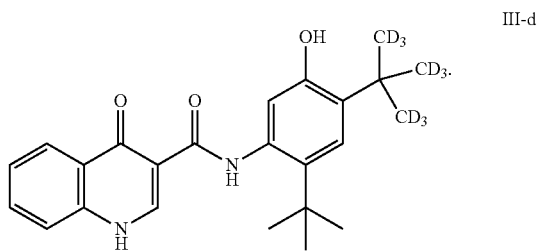 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

Compound III-d may be in the form of a pharmaceutically acceptable salt. Compound III-d and methods of making and using Compound III-d are disclosed in WO 2012/158885 and WO 2014/078842, incorporated herein by reference.

"Compound IV" as used herein, refers to 3-(6-(1-(2,2-difluorobenzol[d][1,3]dioxol-5-yl)cyclopropanecarboxamido)-3-methylpyridin-2-yl)benzoic acid, which is depicted by the chemical structure:

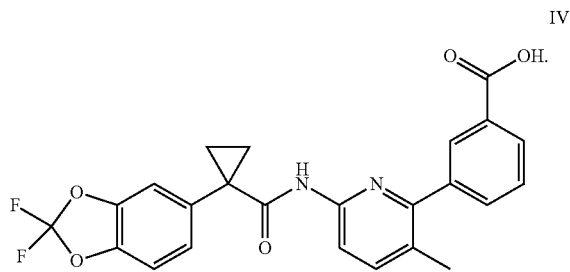 [SMILES: Cc1ccc(NC(=O)C2(c3ccc4c(c3)OC(F)(F)O4)CC2)nc1-c1cccc(C(=O)O)c1]

Compound IV may be in the form of a pharmaceutically acceptable salt. Compound IV and methods of making and using Compound IV are disclosed in WO 2007/056341, WO 2009/073757, and WO 2009/076142, incorporated herein by reference.

As used herein, "—Si(R)$_3$ groups", "—Si(R)$_2$(OR) groups", and "—Si(R)(OR)$_2$ groups" refer to monovalent groups having three substituents, wherein the "-" symbols represent the point of attachment from the silicon atom to the compound.

As used herein, ">Si(R)$_2$ groups" and ">Si(R)(OR) groups" refer to divalent groups having two substituents, wherein the ">" symbols represent the two points of attachment from the silicon atom to the compound.

As used herein, "≡Si(R) groups" and "—Si(OR) groups" refer to trivalent groups having one substituent and the "-" symbols represent the three points of attachment from the silicon atom to the compound.

As used herein, "—Ge(R)$_3$ groups", "—Ge(R)$_2$(OR) groups", and "—Ge(R)(OR)$_2$ groups" refer to monovalent groups having three substituents, wherein the "-" symbols represent the point of attachment from the silicon atom to the compound.

As used herein, ">Ge(R)$_2$ groups" and ">Ge(R)(OR) groups" refer to divalent groups having two substituents, wherein the ">" symbols represent the two points of attachment from the silicon atom to the compound.

As used herein, "≡Ge(R) groups" and "≡Ge(OR) groups" refer to trivalent groups having one substituent and the "≡" symbols represent the three points of attachment from the silicon atom to the compound.

As used herein, "Compounds (1-1)-(1-11)" refers to each of Compounds (1-1), (1-2), (1-3), (1-4), (1-5), (1-6), (1-7), (1-8), (1-9), (1-10), and (1-11).

As used herein, the term "alkyl" refers to a saturated, branched or unbranched aliphatic hydrocarbon containing carbon atoms (such as, for example, 1, 2, 3, 4, 5, 6, 7, 8, 9, 10, 11, 12, 13, 14, 15, 16, 17, 18, 19, or 20 carbon atoms). Alkyl groups may be substituted or unsubstituted.

As used herein, the term "haloalkyl group" refers to an alkyl group substituted with one or more halogen atoms.

The term "alkoxy" as used herein refers to an alkyl or cycloalkyl covalently bonded to an oxygen atom. Alkoxy groups may be substituted or unsubstituted.

As used herein, "cycloalkyl" refers to a cyclic, bicyclic, tricyclic, or polycyclic non-aromatic hydrocarbon groups having 3 to 12 carbons (such as, for example 3-10 carbons). "Cycloalkyl" groups encompass monocyclic, bicyclic, tricyclic, bridged, fused, and spiro rings, including mono spiro and dispiro rings. Non-limiting examples of cycloalkyl groups are cyclopropyl, cyclobutyl, cyclopentyl, cyclohexyl, adamantyl, norbornyl, and dispiro[2.0.2.1]heptane. Cycloalkyl groups may be substituted or unsubstituted.

"Substituted," indicates that at least one hydrogen of the "substituted" group is replaced by a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position. Suitable substituent groups are groups that do not eliminate the CFTR modulating activity of the unsubstituted compound.

As used herein, "deuterated derivative(s)" means the same chemical structure, but with one or more hydrogen atoms replaced by a deuterium atom.

As used herein, "CFTR" means cystic fibrosis transmembrane conductance regulator.

As used herein, the term "CFTR modulator" refers to a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. The novel compounds disclosed herein are CFTR correctors.

As used herein, the term "CFTR potentiator" refers to a compound that increases the channel activity of CFTR protein located at the cell surface, resulting in enhanced ion transport. Compound III and III-d disclosed herein are examples of CFTR potentiators. It will be appreciated that when a description of a combination of compound selected from compounds of Formulae (1), (2), (3), and (4), Compounds (1-1)-(1-11), Compound (2-1), and pharmaceutically acceptable salts and deuterated derivatives thereof, and other specified CFTR modulating agents is provided herein, reference to "Compound III or III-d" in connection with the combination means that either Compound III or Compound III-d, but not both, is included in the combination.

As used herein, the term "active pharmaceutical ingredient" or "therapeutic agent" ("API") refers to a biologically active compound.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. The terms "about" and "approximately" may refer to an acceptable error for a particular value as determined by one of skill in the art, which depends in part on how the values is measured or determined. In some embodiments, the terms "about" and "approximately" mean within 20%, 15%, 10%, 5%, 4%, 3%, 2%, 1%, or 0.5% of a given value or range.

As used herein, the term "solvent" refers to any liquid in which the product is at least partially soluble (solubility of product >1 g/l).

As used herein, the term "room temperature" or "ambient temperature" means 15° C. to 30° C.

It will be appreciated that certain compounds of this invention may exist as separate stereoisomers or enantiomers and/or mixtures of those stereoisomers or enantiomers.

Certain compounds disclosed herein may exist as tautomers and both tautomeric forms are intended, even though only a single tautomeric structure is depicted. For example, a description of Compound A is understood to include its tautomer Compound B and vice versa, as well as mixtures thereof

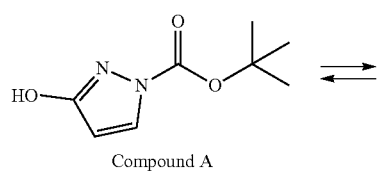

Compound A

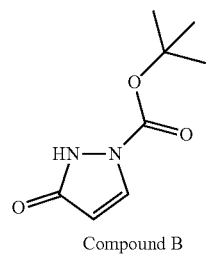

Compound B

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. A "free base" form of a compound, for example, does not contain an ionically bonded salt.

The phrase "and pharmaceutically acceptable salts and deuterated derivatives thereof" is used interchangeably with "and pharmaceutically acceptable salts thereof and deuterated derivatives of any of the forgoing" in reference to one or more compounds or formulae of the invention. These phrases are intended to encompass pharmaceutically acceptable salts of any one of the referenced compounds, deuterated derivatives of any one of the referenced compounds, and pharmaceutically acceptable salts of those deuterated derivatives.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form.

Suitable pharmaceutically acceptable salts are, for example, those disclosed in S. M. Berge, et al. *J. Pharmaceutical Sciences,* 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |

TABLE 1-continued

| | | |
|---|---|---|
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+$ $(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

Methods of Treatment

Any of the novel compounds disclosed herein, such as for example, compounds of Formulae (1), (2), (3), and (4), Compounds (1-1)-(1-11), Compound (2-1), pharmaceutically acceptable salts thereof, and deuterated derivatives of such compounds and salts can act as a CFTR modulator, i.e., it modulates CFTR activity in the body. Individuals suffering from a mutation in the gene encoding CFTR may benefit from receiving a CFTR modulator. A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes. Certain mutations in the CFTR gene result in cystic fibrosis.

Thus, in some embodiments, the invention provides methods of treating, lessening the severity of, or symptomatically treating cystic fibrosis in a patient comprising administering to the patient an effective amount of any of the novel compounds disclosed herein, such as for example, compounds of Formulae (1), (2), (3), and (4), Compounds (1-1)-(1-11), Compound (2-1), pharmaceutically acceptable salts thereof, and/or deuterated derivatives of such compounds and salts, alone or in combination with another active ingredient, such as another CFTR modulating agent. In some embodiments, the patient has an F508del/minimal function (MF) genotype, F508del/F508del genotype (homozygous for the F508del mutation), F508del/gating genotype, or F508del/residual function (RF) genotype. In some embodiments the patient is heterozygous and has one F508del mutation. In some embodiments, the patient is homozygous for the N1303K mutation.

In some embodiments, the patient is heterozygous and has an F508del mutation on one allele and a mutation on the other allele selected from Table 2:

TABLE 2

CFTR Mutations

| Mutation | | | | |
|---|---|---|---|---|
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |
| E193X | W496X | R764X | W1098X | Q1382X |
| W216X | C524X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 296 + 1G→T | 1248 + 1G→A | 1811 + 1G→C | 3040G→C | 3600 + 2insT |

TABLE 2-continued

CFTR Mutations

Mutation

| | | | | |
|---|---|---|---|---|
| 405 + 1G→A | 1249 − 1G→A | 1811 + 1.6kbA→G | (G970R) | 3850 − 1G→A |
| 405 + 3A→C | 1341 + 1G→A | 1811 + 1643G→T | 3120G→A | 4005 + 1G→A |
| 406 − 1G→A | 1525 − 2A→G | 1812 − 1G→A | 3120 + 1G→A | 4374 + 1G→T |
| 621 + 1G→T | 1525 − 1G→A | 1898 + 1G→A | 3121 − 2A→G | |
| 711 + 1G→T | | 1898 + 1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |
| 365-366insT | 1154insTC | 1833delT | 2896insAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→ G | 3007delG | 4016insT |
| 457TAT→ G | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |
| 849delG | 1548delG | 2585delT | 3349insT | 4326delTC |
| 935delA | 1609delCA | 2594delGT | 3659delC | |
| CFTRdele1 | | CFTRdele16-17b | 1461ins4 | |
| CFTRdele2 | | CFTRdele17a,17b | 1924del7 | |
| CFTRdele2,3 | | CFTRdele17a-18 | 2055del9→A | |
| CFTRdele2-4 | | CFTRdele19 | 2105-2117del13insAGAAA | |
| CFTRdele3-10,14b-16 | | CFTRdele19-21 | 2372del8 | |
| CFTRdele4-7 | | CFTRdele21 | 2721del11 | |
| CFTRdele4-11 | | CFTRdele22-24 | 2991del32 | |
| CFTR50kbdel | | CFTRdele22,23 | 3667ins4 | |
| CFTRdup6b-10 | | 124del23bp | 4010del4 | |
| CFTRdele11 | | 602del14 | 4209TGTT→AA | |
| CFTRdele13,14a | | 852del22 | | |
| CFTRdele14b-17b | | 991del5 | | |
| A46D | V520F | Y569D | N1303K | |
| G85E | A559T | L1065P | | |
| R347P | R560T | R1066C | | |
| L467P | R560S | L1077P | | |
| I507del | A561E | M1101K | | |

In some embodiments, the disclosure also is directed to methods of treatment using isotope-labelled compounds of the afore-mentioned compounds, or pharmaceutically acceptable salts thereof, wherein the formula and variables of such compounds and salts are each and independently as described above or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^{2}H$, $^{3}H$, $^{13}C$, $^{14}C$, $^{15}N$ $^{18}O$, $^{17}O$, $^{31}P$, $^{32}P$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^{3}H$)— and/or carbon-14 ($^{14}C$)-labelled compounds are particularly useful for various types of assays, such as substrate tissue distribution assays, due to relatively simple preparation and excellent detectability. For example, deuterium ($^{2}H$)-labelled ones are therapeutically useful with potential therapeutic advantages over the non-$^{2}H$-labelled compounds. In general, deuterium ($^{2}H$)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^{2}H$)-labelled ones. In some specific embodiments, the isotope-labelled compounds and salts are deuterium ($^{2}H$)-labelled, wherein one or more hydrogen atoms therein have been replaced by deuterium. In chemical structures, deuterium is represented as "D."

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

The deuterium ($^{2}H$)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. For a further discussion, see S. L. Harbeson and R. D. Tung, *Deuterium In Drug Discovery and Development*, Ann. Rep. Med. Chem. 2011, 46, 403-417, which is incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Combination Therapies

One aspect disclosed herein provides methods of treating cystic fibrosis and other CFTR mediated diseases using any of the novel compounds disclosed herein, such as for example, compounds of Formulae (1), (2), (3), and (4), Compounds (1-1)-(1-11), Compound (2-1), pharmaceutically acceptable salts thereof, and deuterated derivatives of such compounds and salts in combination with at least one additional active pharmaceutical ingredient, including CFTR modulating agents. In some embodiments, the at least one additional active pharmaceutical ingredient is chosen from (a) Compound II and pharmaceutically acceptable salts thereof, and (b) Compound III or Compound III-d and pharmaceutically acceptable salts of Compound III or Compound III-d. Thus, in some embodiments, the combination therapies provided herein comprise a compound selected from compounds of Formulae (1), (2), (3), and (4), Compounds (1-1)-(1-11), Compound (2-1), and pharmaceutically acceptable salts and deuterated derivatives thereof and at least one compound chosen from Compound II, (Compound III or III-d), and pharmaceutically acceptable salts thereof. In some embodiments, the combination therapies provided herein comprise at least one compound chosen from compounds of Formulae (1), (2), (3), and (4), Compounds (1-1)-(1-11), Compound (2-1), and pharmaceutically acceptable salts and deuterated derivatives thereof, and at least one compound chosen from (Compound III or III-d), Compound IV, and/or pharmaceutically acceptable salts thereof.

In some embodiments, at least one compound chosen from compounds of Formulae (1), (2), (3), and (4), Compounds (1-1)-(1-11), Compound (2-1), and pharmaceutically acceptable salts and deuterated derivatives thereof is administered in combination with at least one compound chosen from Compound II and pharmaceutically acceptable salts thereof. In some embodiments, at least one compound chosen from compounds of Formulae (1), (2), (3), and (4), Compounds (1-1)-(1-11), Compound (2-1), and pharmaceutically acceptable salts and deuterated derivatives thereof is administered in combination with at least one compound chosen from Compound III and pharmaceutically acceptable salts thereof. In some embodiments, at least one compound chosen from compounds of Formulae (1), (2), (3), and (4), Compounds (1-1)-(1-11), Compound (2-1), and pharmaceutically acceptable salts and deuterated derivatives thereof is administered in combination with at least one compound chosen from Compound III-d and pharmaceutically acceptable salts thereof. In some embodiments, at least one compound chosen from compounds of Formulae (1), (2), (3), and (4), Compounds (1-1)-(1-11), Compound (2-1), and pharmaceutically acceptable salts and deuterated derivatives thereof is administered in combination with Compound II or a pharmaceutically acceptable salt thereof and at least one compound chosen from Compound III and pharmaceutically acceptable salts thereof. In some embodiments, at least one compound chosen from compounds of Formulae (1), (2), (3), and (4), Compounds (1-1)-(1-11), Compound (2-1), and pharmaceutically acceptable salts and deuterated derivatives thereof is administered in combination with at least one compound chosen from Compound II and pharmaceutically acceptable salts thereof and at least one compound chosen from Compound III-d and pharmaceutically acceptable salts thereof.

Each of the compounds of Formulae (1), (2), (3), and (4), Compounds (1-1)-(1-11), Compound (2-1), Compound II, and Compound III or III-d, and their pharmaceutically acceptable salts and deuterated derivatives thereof, independently can be administered once daily, twice daily, or three times daily. In some embodiments, at least one compound chosen from compounds of Formulae (1), (2), (3), and (4), Compounds (1-1)-(1-11), Compound (2-1), and pharmaceutically acceptable salts and deuterated derivatives thereof is administered once daily. In some embodiments, at least one compound chosen from compounds of Formulae (1), (2), (3), and (4), Compounds (1-1)-(1-11), Compound (2-1), and pharmaceutically acceptable salts and deuterated derivatives thereof is administered twice daily. In some embodiments, at least one compound chosen from compounds of Formulae (1), (2), (3), and (4), Compounds (1-1)-(1-11), Compound (2-1), and pharmaceutically acceptable salts and deuterated derivatives thereof and at least one compound chosen from Compound II and pharmaceutically acceptable salts thereof are administered once daily. In some embodiments, at least one compound chosen from compounds of Formulae (1), (2), (3), and (4), Compounds (1-1)-(1-11), Compound (2-1), and pharmaceutically acceptable salts and deuterated derivatives thereof and at least one compound chosen from Compound II and pharmaceutically acceptable salts thereof are administered twice daily. In some embodiments, at least one compound chosen from compounds of Formulae (1), (2), (3), and (4), Compounds (1-1)-(1-11), Compound (2-1), and pharmaceutically acceptable salts and deuterated derivatives thereof and at least one compound chosen from Compound III or III-d and pharmaceutically acceptable salts thereof are administered once daily. In some embodiments, at least one compound chosen from compounds of Formulae (1), (2), (3), and (4), Compounds (1-1)-(1-11), Compound (2-1), and pharmaceutically acceptable salts and deuterated derivatives thereof and at least one compound chosen from Compound III or III-d and pharmaceutically acceptable salts thereof are administered twice daily.

In some embodiments, at least one compound chosen from compounds of Formulae (1), (2), (3), and (4), Compounds (1-1)-(1-11), Compound (2-1), and pharmaceutically acceptable salts and deuterated derivatives thereof, at least one compound chosen from Compound II and pharmaceutically acceptable salts thereof, and at least one compound chosen from Compound III or III-d and pharmaceutically acceptable salts thereof are administered once daily. In some embodiments, at least one compound chosen from compounds of Formulae (1), (2), (3), and (4), Compounds (1-1)-(1-11), Compound (2-1), and pharmaceutically acceptable salts and deuterated derivatives thereof, at least one compound chosen from Compound III or III-d and pharmaceutically acceptable salts thereof, and at least one compound chosen from Compound IV and pharmaceutically acceptable salts thereof, are administered once daily. In some embodiments, at least one compound chosen from compounds of Formulae (1), (2), (3), and (4), Compounds (1-1)-(1-11), Compound (2-1), and pharmaceutically acceptable salts and deuterated derivatives thereof, at least one compound chosen from Compound II and pharmaceutically acceptable salts thereof, and at least one compound chosen from Compound III or III-d and pharmaceutically acceptable salts thereof are administered twice daily. In some embodiments, at least one compound chosen from compounds of Formulae (1), (2), (3), and (4), Compounds (1-1)-(1-11), Compound (2-1), and pharmaceutically acceptable salts and deuterated derivatives thereof, at least one compound chosen from Compound III or III-d and pharmaceutically acceptable salts thereof, and at least one compound chosen from Compound IV and pharmaceutically acceptable salts thereof, are administered twice daily.

In some embodiments, at least one compound chosen from compounds of Formulae (1), (2), (3), and (4), Compounds (1-1)-(1-11), Compound (2-1), and pharmaceutically acceptable salts and deuterated derivatives thereof and at least one compound chosen from Compound II and pharmaceutically acceptable salts thereof, are administered once daily and at least one compound chosen from Compound III-d and pharmaceutically acceptable salts thereof, are administered twice daily. In some embodiments, at least one compound chosen from compounds of Formulae (1), (2), (3), and (4), Compounds (1-1)-(1-11), Compound (2-1), and pharmaceutically acceptable salts and deuterated derivatives thereof and at least one compound chosen from Compound IV and pharmaceutically acceptable salts thereof, are administered once daily and at least one compound chosen from Compound III-d and pharmaceutically acceptable salts thereof, are administered twice daily.

Compounds of Formulae (1), (2), (3), and (4), Compounds (1-1)-(1-11), Compound (2-1), Compounds II, (III or III-d), and their pharmaceutically acceptable salts and deuterated derivatives thereof can be administered in a single pharmaceutical composition or separate pharmaceutical compositions. Such pharmaceutical compositions can be administered once daily or multiple times daily, such as twice daily. As used herein, the phrase that a given amount of API (e.g., Compound II, (III, III-d) or a pharmaceutically acceptable salt thereof) is administered once or twice daily or per day means that said given amount is administered per dosing once or twice daily.

In some embodiments, at least one compound chosen from compounds of Formulae (1), (2), (3), and (4), Compounds (1-1)-(1-11), Compound (2-1), and pharmaceutically acceptable salts and deuterated derivatives thereof is administered in a first pharmaceutical composition; at least one compound chosen from Compound II and pharmaceutically acceptable salts thereof is administered in a second pharmaceutical composition; and at least one compound chosen from Compound III and pharmaceutically acceptable salts thereof is administered in a third pharmaceutical composition.

In some embodiments, at least one compound chosen from compounds of Formulae (1), (2), (3), and (4), Compounds (1-1)-(1-11), Compound (2-1), and pharmaceutically acceptable salts and deuterated derivatives thereof is administered in a first pharmaceutical composition; at least one compound chosen from Compound II and pharmaceutically acceptable salts thereof is administered in a second pharmaceutical composition; at least one compound chosen from Compound III-d and pharmaceutically acceptable salts thereof is administered in a third pharmaceutical composition.

In some embodiments, at least one compound chosen from compounds of Formulae (1), (2), (3), and (4), Compounds (1-1)-(1-11), Compound (2-1), and pharmaceutically acceptable salts and deuterated derivatives thereof is administered in a first pharmaceutical composition; at least one compound chosen from Compound III or III-d and pharmaceutically acceptable salts thereof is administered in a second pharmaceutical composition; at least one compound chosen from Compound IV and pharmaceutically acceptable salts thereof is administered in a third pharmaceutical composition.

In some embodiments, at least one compound chosen from compounds of Formulae (1), (2), (3), and (4), Compounds (1-1)-(1-11), Compound (2-1), and pharmaceutically acceptable salts and deuterated derivatives thereof is administered in a first pharmaceutical composition; and at least one compound chosen from Compound II and pharmaceutically acceptable salts thereof and at least one compound chosen from Compound III or III-d, and pharmaceutically acceptable salts thereof are administered in a second pharmaceutical composition. In some embodiments, the second pharmaceutical composition comprises a half of a daily dose of said at least one compound chosen from Compound III, III-d, and pharmaceutically acceptable salts thereof, and the other half of said at least one compound chosen from Compound III, III-d, and pharmaceutically acceptable salts thereof is administered in a third pharmaceutical composition.

In some embodiments, at least one compound chosen from compounds of Formulae (1), (2), (3), and (4), Compounds (1-1)-(1-11), Compound (2-1), and pharmaceutically acceptable salts and deuterated derivatives thereof; at least one compound chosen from Compound II and pharmaceutically acceptable salts thereof and at least one compound chosen from Compound III, III-d, and pharmaceutically acceptable salts thereof are administered in a first pharmaceutical composition. In some embodiments, the first pharmaceutical composition is administered to the patient twice daily. In some embodiments the first pharmaceutical composition is administered once daily. In some embodiments the first pharmaceutical composition is administered once daily and a second composition comprising only Compound III is administered once daily.

Any suitable pharmaceutical compositions known in the art can be used for compounds of Formulae (1), (2), (3), and (4), Compounds (1-1)-(1-11), Compound (2-1), Compound II, Compound III, Compound III-d, and pharmaceutically acceptable salts and deuterated derivatives thereof. Some exemplary pharmaceutical compositions for Compound II and its pharmaceutically acceptable salts can be found in WO 2011/119984 and WO 2014/014841, incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, and some exemplary pharmaceutical compositions for Compound III-d and its pharmaceutically acceptable salts can be found in U.S. Pat. Nos. 8,865,902, 9,181,192, 9,512,079, WO 2017/053455, and WO 2018/080591, all of which are incorporated herein by reference. Some exemplary pharmaceutical compositions for Compound IV and its pharmaceutically acceptable salts can be found in WO 2010/037066, WO 2011/127421, and WO 2014/071122, incorporated herein by reference.

Pharmaceutical Compositions

Another aspect of the invention provides pharmaceutical compositions comprising at least one compound chosen from compounds of Formulae (1), (2), (3), and (4), Compounds (1-1)-(1-11), Compound (2-1), and pharmaceutically acceptable salts and deuterated derivatives thereof. In some embodiments, the invention provides pharmaceutical compositions comprising at least one compound chosen from compounds of Formulae (1), (2), (3), and (4), Compounds (1-1)-(1-11), Compound (2-1), and pharmaceutically acceptable salts and deuterated derivatives thereof in combination with at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises at least one compound chosen from compounds of Formulae (1), (2), (3), and (4), Compounds (1-1)-(1-11), Compound (2-1), and pharmaceutically acceptable salts and deuterated derivatives thereof and at least two additional active pharmaceutical ingredients, one of which is a CFTR corrector and one of which is a CFTR potentiator.

In some embodiments, at least one additional active pharmaceutical ingredient is selected from mucolytic agents, bronchodilators, antibiotics, anti-infective agents, and anti-inflammatory agents.

In some embodiments, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In some embodiments, the additional agent is a mucolyte. Exemplary mucolytes useful herein includes Pulmozyme®.

In some embodiments, the additional agent is a bronchodilator. Exemplary bronchodiltors include albuterol, metaprotenerol sulfate, pirbuterol acetate, salmeterol, or tetrabuline sulfate.

In some embodiments, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In some embodiments, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In some embodiments, the invention provides a pharmaceutical composition comprising at least one compound chosen from compounds of Formulae (1), (2), (3), and (4), Compounds (1-1)-(1-11), Compound (2-1), and pharmaceutically acceptable salts and deuterated derivatives thereof, and at least one pharmaceutically acceptable carrier.

In some embodiments, the invention provides a pharmaceutical composition comprising (a) at least one compound chosen from compounds of Formulae (1), (2), (3), and (4), Compounds (1-1)-(1-11), Compound (2-1), and pharmaceutically acceptable salts and deuterated derivatives thereof, (b) at least one compound chosen from Compound II and pharmaceutically acceptable salts thereof, and (c) at least one pharmaceutically acceptable carrier.

In some embodiments, the disclosure provides a pharmaceutical composition comprising (a) at least one compound chosen from compounds of Formulae (1), (2), (3), and (4), Compounds (1-1)-(1-11), Compound (2-1), and pharmaceutically acceptable salts and deuterated derivatives thereof, (b) at least one compound chosen from Compound III, III-d, and pharmaceutically acceptable salts thereof, and (c) at least one pharmaceutically acceptable carrier.

In some embodiments, the disclosure provides a pharmaceutical composition comprising (a) at least one compound chosen from compounds of Formulae (1), (2), (3), and (4), Compounds (1-1)-(1-11), Compound (2-1), and pharmaceutically acceptable salts and deuterated derivatives thereof, (b) at least one compound chosen from Compound II and pharmaceutically acceptable salts thereof, (c) at least one compound chosen from Compound III and pharmaceutically acceptable salts thereof, and (d) at least one pharmaceutically acceptable carrier.

In some embodiments, the disclosure provides a pharmaceutical composition comprising (a) at least one compound chosen from compounds of Formulae (1), (2), (3), and (4), Compounds (1-1)-(1-11), Compound (2-1), and pharmaceutically acceptable salts and deuterated derivatives thereof, (b) at least one compound chosen from Compound II and pharmaceutically acceptable salts thereof, (c) at least one compound chosen from Compound III-d and pharmaceutically acceptable salts thereof, and (d) at least one pharmaceutically acceptable carrier.

In some embodiments, the disclosure provides a pharmaceutical composition comprising (a) at least one compound chosen from compounds of Formulae (1), (2), (3), and (4), Compounds (1-1)-(1-11), Compound (2-1), and pharmaceutically acceptable salts and deuterated derivatives thereof, (b) at least one compound chosen from Compound III or III-d and pharmaceutically acceptable salts thereof, (c) at least one compound chosen from Compound IV and pharmaceutically acceptable salts thereof, and (d) at least one pharmaceutically acceptable carrier.

Any pharmaceutical composition disclosed herein may comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

The pharmaceutical compositions described herein are useful for treating cystic fibrosis and other CFTR mediated diseases.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams &

Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

Additional embodiments include:

1. A compound of Formula (1):

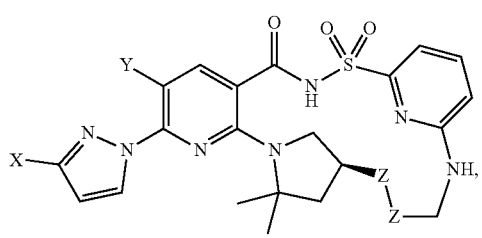

(1)

or a pharmaceutically acceptable salt or deuterated derivative thereof,
wherein:
X is selected from $Si(R)_3$, $-(O)_n-(C_1-C_8$ alkyl), $-(O)_n-(C_3-C_{10}$ cycloalkyl), wherein:
  n is 0 or 1,
  each $C_1-C_8$ alkyl is substituted with 0, 1, 2, or 3 groups selected from halogen, hydroxy, oxo, $C_3-C_{10}$ cycloalkyl, $C_1-C_4$ haloalkyl, and $Si(R)_3$ groups,
  each $C_3-C_{10}$ cycloalkyl is substituted with 0, 1, 2, 3, or 4 groups selected from halogen, $C_1-C_4$ haloalkyl, $C_1-C_4$ alkyl, and $Si(R)_3$ groups, and
  one $-CH_2-$ in each $C_1-C_8$ alkyl is optionally replaced with $-Si(R)_2-$;

Y is selected from hydrogen and $-Si(R)_3$;
each Z is independently selected from $-CH_2-$ and $-Si(R)_2-$; and
each R is independently selected from phenyl and $C_1-C_6$ alkyl groups; and
wherein the compound of Formula (1) contains at least one Si atom.

2. The compound of embodiment 1, wherein X is selected from $Si(R)_3$,

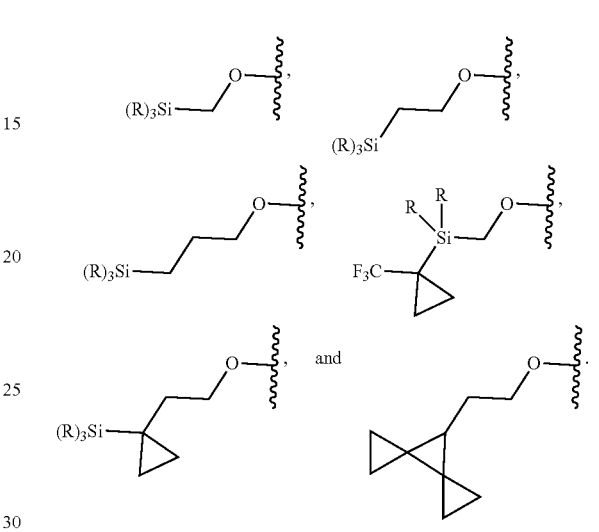

3. The compound of any one of embodiments 1 or 2, wherein the compound is chosen from:

Compound (1-1)

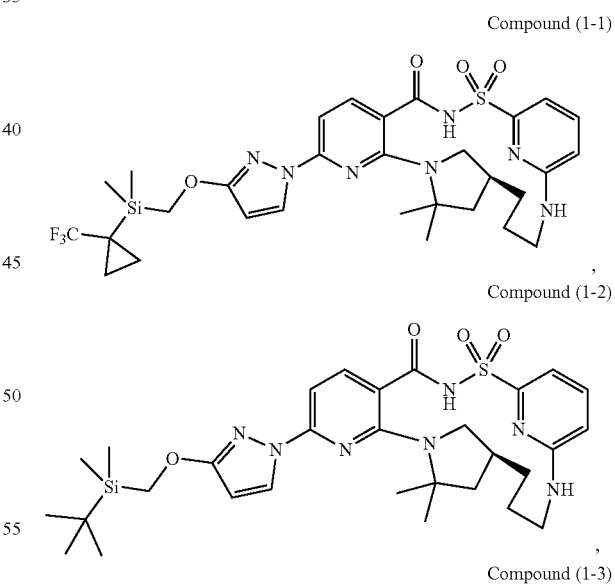

Compound (1-2)

Compound (1-3)

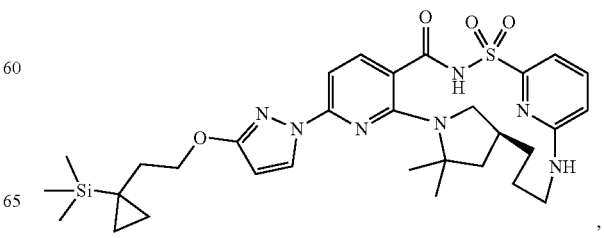

-continued

Compound (1-4)

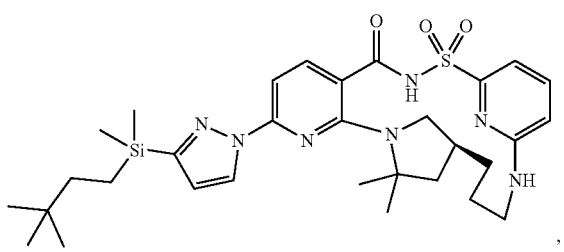

Compound (1-5)

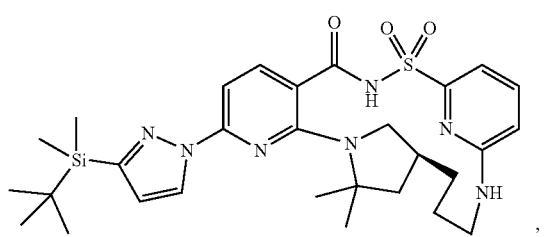

Compound (1-6)

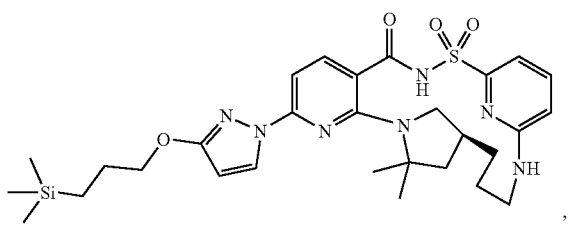

Compound (1-7)

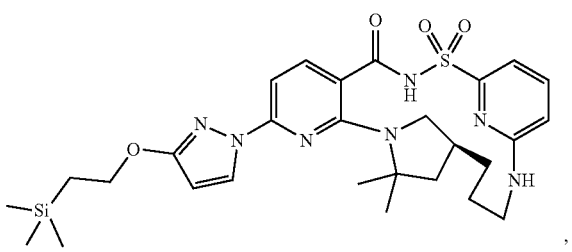

Compound (1-8)

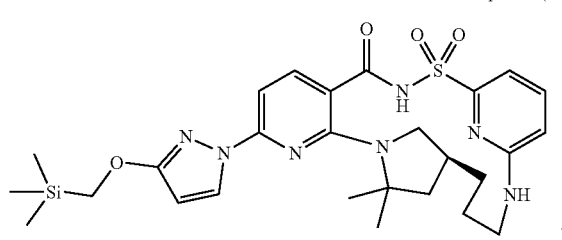

Compound (1-9)

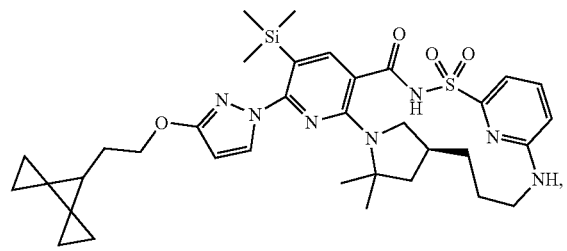

-continued

Compound (1-10)

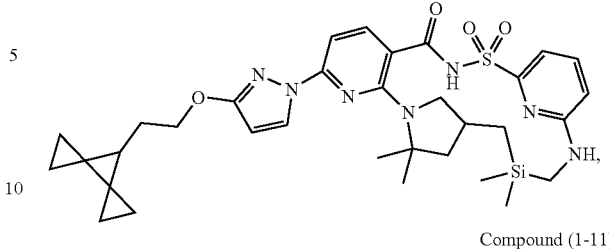

Compound (1-11)

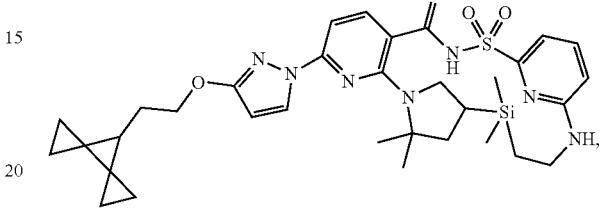

and pharmaceutically acceptable salts and deuterated derivatives thereof.

4. The compound of any one of embodiments 1 to 3, wherein at least one hydrogen is replaced by deuterium.

5. The compound of any one of embodiments 1 to 4, wherein the compound is a pharmaceutically acceptable salt.

6. A compound of Formula (2):

(2)

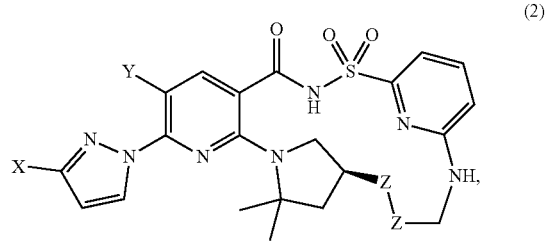

or a pharmaceutically acceptable salt or deuterated derivative thereof, wherein:

X is selected from Ge(R)$_3$, —(O)$_n$—(C$_1$-C$_8$ alkyl), —(O)$_n$—(C$_3$-C$_{10}$ cycloalkyl), wherein:
  n is 0 or 1,
  each C$_1$-C$_8$ alkyl is substituted with 0, 1, 2, or 3 groups selected from halogen, hydroxy, oxo, C$_3$-C$_{10}$ cycloalkyl, C$_1$-C$_4$ haloalkyl, and Ge(R)$_3$ groups,
  each C$_3$-C$_{10}$ cycloalkyl is substituted with 0, 1, 2, 3, or 4 groups selected from halogen, C$_1$-C$_4$ haloalkyl, C$_1$-C$_4$ alkyl, and Ge(R)$_3$ groups, and
  one —CH$_2$— in each C$_1$-C$_8$ alkyl is optionally replaced with —Ge(R)$_2$—;

Y is selected from hydrogen and —Ge(R)$_3$;

each Z is independently selected from —CH$_2$— and —Ge(R)$_2$—; and each R is independently selected from phenyl and C$_1$-C$_6$ alkyl groups; and wherein the compound of Formula (2) contains at least one Ge atom.

7. The compound of embodiment 6, wherein X is selected from Ge(R)$_3$,

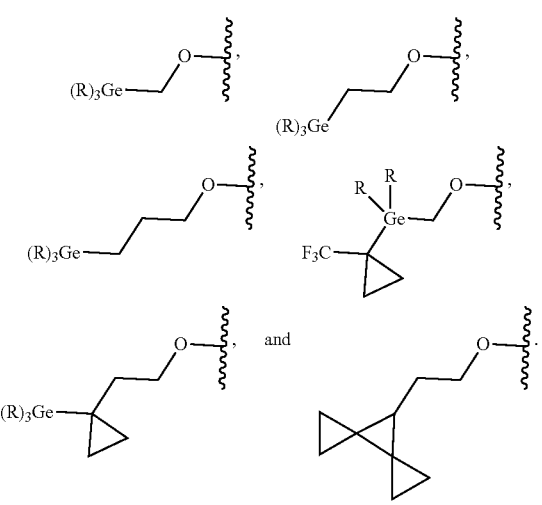

8. The compound of any one of embodiments 6 or 7, wherein the compound is chosen from:

Compound (2-1)

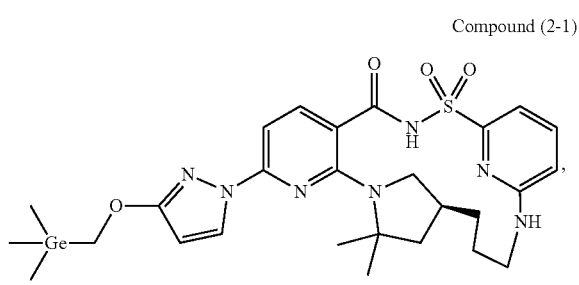

and pharmaceutically acceptable salts and deuterated derivatives thereof.

9. The compound of any one of embodiments 6 to 8, wherein at least one hydrogen is replaced by deuterium.

10. The compound of any one of embodiments 6 to 9 wherein the compound is a pharmaceutically acceptable salt.

11. A compound of Formula (3):

(3)

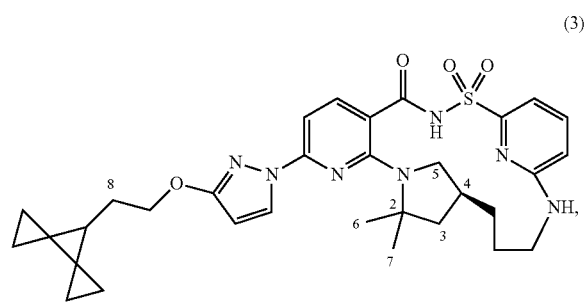 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

or a pharmaceutically acceptable salt or deuterated derivative thereof, wherein:

the carbon atom at position 2 of Formula (3) is replaced by a silicon atom;

at least one of the methyl groups at positions 6 and 7 of Formula (3) is replaced by a group chosen from —Si(R)$_3$ groups, —Si(R)$_2$(OR) groups, and —Si(R)(OR)$_2$ groups;

at least one of the methylene groups at positions 3, 5, and 8 of Formula (3) is replaced by a group chosen from >Si(R)$_2$ groups and >Si(R)(OR) groups; and/or the methine group at position 4 of Formula (3) is replaced by a group chosen from ≡Si(R) groups and ≡Si(OR) groups; and wherein each R is independently chosen from hydrogen, phenyl, and C$_1$-C$_6$ alkyl groups.

12. A compound of Formula (4):

(4)

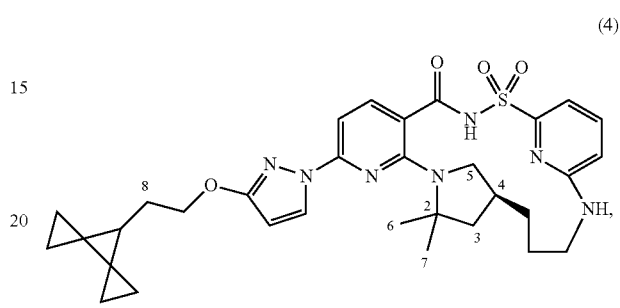

or a pharmaceutically acceptable salt or deuterated derivative thereof, wherein:

the carbon atom at position 2 of Formula (4) is replaced by a germanium atom;

at least one of the methyl groups at positions 6 and 7 of Formula (4) is replaced by a group chosen from —Ge(R)$_3$ groups, —Ge(R)$_2$(OR) groups, and —Ge(R)(OR)$_2$ groups;

at least one of the methylene groups at positions 3, 5, and 8 of Formula (4) is replaced by a group chosen from >Ge(R)$_2$ groups and >Ge(R)(OR) groups; and/or the methine group at position 4 of Formula (4) is replaced by a group chosen from ≡Ge(R) groups and ≡Ge(OR) groups; and wherein each R is independently chosen from hydrogen, phenyl, and C$_1$-C$_6$ alkyl groups.

13. The compound of embodiment 11 or 12, wherein at least one hydrogen is replaced by deuterium.

14. The compound of any one of embodiments 11 to 13, wherein the compound is a pharmaceutically acceptable salt.

15. A pharmaceutical composition comprising a compound of any one of embodiments 1-14 and a pharmaceutically acceptable carrier.

16. The pharmaceutical composition of embodiment 15, further comprising one or more additional therapeutic agent(s).

17. The pharmaceutical composition of embodiment 16, wherein the one or more additional therapeutic agent(s) comprise(s) a compound selected from Compound II, Compound III, Compound III-d, and pharmaceutically acceptable salts thereof.

18. The pharmaceutical composition of embodiment 17, wherein the composition comprises Compound II and Compound III.

19. The pharmaceutical composition of embodiment 17, wherein the composition comprises Compound II and Compound III-d.

20. A pharmaceutical composition comprising:

(a) at least one compound chosen from compounds of any one of embodiments 1-14;

(b) at least one pharmaceutically acceptable carrier; and optionally one or more of:

(c) (i) a compound chosen from Compound II:

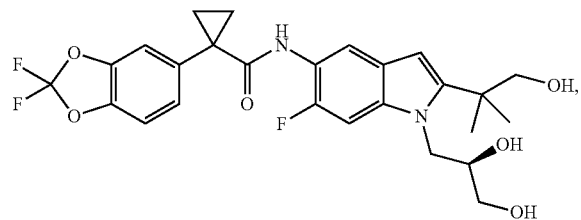 [SMILES: CC(C)(CO)c1cc2cc(NC(=O)C3(c4ccc5c(c4)OC(F)(F)O5)CC3)c(F)cc2n1C[C@@H](O)CO]

and pharmaceutically acceptable salts and deuterated derivatives thereof; and (ii) a compound chosen from Compound III, Compound III-d:

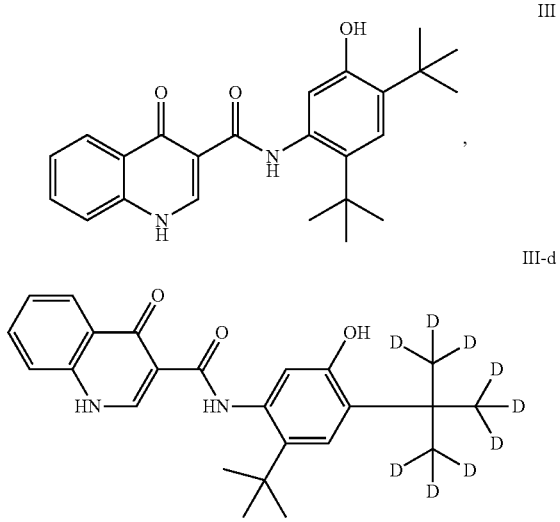

and pharmaceutically acceptable salts and deuterated derivatives thereof.

21. A method of treating cystic fibrosis comprising administering to a patient in need thereof a compound of any one of embodiments 1-14 or a pharmaceutical composition according to any one of embodiments 15-20.

22. The method of embodiment 21, further comprising administering to the patient one or more additional therapeutic agent(s) prior to, concurrent with, or subsequent to the compound or the pharmaceutical composition.

23. The method of embodiment 22, wherein the one or more additional therapeutic agent(s) comprise(s) a compound selected from Compound II, Compound III, Compound III-d, and pharmaceutically acceptable salts thereof.

24. The method of embodiment 23, wherein the one or more additional therapeutic agent(s) comprise(s) Compound II and Compound III.

25. The method of embodiment 23, wherein the one or more additional therapeutic agent(s) comprise(s) Compound II and Compound III-d.

26. The compound of any one of embodiments 1-14 or the pharmaceutical composition according to any one of embodiments 15-20 for use in the treatment of cystic fibrosis.

27. The compound of any one of embodiments 1-14 or the pharmaceutical composition according to any one of embodiments 15-20 for use in the manufacture of a medicament for the treatment of cystic fibrosis.

EXAMPLES

General Experimental Procedures

Compounds II, III, III-d, and IV can be prepared by any suitable method in the art, for example, PCT Publication Nos. WO 2011/133751, WO 2011/133951, WO 2015/160787 and U.S. Pat. No. 8,865,902.

Abbreviation List

ACN: Acetonitrile
Boc anhydride ((Boc)$_2$O): Di-tert-butyl dicarbonate
CDI: Carbonyl diimidazole
COMU: (1-Cyano-2-ethoxy-2-oxoethylidenaminooxy)dimethylamino-morpholino-carbenium hexafluorophosphate
DABCO: 1,4-Diazabicyclo[2.2.2]octane
DBU: 1,8-Diazabicyclo(5.4.0)undec-7-ene
Agent Ref No.: 10275.0163-00000
DCM: Dichloromethane
DI water: Deionized water
DIAD: Diisopropyl azodicarboxylate
DIEA (DIPEA; N,N-diisopropylethylamine)
DMA: N,N-Dimethylacetamide
DMAP: 4-dimethylaminopyridine
DMF: N,N-Dimethylformamide
DMSO: Dimethyl sulfoxide
EA: Ethyl acetate
EDC: 1-Ethyl-3-(3-dimethylaminopropyl)carbodiimide
Et$_2$O: Diethyl ether
EtOAc: Ethyl acetate
EtOH: Ethanol
HATU: 1-[Bis(dimethylamino)methylene]-1H-1,2,3-triazolo[4,5-b]pyridinium 3-oxid hexafluorophosphate
HPLC: High performance liquid chromatography
HMPA: Hexamethylphosphoramide
IPA: Isopropanol
LAH: Lithium aluminum hydride
LC: Liquid chromatography
LDA: Lithium diisopropylamide
MeCN: Acetonitrile
MeOH: Methanol
MTBE: Methyl tert-butyl ether
MeTHF or 2-MeTHF: 2-Methyltetrahydrofuran
NMP: N-Methyl-2-pyrrolidone
NMM: N-Methylmorpholine
Pd(dppf)Cl2: [1,1'-Bis(diphenylphosphino)ferrocene]dichloropalladium(II)
PTFE: Polytetrafluoroethylene
Rpm: revolutions per minute
rt: Room temperature
SFC: Supercritical fluid chromatography
TBS-Cl: tert-Butyldimethylsilyl chloride
TEA: Triethylamine
TFA: Trifluoroacetic acid
THF: Tetrahydrofuran
TMS: Trimethylsilyl
TMSCl: Trimethylsilyl chloride
TPPO-DIAD complex: a complex of triphenylphosphine oxide with diisopropyl azodicarboxylate
p-TsOH: p-Toluenesulfonic Acid
UPLC: Ultra Performance Liquid Chromatography
Procedures for the Synthesis of Common Intermediates Reagents and starting materials were obtained by commercial sources unless otherwise stated and were used without purification.

Proton and carbon NMR spectra were acquired on either a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

NMR (1D & 2D) spectra were also recorded on a Bruker AVNEO 400 MHz spectrometer operating at 400 MHz and 100 MHz respectively equipped with a 5 mm multinuclear Iprobe.

NMR spectra were also recorded on a Varian Mercury NMR instrument at 300 MHz for $^1$H using a 45 degree pulse angle, a spectral width of 4800 Hz and 28860 points of acquisition. FID were zero-filled to 32 k points and a line broadening of 0.3 Hz was applied before Fourier transform. $^{19}$F NMR spectra were recorded at 282 MHz using a 30 degree pulse angle, a spectral width of 100 kHz and 59202 points were acquired. FID were zero-filled to 64 k points and a line broadening of 0.5 Hz was applied before Fourier transform.

NMR spectra were also recorded on a Bruker Avance III HD NMR instrument at 400 MHz for $^1$H using a 30 degree pulse angle, a spectral width of 8000 Hz and 128 k points of acquisition. FID were zero-filled to 256 k points and a line broadening of 0.3 Hz was applied before fourrier transform. $^{19}$F NMR spectra were recorded at 377 MHz using a 30 deg pulse angle, a spectral width of 89286 Hz and 128 k points were acquired. FID were zero-filled to 256 k points and a line broadening of 0.3 Hz was applied before Fourier transform.

NMR spectra were also recorded on a Bruker AC 250 MHz instrument equipped with a: 5 mm QNP(H1/C13/F19/P31) probe (type: 250-SB, s #23055/0020) or on a Varian 500 MHz instrument equipped with a ID PFG, 5 mm, 50-202/500 MHz probe (model/part #99337300).

Final purity of compounds was determined by reversed phase UPLC using an Acquity UPLC BEH Cis column (50×2.1 mm, 1.7 μm particle) made by Waters (pn: 186002350), and a dual gradient run from 1-99% mobile phase B over 3.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as [M+1]$^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30 m×0.25 mm×0.25 μm_df) column, with a 2.0 mL/min flow rate ($H_2$ carrier gas), at an injection temperature of 220° C. and an oven temperature of 120° C., 15 minutes.

Example 1: Synthesis of tert-butyl 3-oxo-2,3-dihydro-H-pyrazole-1-carboxylate

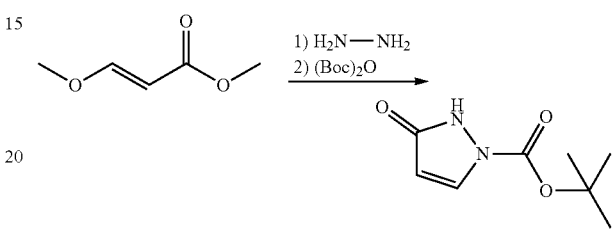

A 50 L reactor was started, and the jacket was set to 20° C., with stirring at 150 rpm, reflux condenser (10° C.) and nitrogen purge. MeOH (2.860 L) and methyl (E)-3-methoxyprop-2-enoate (2.643 kg, 22.76 mol) were added, and the reactor was capped. The reaction was heated to an internal temperature of 40° C., and the system was set to hold jacket temperature at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethylamine (2.483 kg, 3.420 L, 24.54 mol) was added portion-wise, maintaining reaction temperature <30° C. A solution of Boc anhydride (di-tert-butyl dicarbonate) (4.967 kg, 5.228 L, 22.76 mol) in MeOH (2.860 L) was added portion-wise maintaining temperature <45° C. The reaction mixture was stirred at 20° C. for 16 h. The reaction solution was partially concentrated to remove MeOH, resulting in a clear, light amber oil. The resulting oil was transferred to the 50 L reactor, stirred and water (7.150 L) and heptane (7.150 L) were added. The additions caused a small amount of the product to precipitate. The aqueous layer was drained into a clean container, and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol) and added dropwise. The jacket was set to 0° C. to absorb the quench exotherm. After the addition was complete (pH=5), the reaction mixture was stirred for 1 h. The solid was collected by filtration and washed with water (7.150 L), and washed a second time with water (3.575 L). The crystalline solid was transferred into a 20 L rotovap bulb, and heptane (7.150 L) was added. The mixture was slurried at 45° C. for 30 mins, and 1-2 volumes of solvent were distilled off. The slurry in the rotovap flask was filtered, and the solids were washed with heptane (3.575 L). The solid was further dried in vacuo (50° C., 15 mbar) to give tert-butyl 5-oxo-1H-pyrazole-2-carboxylate (2921 g, 71%) as a coarse, crystalline solid. $^1$HNMR (400 MHz, DMSO-d6) δ 10.95 (s, 1H), 7.98 (d, J=2.9 Hz, 1H), 5.90 (d, J=2.9 Hz, 1H), 1.54 (s, 9H).

Example 2: Synthesis of (14S)-8-bromo-12,12-dimethyl-2λ⁶-thia-3,9,11,18,23-pentaazatetracyclo[17.3.1.111,14.05,10]tetracosa-1(23),5(10),6,8,19,21-hexaene-2,2,4-trione
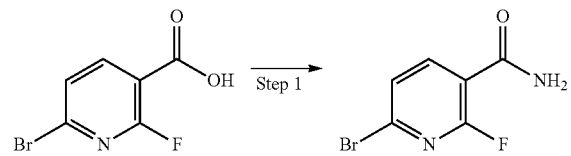
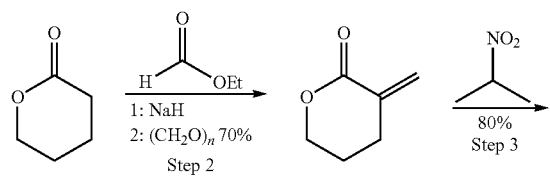
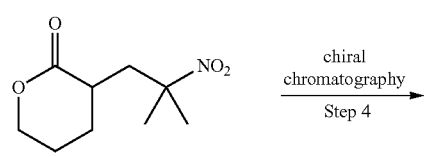
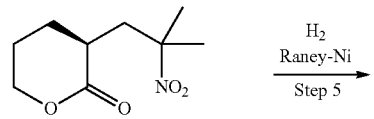
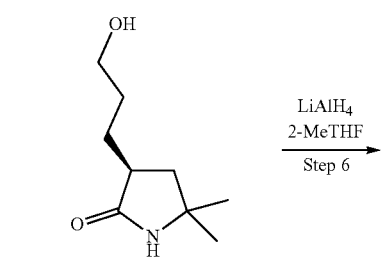
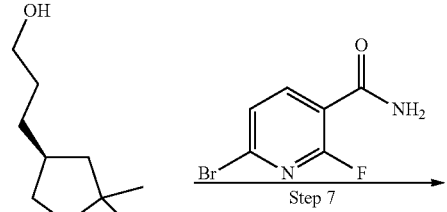
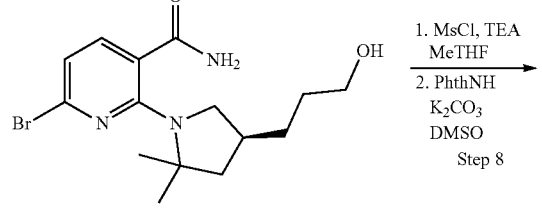
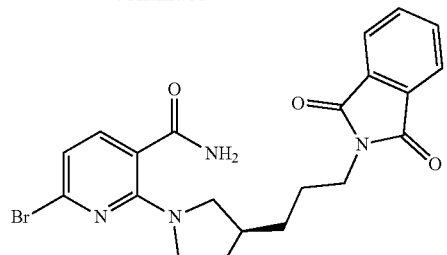
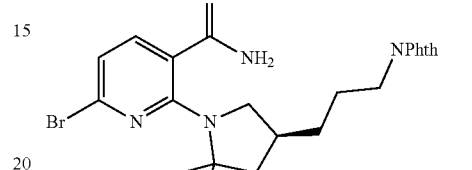
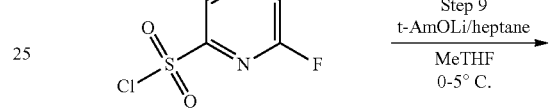
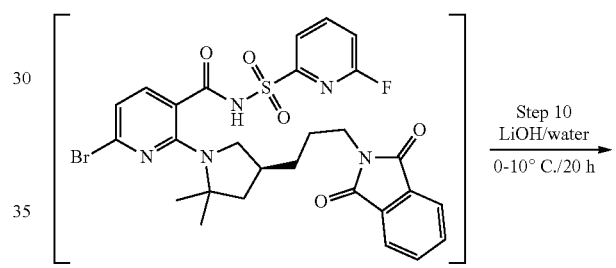
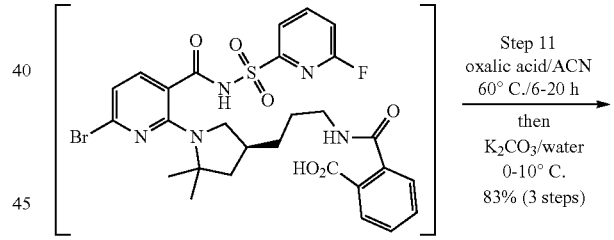
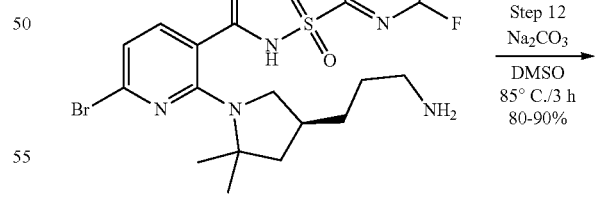
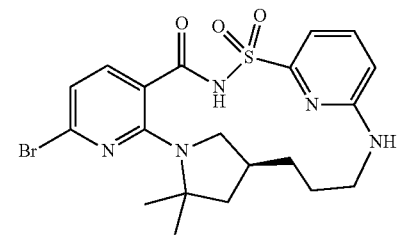

Step 1: 6-Bromo-2-fluoro-pyridine-3-carboxamide

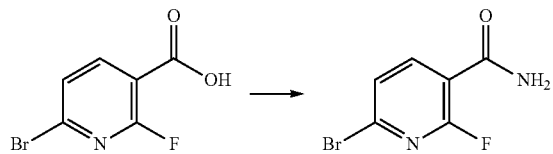 [SMILES: O=C(O)c1ccc(Br)nc1F ; NC(=O)c1ccc(Br)nc1F]

To a solution of 6-bromo-2-fluoro-pyridine-3-carboxylic acid (24.7 g, 106.66 mmol) and Boc$_2$O (33 g, 146.67 mmol) in 2-MeTHF (250 mL) was added NMM (13.80 g, 15 mL, 136.44 mmol). The mixture was stirred for 30 min at room temperature and then NH$_4$HCO$_3$ (15 g, 189.74 mmol) was added. The reaction mixture was stirred for 20 hours at room temperature. Water (200 mL) and EtOAc (100 mL) were added and the mixture was stirred for 10 min. The two phases were separated. The organic layer was washed with saturated sodium bicarbonate, brine, dried over sodium sulfate and concentrated to give 6-bromo-2-fluoro-pyridine-3-carboxamide (23.5 g, 96%) as a light color solid. ESI-MS m/z calc. 217.9491, found 219.3 (M+1)$^+$; Retention time: 2.33 minutes (LC method B).

Step 2: 3-Methylenetetrahydro-2H-pyran-2-one

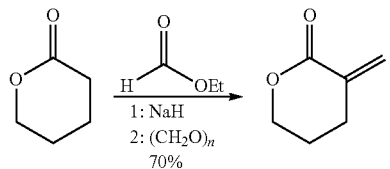

Stage 1

A 5 L 3 neck RB flask was fitted with a mechanical stirrer, a heating mantle, an addition funnel, a J-Kem temperature probe/controller and a nitrogen inlet/outlet. The vessel was charged under a nitrogen atmosphere with sodium hydride (59.91 g of 60% w/w, 1.498 mol) followed by heptane (1.5 L) which provided a grey suspension. Stirring was commenced and the pot temperature was recorded at 19° C. The vessel was then charged with ethyl alcohol (3.451 g, 74.91 mmol) added via syringe which resulted in gas evolution. The addition funnel was charged with a clear pale yellow solution of tetrahydropyran-2-one (150 g, 1.498 mol) and ethyl formate (111 g, 1.50 mol). The solution was added dropwise over 1 hour which resulted in gas evolution and a gradual exotherm to 45° C. The resulting thick white suspension was then heated to 65° C. for 2 hours and then allowed to cool to RT. The mixture was continued to stir at RT overnight (about 10 hours). The reaction mixture was vacuum filtered through a glass frit Buchner funnel (Medium porosity) under a stream of nitrogen. The filter cake was displacement washed with heptane (2×250 mL) and pulled for a few minutes. The slightly heptane wet cake was transferred to a glass tray and dried in a vacuum oven at 45° C. for 15 hours to provide a white solid (205 g, 1.36 mol, 91% yield) as the desired product (E)-(2-oxotetrahydropyran-3-ylidene)methanolate. $^1$HNMR (400 MHz, DMSO-d$_6$) δ 8.99 (s, 1H), 3.90-3.83 (m, 2H), 2.09 (t, J=6.3 Hz, 2H), 1.57 (qd, J=6.4, 4.7 Hz, 2H).

Stage 2

A 5 L 3 neck RB flask was fitted with a mechanical stirrer, a heating mantle, an addition funnel, a J-Kem temperature probe/controller and a nitrogen inlet/outlet. The vessel was charged under a nitrogen atmosphere with (E)-(2-oxotetrahydropyran-3-ylidene)methanolate-Na salt (205 g, 1.366 mol) and tetrahydrofuran (1640 mL) which provided a white suspension. Stirring was commenced and the pot temperature was recorded at 19° C. The vessel was then charged with paraformaldehyde (136.6 g, 4.549 mol) added as a solid in one portion. The resulting suspension was heated to 63° C. and the condition was maintained for 15 hours. Upon heating the reaction mixture became slightly gelatinous. The white gelatinous mixture was concentrated under reduced pressure to remove most of the tetrahydrofuran. The remaining residue was partitioned with ethyl acetate (1000 mL), saturated sodium chloride (500 mL) and saturated sodium hydrogen carbonate (500 mL) in a separatory funnel. The organic was removed and the residual aqueous was extracted with ethyl acetate (5×300 mL). The combined organic was dried over sodium sulfate (500 g) and then vacuum filtered through a glass frit Buchner funnel with a 20 mm layer of Celite. The filter cake was displacement washed with ethyl acetate (250 mL). The clear filtrate was concentrated under reduced pressure to provide a clear pale yellow oil (135 g) as the desired crude product. The material was purified by silica gel column flash chromatography (liquid load) on the Isco (1500 g RediSep column) eluting with a gradient of 100% hexane to 60% ethyl acetate in hexane over 1 hour collecting 450 mL fractions. The product was detected by TLC analysis on silica gel eluting with 3:1 Hex/EtOAc and visualized under UV. The product fractions were combined and concentrated under reduced pressure to provide a clear colorless oil (132 g, 1.18 mol, 86% yield) as the desired product 3-methylenetetrahydropyran-2-one. $^1$HNMR (400 MHz, DMSO-d$_6$) δ 6.18 (q, J=1.9 Hz, 1H), 5.60 (q, J=1.9 Hz, 1H), 4.40-4.26 (m, 2H), 2.61 (ddt, J=7.0, 6.3, 2.0 Hz, 2H), 1.90-1.75 (m, 2H). The proton NMR indicated about 16 wt % residual ethyl acetate. The corrected yield was: (100-16=84) 0.84(132)=110.9 g (72% yield).

Step 3: 3-(2-Methyl-2-nitropropyl)tetrahydro-2H-pyran-2-one

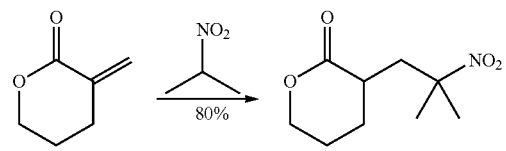

A 5000 mL 3 neck RB flask was fitted with a mechanical stirrer, a cooling bath used as secondary containment, a J-Kem temperature probe, an addition funnel and a nitrogen inlet/outlet. The vessel was charged under a nitrogen atmosphere with 2-Nitropropane (104.9 g, 1.177 mol). Stirring was commenced and the pot temperature was recorded at 19° C. The vessel was then charged with 1,8-diazabicyclo [5.4.0]undec-7-ene (22.41 g, 147.2 mmol) added neat in one portion which resulted in a clear light yellow solution. No exotherm was observed. The addition funnel was charged with a solution of 3-methylenetetrahydropyran-2-one (110 g, 981.0 mmol) in acetonitrile (1100 mL) which was added dropwise over 1 hour which resulted in a clear light yellow solution and a gradual exotherm to 24° C. The reaction mixture was continued to stir at RT for 3.5 hours and then concentrated under reduced pressure. The remaining residue was dissolved in dichloromethane (1000 mL) and partitioned with 500 mL of a 3:2 mixture of 1 molar citric acid solution/saturated sodium chloride solution. The organic phase was removed and the residual aqueous was extracted with dichloromethane (300 mL). The combined organic phase was washed with saturated sodium chloride solution (300 mL), dried over sodium sulfate (250 g) and then filtered through a glass frit Buchner funnel. The filtrate was concentrated under reduced pressure to a volume of about 200 mL. The clear pale blue dichloromethane solution was diluted with methyl tert-butyl ether (1500 mL) and the cloudy solution was concentrated under reduced pressure to a volume of about 200 mL which provided a suspension. The mixture was again diluted with methyl tert-butyl ether (1500 mL) and concentrated under reduced pressure to a volume of about 250 mL. The resulting suspension was allowed to stand at RT overnight (about 12 hours). The solid was collected by vacuum filtration in a glass frit Buchner funnel and the filter cake was displacement washed with cold methyl tert-butyl ether (2×150 mL) and then pulled for 30 minutes. The material was further dried in a vacuum oven at 45° C. for 5 hours to provide (160 g, 0.795 mol, 81% yield) of a white solid as the desired product, 3-(2-methyl-2-nitropropyl)tetrahydropyran-2-one. $^1$HNMR (400 MHz, DMSO-$d_6$) δ 4.34 (ddd, J=11.1, 9.3, 4.3 Hz, 1H), 4.20 (dt, J=11.1, 5.1 Hz, 1H), 2.75-2.62 (m, 1H), 2.56 (dd, J=14.9, 5.2 Hz, 1H), 2.01-1.89 (m, 2H), 1.89-1.67 (m, 2H), 1.55 (d, J=6.0 Hz, 6H), 1.44 (dddd, J=12.8, 11.5, 8.1, 6.6 Hz, 1H). ESI-MS m/z calc. 201.10011, found 202.0 (M+1)$^+$; Retention time: 0.97 minutes as an off white solid.

Step 4: Chiral Separation of Racemic 3-(2-Methyl-2-nitropropyl)tetrahydro-2H-pyran-2-one

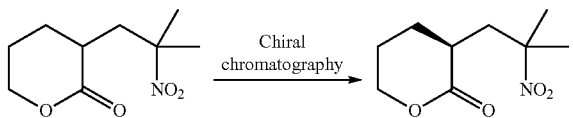

Racemic 3-(2-Methyl-2-nitropropyl)tetrahydro-2H-pyran-2-one was dissolved to 80 g/L+/−8 g/L in MeOH/ACN 70/30 v/v (target 80+/−2 g/L) and separated on Chiralpak AD 20 μm as the stationary phase using MeOH/ACN 70/30 v/v as the mobile phase. (S)-3-(2-methyl-2-nitropropyl)tetrahydro-2H-pyran-2-one was Peak 2.

Step 5: (S)-3-(3-Hydroxypropyl)-5,5-dimethylpyrrolidin-2-one

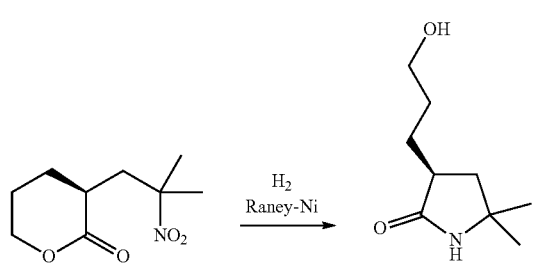

A suspension of Raney Nickel 2400 (77 wt %, 2.8 kg) was allowed to settle for 2 days. The standing liquid was decanted to waste and the remaining catalyst was charged to a reactor with the aide of water (2.6 kg then degassed with N2. In a second reactor a mixture of (S)-3-(2-methyl-2-nitropropyl)tetrahydro-2H-pyran-2-one (13.9 kg) and EtOH (170.8 kg) was heated to 30° C. then degassed with N2 then transferred to the reactor containing Raney Nickel. The transfer was completed with the aid of an EtOH (29.8 kg) rinse. The mixture was purged three times with nitrogen and purged three times with hydrogen. The contents of the reactor were heated to 60-65° C. and stirred under $H_2$ (4-8 psig) until the reaction was completed (18 h). The mixture was cooled to 15-20° C. then purged with nitrogen three times then filtered through a pad of Celite (3.0 kg) wetted with EtOH (3.2 kg). The reactor and Celite cake were washed with EtOH (2×14.0 kg). The filtrate was distilled to a final volume of approx. 25 L then heated to 45° C. MTBE (269.4 kg) was then charged maintaining 48-50° C. and then distilled at ambient pressure at 48-55° C. to a final volume of approx. 30 L. Two further portions of MTBE (269.4 kg then 187.4 kg) were sequentially added then concentrated to approx. 30 L volume.

The contents of the reactor were seeded with (S)-3-(3-hydroxypropyl)-5,5-dimethylpyrrolidin-2-one (70.1 g) at 40° C. The seeded crystal slurry was cooled to 15° C. over a period of 3.5 h then stirred for 16.5 h and 30 min between 12-15° C. then filtered. The reactor and filter cake were then washed with cold (−2 to −10° C.) MTBE (2×10 kg). The filter-cake was dried to a constant weight which afforded (S)-3-(3-hydroxypropyl)-5,5-dimethylpyrrolidin-2-one (10.4 kg; 88%) as a white, crystalline solid.

Recrystallization of (S)-3-(3-Hydroxypropyl)-5,5-dimethylpyrrolidin-2-one

A mixture of (S)-3-(3-hydroxypropyl)-5,5-dimethylpyrrolidin-2-one (10.3 kg) and DCM (28.2 kg) was stirred and heated to 25° C. for 2 h then transferred to another reactor through an in-line filter (45 um). The initial reactor was rinsed with DCM (6.8 kg) at 21° C. for 10 min then transferred to the reactor through the in-line filter. MTBE (38.1 kg) was charged to the solution at 25-30° C. then the mixture was distilled over a period of 2.5 h at 35-52° C. at atmospheric pressure to a final volume of approx. 30 L. MTBE (38.2 kg) was charged to the reactor at 45-50° C. The resulting suspension was distilled over a period of 3.25 h at 49-55° C. at atmospheric pressure to a final volume of approx. 30 L. The contents of the reactor were cooled to 21° C. over a period of 2.5 h and stirred for 16 h at 20° C. The suspension was filtered. The reactor and filter cake were rinsed with MTBE (7.7 kg, 0° C.). The filter cake was dried over a period of 2 days. Yield: 9.1 kg (88.3%) of an off-white solid.

Step 6: (S)-3-(5,5-dimethylpyrrolidin-3-yl)propan-1-ol

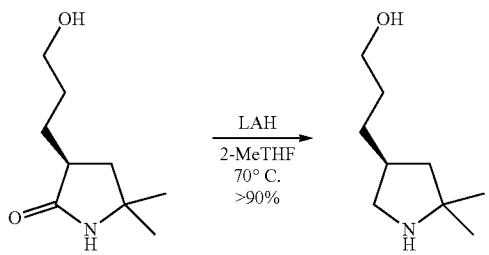

LAH pellets (332.5 g, 8.760 mol, 1.50 eq) were slowly added to a reactor 2-MeTHF (10.00 L, 10 vol) at 30-40° C. The mixture was then heated to 75° C. A mixture of (S)-3-(3-Hydroxypropyl)-5,5-dimethylpyrrolidin-2-one (1,000 g, 5.840 mol, 1.00 equiv) and 2-MeTHF (10.00 L, 10 vol) was prepared in a separate reactor and heated to 65° C. then carefully transferred reactor containing the LAH mixture over 2 h. The mixture was stirred at 70° C. until the reaction was complete (18-24 hours) then cooled to 0-10° C. Water (400.0 mL, 1×LAH wt) was then carefully added while maintaining the mixture temperature <30° C. A solution of aq 15% NaOH (400.0 mL, 1×LAH wt) was then added followed by water (400.0 mL, 1×LAH wt) while maintaining the mixture temperature <30° C. The resulting mixture was then heated to 60° C. and held at temperature for at least 30 minutes. The mixture was cooled to 20-30° C. then Celite (200 grams, 20 wt %) was added. The mixture was then filtered through a pad of Celite. The reactor and filter cake were rinsed with 2-MeTHF (4.0 L, 4.0 vol). The filtrate was concentrated under vacuum to afford (S)-3-(5,5-dimethylpyrrolidin-3-yl)propan-1-ol (872 g; 94.95% yield) as a clear oil.

Step 7: (S)-6-bromo-2-(4-(3-hydroxypropyl)-2,2-dimethylpyrrolidin-1-yl)nicotinamide 6-bromo-2-fluoronicotinamide

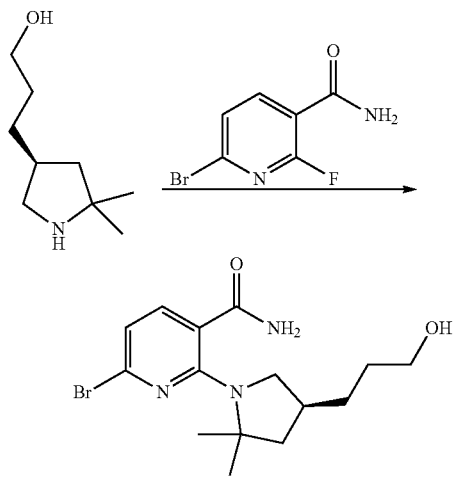

A mixture of (S)-3-(5,5-dimethylpyrrolidin-3-yl)propan-1-ol (2325 g, 14.8 mol) and 6-bromo-2-fluoronicotinamide (3400 g, 15.5 mol) in 2-methyltetrahydrofuran (23 L) was stirred then potassium carbonate (2650 g, 19.2 mol) and deionized water (7 L) were added. The mixture was stirred at 25° C. until the reaction was complete (>16 h). The aqueous phase was removed and the upper organic phase was washed with water (7 L) and 2% aqueous sodium chloride (7 L). The organic layer was concentrated under reduced pressure to about 19 L. 2-Methyltetrahydrofuran was chased from the mixture by two sequential additions and concentrations of acetonitrile (2×20 L) followed by distillation. To the remaining solution was added acetonitrile (20 L) and the reaction was warmed to 85° C. for 2 h and then cooled at 10° C./h to 25° C. The slurry was cooled 10° C. and stirred for 4 h then filtered. The cake was rinsed two times with acetonitrile (2×3 L) then the solid was dried under vacuum to afford (S)-6-bromo-2-(4-(3-hydroxypropyl)-2,2-dimethylpyrrolidin-1-yl)nicotinamide as a crystalline white solid (3850 g, 73% yield).

Step 8: Synthesis of (S)-6-bromo-2-(4-(3-(1,3-dioxoisoindolin-2-yl)propyl)-2,2-dimethylpyrrolidin-1-yl)nicotinamide

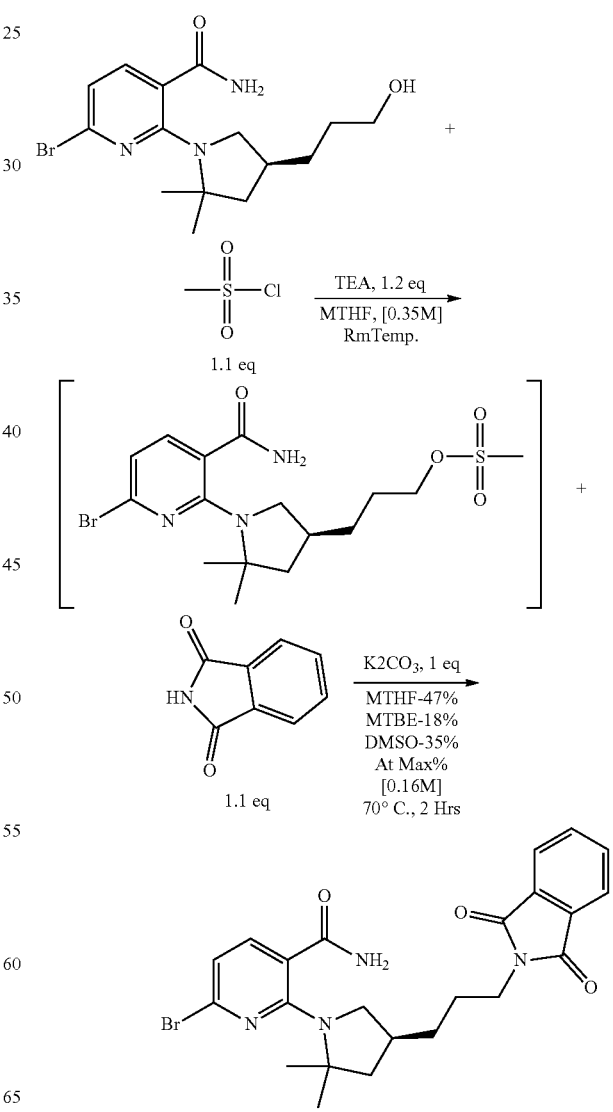

A mixture of (S)-6-bromo-2-(4-(3-hydroxypropyl)-2,2-dimethylpyrrolidin-1-yl)nicotinamide (2.65 kg, 7.4 mol), 2-methyltetrahydrofuran (16 L) and triethylamine (900 g, 8.88 mol) was stirred at 20° C. then methanesulfonyl chloride (933 g, 8.14 mol) was added over 2 h. The mixture was stirred at 20° C. until the reaction was completed (typically 16 h). The resulting mixture as filtered and the filter cake was rinsed with tert-butyl methyl ether (2×4 L). The combined filtrates (containing (S)-3-(1-(6-bromo-3-carbamoylpyridin-2-yl)-5,5-dimethylpyrrolidin-3-yl)propyl methanesulfonate) were transferred to a reactor and diluted with dimethyl sulfoxide (16 L). To the mixture was added phthalimide (1198 g, 8.14 mol). The mixture was stirred until a solution was obtained then potassium carbonate (1023 g, 7.4 mol) was added and the mixture was stirred and heated to 70° C. until the reaction was completed (2 h). The mixture was cooled to 20° C. and diluted with 2-methyltetrahydrofuran (16 L), followed by the addition of deionized water (21 L). The phases were separated and the upper organic phase was washed with deionized water (10 L) and saturated aqueous sodium chloride (2×1 L). The organic phase was diluted with toluene (16 L) and concentrated under reduced pressure to approximately 10 L volume. The solid was isolated by filtration and the filter cake was rinsed with toluene (2×2 L). The resulting solid was dried to afford (S)-6-bromo-2-(4-(3-(1,3-dioxoisoindolin-2-yl)propyl)-2,2-dimethylpyrrolidin-1-yl)nicotinamide as an off-white solid (3393 g, 6.99 mol, 94% yield).

Step 9: Sulfonylation to (S)-6-bromo-2-(4-(3-(1,3-dioxoisoindolin-2-yl)propyl)-2,2-dimethylpyrrolidin-1-yl)-N-((6-fluoropyridin-2-yl)sulfonyl)nicotinamide

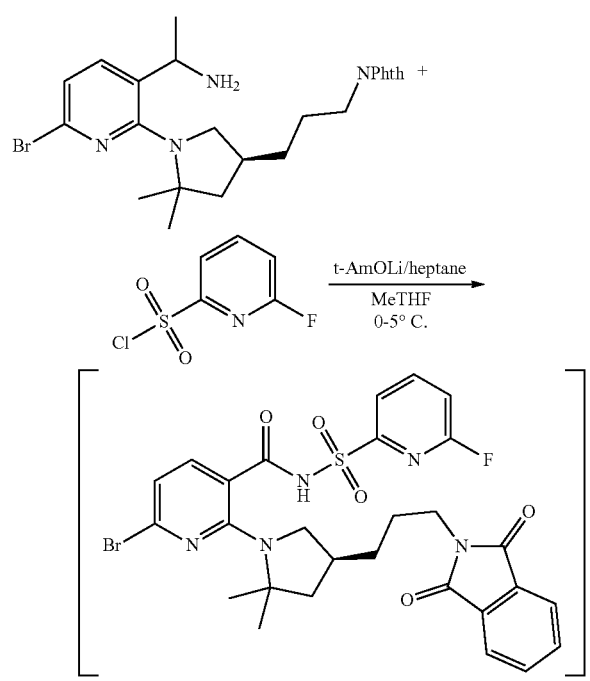

6-fluoropyridine-2-sulfonyl chloride (529 g, 340 mL, 2.71 mol) was added to a solution of (S)-6-bromo-2-(4-(3-(1,3-dioxoisoindolin-2-yl)propyl)-2,2-dimethylpyrrolidin-1-yl)nicotinamide 0.5 PhMe (1.20 kg, 2.26 mol; 91.2% potency) in 2-MeTHF (6.56 L; 6 VolEq) at 0-5° C. then lithium 2-methylbutan-2-olate (t-OAmLi; 1.22 kg of 40% w/w, 1.67 L of 40% w/w, 5.19 mol; 2.3 equiv.) was added while maintaining the reaction temperature between 5-10° C. After the addition was completed, the reaction solution was stirred at 0-10° C. until the reaction was complete (HPLC shows <1% AUC starting material remains). The reaction solution was advanced to the next step without any further processing.

Step 10: Phthalimide Ring-Opening to (S)-2-((3-(1-(6-bromo-3-(((6-fluoropyridin-2-yl)sulfonyl)carbamoyl)pyridin-2-yl)-5,5-dimethylpyrrolidin-3-yl)propyl)carbamoyl)benzoic Acid

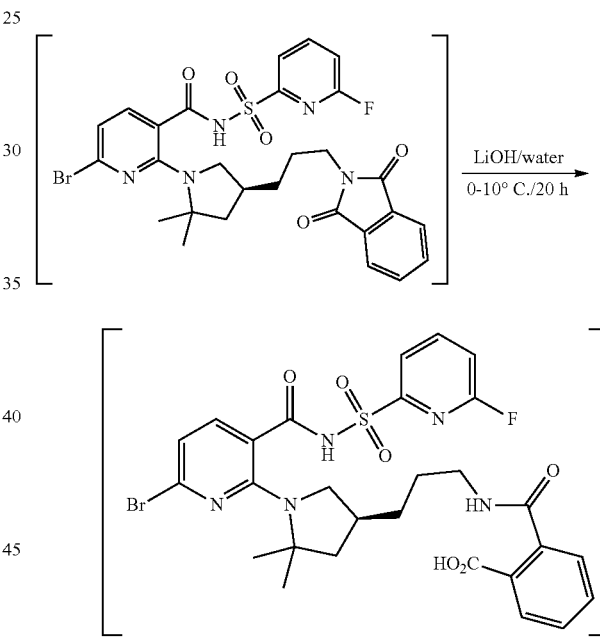

The reaction solution containing (S)-6-bromo-2-(4-(3-(1,3-dioxoisoindolin-2-yl)propyl)-2,2-dimethylpyrrolidin-1-yl)-N-((6-fluoropyridin-2-yl)sulfonyl)nicotinamide from the preceding step was cooled and maintained below 10° C. when a solution of LiOH.H$_2$O (284 g, 6.77 mol; 3 equiv.) in water (2.19 L; 2 VolEq) was added. The biphasic mixture was stirred at 5-15° C. until the reaction was completed (typically 2 h). While maintaining the reaction temperature below 10° C., 2 M HCl (5.64 L, 11.3 mol; 5 equiv.) was added dropwise over ~1 h. The pH of the aqueous phase was about 2. The phases were separated then the organic phase was concentrated to a minimum volume removing most of the MeTHF (40° C./150-70 torr). The reaction mixture was advanced to the next step without any further processing.

Step 11: Phthalimide Deprotection to (S)-2-(4-(3-aminopropyl)-2,2-dimethylpyrrolidin-1-yl)-6-bromo-N-((6-fluoropyridin-2-yl)sulfonyl)nicotinamide

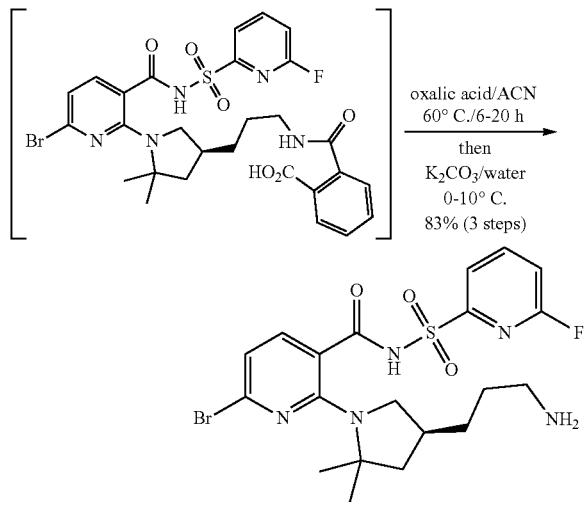

The concentrate containing (S)-2-((3-(1-(6-bromo-3-(((6-fluoropyridin-2-yl)sulfonyl)carbamoyl)pyridin-2-yl)-5,5-dimethylpyrrolidin-3-yl)propyl)carbamoyl)benzoic acid from the preceding step was diluted with CH$_3$CN (6.56 L; 6 VolEq) and water (3.83 L; 2 VolEq) then oxalic acid (508 g, 5.64 mol; 2.5 equiv.) was added and the resultant solution was heated at 60° C. until the reaction was complete (typically at least 4 h). The solution was cooled to 0-10° C. then a solution of K$_2$CO$_3$ (2.18 kg, 15.8 mol; 7 equiv.) in water (3.83 L; 3.5 VolEq) was added drop-wise while maintaining the reaction temperature below 10° C. The solid was collected by filtration. The damp filter-cake was washed consecutively with water (2×2.2 L; 2 VolEq) and then i-PrOH (2×600 mL; 0.5 VolEq), air-dried with suction, and vacuum-dried (50° C./30 torr) to afford (S)-2-(4-(3-aminopropyl)-2,2-dimethylpyrrolidin-1-yl)-6-bromo-N-((6-fluoropyridin-2-yl)sulfonyl)nicotinamide (959 g; 83% for 3 steps; >98% AUC) as a fine, white powder.

$^1$HNMR (400 MHz, DMSO-d$_6$) δ 8.09 (q, J=7.9 Hz, 1H), 7.83 (dd, J=7.5, 2.2 Hz, 1H), 7.67 (s, 3H), 7.39 (d, J=7.6 Hz, 1H), 7.23 (dd, J=8.2, 2.4 Hz, 1H), 6.58 (d, J=7.6 Hz, 1H), 3.20-2.99 (m, 2H), 2.81 (td, J=7.2, 4.7 Hz, 2H), 2.08 (dh, J=15.3, 7.0 Hz, 1H), 1.84 (dd, J=11.8, 5.7 Hz, 1H), 1.54 (q, J=7.6 Hz, 2H), 1.48 (s, 3H), 1.47 (s, 3H), 1.37 (t, J=11.9 Hz, 1H), 1.26 (ddd, J=29.1, 13.8, 7.4 Hz, 2H).

Step 12: Macrocyclization to (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione

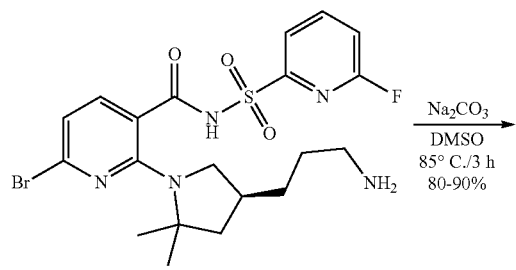

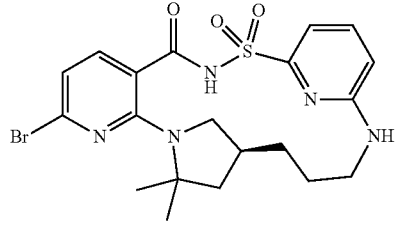

A mixture of (S)-2-(4-(3-aminopropyl)-2,2-dimethylpyrrolidin-1-yl)-6-bromo-N-((6-fluoropyridin-2-yl)sulfonyl)nicotinamide (950 g, 1.85 mol) and Na$_2$CO$_3$ (392 g, 3.69 mol; 2 equiv.) in DMSO (7.60 L; 8 VolEq) was heated at 85° C. until the reaction was completed (~6 h). The suspension was cooled to <15° C. and diluted with MeTHF (19.0 L; 20 VolEq). Water (13.3 L) was added slowly while maintaining the reaction temperature <15° C. While maintaining the reaction temperature <15° C., 2 M HCl (4.62 L, 9.24 mol; 5 equiv.) was added (pH ~2). The phases were separated and the organic phase was washed twice with water (9.50 L; 10 VolEq) containing NaCl (190 g; 2 wt %). The organic phase was concentrated to a minimum volume (45° C./180 torr) and chased with i-PrOAc (2-3×500 mL) to remove the MeTHF. The concentrate was backfilled with i-PrOAc (3.8 L; 4 VolEq) and agitated at 45° C. until crystallization occurred. The suspension was aged with agitation for no longer than 30 min and then allowed to cool to 20° C. After aging at 20° C. for at least 2 h, the solid was collected by filtration. The filter-cake was washed with 1:1 i-PrOAc/MTBE (500-mL), air-dried with suction, and vacuum-dried (40-55° C./<100 torr/N2 bleed) to afford (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione.0.8 i-PrOAc (830 g; 78% yield corrected for i-PrOAc solvate) as a white powder with a slight yellow tint.

A second crop was obtained by concentrating the filtrate to ~400 mL total volume. The mixture was then seeded and aged at 15-20° C. The solid was collected by filtration. The filter-cake was washed successively with 1:1 i-PrOAc/MTBE (200 mL) and MTBE (100 mL), air-dried with suction, and vacuum-dried (55° C./<100 torr/N2 bleed) to afford (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione.0.67 i-PrOAc (113 g; 11% corrected yield) as a pale yellow solid.

$^1$HNMR (400 MHz, Chloroform-d) 69.13 (s, 1H), 7.66 (d, J=7.9 Hz, 1H), 7.54 (dd, J=8.4, 7.3 Hz, 1H), 7.43 (d, J=7.3 Hz, 1H), 6.79 (d, J=7.9 Hz, 1H), 6.56 (d, J=8.4 Hz, 1H), 4.99 (hept, J=6.3 Hz, 1H), 4.57 (d, J=8.8 Hz, 1H), 4.02-3.85 (m, 1H), 3.27-3.09 (m, 2H), 2.96 (t, J=10.2 Hz, 1H), 2.35 (p, J=9.5 Hz, 1H), 2.02 (s, 3H), 1.95 (dd, J=12.1, 6.7 Hz, 1H), 1.72-1.59 (m, 6H), 1.58 (s, 3H), 1.55 (s, 3H), 1.43 (d, J=40.1 Hz, 1H), 1.23 (d, J=6.3 Hz, 5H).

General UPLC/HPLC Analytical Methods

LC method A: Analytical reverse phase UPLC using an Acquity UPLC BEH C$_{18}$ column (50×2.1 mm, 1.7 μm particle) made by Waters (pn: 186002350), and a dual gradient run from 1-99% mobile phase B over 2.9 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C.

LC method B: Merckmillipore Chromolith SpeedROD C$_{18}$ column (50×4.6 mm) and a dual gradient run from 5-100% mobile phase B over 6 minutes. Mobile phase A=water (0.1% CF$_3$CO$_2$H). Mobile phase B=acetonitrile (0.1% CF$_3$CO$_2$H).

LC method C: Merckmillipore Chromolith SpeedROD C$_{18}$ column (50×4.6 mm) and a dual gradient run from 5-100% mobile phase B over 12 minutes. Mobile phase A=water (0.1% CF$_3$CO$_2$H). Mobile phase B=acetonitrile (0.1% CF$_3$CO$_2$H).

LC method D: Acquity UPLC BEH C$_{18}$ column (30×2.1 mm, 1.7 µm particle) made by Waters (pn: 186002349), and a dual gradient run from 1-99% mobile phase B over 1.0 minute. Mobile phase A=H$_2$O (0.05% CF$_3$CO$_2$H). Mobile phase B=CH$_3$CN (0.035% CF$_3$CO$_2$H). Flow rate=1.5 mL/min, injection volume=1.5 µL, and column temperature=60° C.

LC method E: Luna column C$_{18}$ (2) 50×3 mm, 3 µm. run: 2.5 min. Mobile phase: Initial 95% H$_2$O containing 0.1% formic acid/5% MeCN containing 0.1% formic acid, linear gradient to 95% MeCN containing 0.1% formic acid over 1.3 min, hold 1.2 min at 95% MeCN containing 0.1% formic acid. Temperature: 45° C., Flow: 1.5 m/min.

LC method F: SunFire column C$_{18}$ 75×4.6 mm 3.5 µm, run: 6 min. Mobile phase conditions: Initial 95% H$_2$O+0.1% formic acid/5% MeCN+0.1% formic acid, linear gradient to 95% MeCN for 4 min, hold for 2 min at 95% MeCN. T: 45° C., Flow: 1.5 mL/min.

LC method G: Analytical reverse phase UPLC using an Acquity UPLC BEH C$_{18}$ column (50×2.1 mm, 1.7 µm particle) made by Waters (pn: 186002350), and a dual gradient run from 30-99% mobile phase B over 2.9 minutes. Mobile phase A=H$_2$O (0.05% CF$_3$CO$_2$H). Mobile phase B=MeCN (0.035% CF$_3$CO$_2$H). Flow rate=1.2 mL/min, injection volume=1.5 µL, and column temperature=60° C.

LC method H: Water Cortex 2.7p C$_{18}$ (3.0 mm×50 mm) column, Temp: 55° C.; Flow: 1.2 mL/min; Mobile phase: 100% water with 0.1% trifluoroacetic(TFA) acid then 100% acetonitrile with 0.1% TFA acid, gradient 5% to 100% B over 4 min, with stay at 100% B for 0.5 min, equilibration to 5% B over 1.5 min.

LC method I: Reverse phase UPLC using an Acquity UPLC BEH C$_{18}$ column (30×2.1 mm, 1.7 µm particle) made by Waters (pn: 186002349), and a dual gradient run from 30-99% mobile phase B over 1.0 minutes. Mobile phase A=H$_2$O (0.05% CF$_3$CO$_2$H). Mobile phase B=CH$_3$CN (0.035% CF$_3$CO$_2$H). Flow rate=1.5 mL/min, injection volume=1.5 µL, and column temperature=60° C.

LC method J: SunFire C$_{18}$ 4.6×75 mm, 5 µM, 6 min run, 50-95% ACN/Water (0.1% FA modifier), 1.5 min equilibration, gradient over 3 min, hold 3 min. 1.5 mL/min.

LC method K: SunFire C$_{18}$ 75×4.6 mm 3.5 µm, run: 6 min. Mobile phase conditions: Initial 95% H$_2$O+0.1% Formic acid/5% CH$_3$CN+0.1% FA, linear gradient to 95% CH$_3$CN for 4 min, hold for 2 min at 95% CH$_3$CN. T: 45° C., Flow:1.5 mL/min LC method L: Luna C$_{18}$ 3.0×50 mm 3.0 µM, temp: 45° C., Flow: 2.0 mL/min, run time: 3 minutes. Mobile phase: Initial 95% H$_2$O (0.1% formic acid) and 5% CH$_3$CN (0.1% formic acid) linear gradient to 95% CH$_3$CN (0.1% formic acid) for 2.0 min then hold at 95% CH$_3$CN (0.1% formic acid) for 1.0 min.

LC method M: Analytical reverse phase UPLC using an Acquity UPLC BEH C$_{18}$ column (50×2.1 mm, 1.7 µm particle) made by Waters (pn: 186002350), and a dual gradient run from 1-99% mobile phase B over 5.0 minutes. Mobile phase A=water (0.05% trifluoroacetic acid). Mobile phase B=acetonitrile (0.035% trifluoroacetic acid). Flow rate=1.2 mL/min, injection volume=1.5 µL, and column temperature=60° C.

LC method N: Analytical reverse phase UPLC using an Acquity UPLC BEH C$_{18}$ column (30×2.1 mm, 1.7 µm particle) made by Waters (pn: 186002349), and a dual gradient run from 1-99% mobile phase B over 1.2 minutes. Mobile phase A=water (0.05% trifluoroacetic acid). Mobile phase B=acetonitrile (0.035% trifluoroacetic acid). Flow rate=1.5 mL/min, injection volume=1.5 µL, and column temperature=60° C.

Example 3: Preparation of (14S)-8-[3-(tert-butyldimethylsilyl)-1H-pyrazol-1-yl]-12,12-dimethyl-2λ$^6$-thia-3,9,11,18,23-pentaazatetracyclo[17.3.1.1 11, 14.0 5,10]tetracosa-1(23),5(10),6,8,19,21-hexaene-2, 2,4-trione, Compound (1-5)

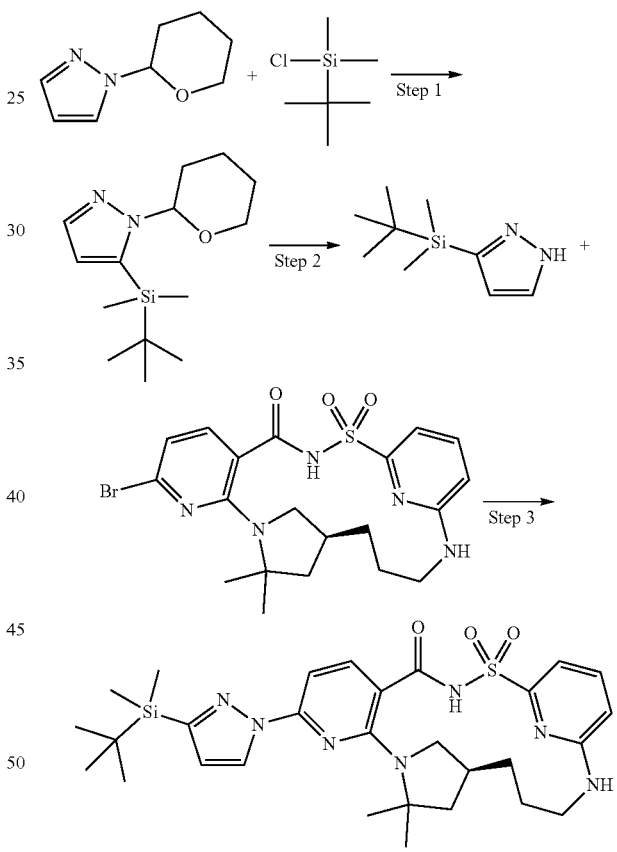

Step 1: tert-Butyl-dimethyl-(2-tetrahydropyran-2-ylpyrazol-3-yl)silane

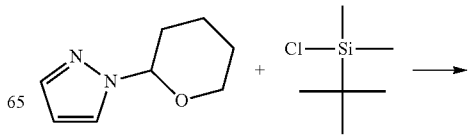

-continued

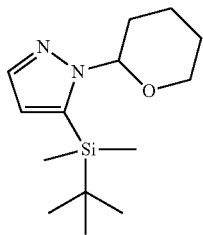

1-Tetrahydropyran-2-ylpyrazole (5.065 g, 33.28 mmol) was dissolved in THF (30 mL) and cooled to −35° C. n-Butyl lithium (16 mL of 2.5 M solution in hexanes, 40.00 mmol) was added dropwise and the solution was stirred for an additional 1 h at −35° C. A solution of tert-butyl-chloro-dimethyl-silane (5.1 g, 33.84 mmol) in THF (7 mL) was added dropwise and the reaction was allowed to warm to room temperature and stir for 3 h. At this point, a saturated ammonium chloride solution was added until pH was ~7 and the mixture was extracted with ether. The organics were separated, washed with brine, dried over magnesium sulfate and evaporated to give tert-butyl-dimethyl-(2-tetrahydropyran-2-ylpyrazol-3-yl)silane (8.41 g, 95%) as an orange oil. $^1$HNMR (400 MHz, DMSO-$d_6$) δ 7.53 (d, J=1.6 Hz, 1H), 6.43 (d, J=1.7 Hz, 1H), 5.23 (dd, J=10.1, 2.4 Hz, 1H), 3.96-3.85 (m, 1H), 3.63-3.48 (m, 1H), 2.43-2.29 (m, 1H), 2.02-1.92 (m, 1H), 1.84-1.75 (m, 1H), 1.73-1.56 (m, 1H), 1.56-1.47 (m, 2H), 0.88 (s, 9H), 0.32 (s, 3H), 0.30 (s, 3H). ESI-MS m/z calc. 266.18143, found 267.3 (M+1)$^+$; Retention time: 0.79 minutes (LC method D).

Step 2: tert-Butyl-dimethyl-(1H-pyrazol-3-yl)silane

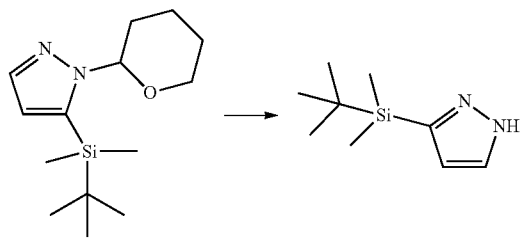 [SMILES: CC(C)(C)[Si](C)(C)c1ccnn1C1CCCCO1 ; CC(C)(C)[Si](C)(C)c1cc[nH]n1]

tert-Butyl-dimethyl-(2-tetrahydropyran-2-ylpyrazol-3-yl) silane (8.4 g, 31.53 mmol) was dissolved in a mixture of aqueous 6M HCl (16 mL 96.00 mmol), ethanol (8 mL) and heated at 50° C. for 3 h. A saturated aqueous NaHCO$_3$ solution was added to quench the acid, and the resulting solution was extracted with ethyl acetate two times. The organics were combined, washed with brine, dried over magnesium sulfate and evaporated. The crude material was purified by silica gel chromatography eluting with 0-100% ethyl acetate in hexanes to give tert-butyl-dimethyl-(1H-pyrazol-3-yl)silane (3.85 g, 67%) as a white solid. $^1$HNMR (400 MHz, DMSO-$d_6$) δ 12.77 (s, 1H), 7.52 (s, 1H), 6.40 (d, J=1.6 Hz, 1H), 0.85 (s, 9H), 0.25 (s, 6H). ESI-MS m/z calc. 182.12393, found 183.6 (M+1)$^+$; Retention time: 0.57 minutes (LC method D).

Step 3: (14S)-8-[3-(tert-butyldimethylsilyl)-1H-pyrazol-1-yl]-12,12-dimethyl-2λ$^6$-thia-3,9,11,18,23-pentaazatetracyclo[17.3.1.111,14.05,10]tetracosa-1(23),5(10),6,8,19,21-hexaene-2,2,4-trione, Compound (1-5)

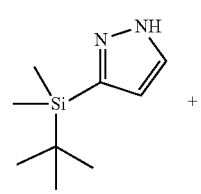

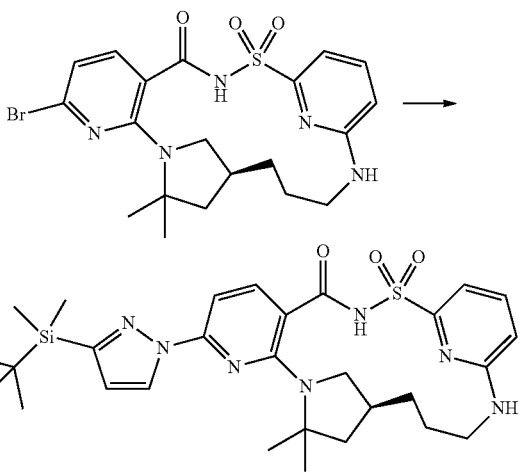

To a solution of (14S)-8-bromo-12,12-dimethyl-2λ$^6$-thia-3,9,11,18,23-pentaazatetracyclo[17.3.1.111,14.05,10]tetracosa-1(23),5(10),6,8,19,21-hexaene-2,2,4-trione (75 mg, 0.1259 mmol) and tert-butyl-dimethyl-(1H-pyrazol-3-yl)silane (27 mg, 0.1481 mmol) in butyl acetate (1 mL) and DMSO (0.3 mL) was added potassium carbonate (46 mg, 0.3328 mmol). N2 was bubbled in for 5 min. (1R,2R)—N1,N2-dimethylcyclohexane-1,2-diamine (10.800 mg, 12 μL, 0.0759 mmol) and CuI (2.3 mg, 0.0121 mmol) were added, the tube was sealed and the reaction warmed at 120° C. for 5.5 h. The reaction was cooled down to room temperature and the mixture was filtered over diatomaceous earth, eluting with MeTHF (10 mL). DMSO was added (0.5 mL) and the volatiles were removed under vacuum. The crude mixture was purified by reverse phase chromatography using a 12 g C18 Agela cartridge, eluting with a gradient of MeCN in 0.1% formic acid aqueous solution (5% for 2 CV then 70% to 100% in 15 CV). Afforded after lyophilization (14S)-8-[3-(tert-butyldimethylsilyl)-1H-pyrazol-1-yl]-12,12-dimethyl-2λ$^6$-thia-3,9,11,18,23-pentaazatetracyclo[17.3.1.111,14.05,10]tetracosa-1(23),5(10),6,8,19,21-hexaene-2,2,4-trione as a white solid (38 mg, 49%). $^1$HNMR (400 MHz, DMSO-$d_6$) δ 12.52 (br. s, 1H), 8.41 (d, J=2.4 Hz, 1H), 7.86 (d, J=8.3 Hz, 1H), 7.58 (t, J=7.9 Hz, 1H), 7.16 (d, J=8.3 Hz, 1H), 7.06 (d, J=7.1 Hz, 1H), 6.98 (br. s., 1H), 6.71 (d, J=8.6 Hz, 1H), 6.69 (d, J=2.4 Hz, 1H), 4.02-3.84 (m, 1H), 3.17 (br. s, 1H), 2.95 (d, J=13.2 Hz, 1H), 2.82-2.63 (m, 1H), 2.13 (br. s., 1H), 1.87 (dd, J=11.4, 5.0 Hz, 1H), 1.82-1.71 (m, 1H), 1.65-1.55 (m, 6H), 1.53 (s, 3H), 1.32 (q, J=11.7 Hz, 1H), 0.94 (s, 9H), 0.27 (d, J=1.5 Hz, 6H). ESI-MS m/z calc. 595.2761, found 596.3 (M+1)$^+$; Retention time: 4.26 minutes (LC method J).

Example 4: Preparation of (14S)-8-{3-[(tert-butyldi-methylsilyl)methoxy]-1H-pyrazol-1-yl}-12,12-dimethyl-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione, Compound (1-2)

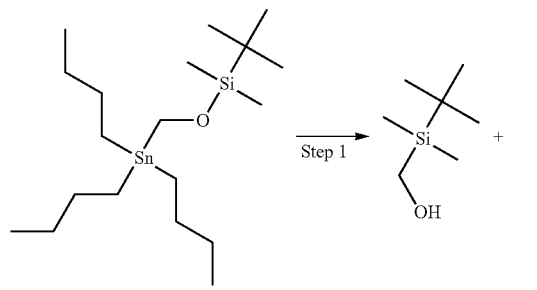

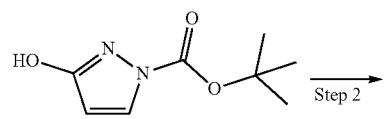

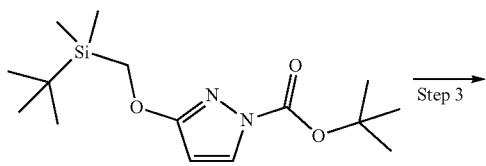

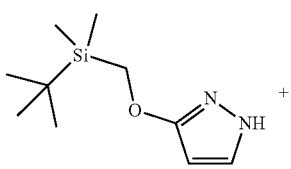

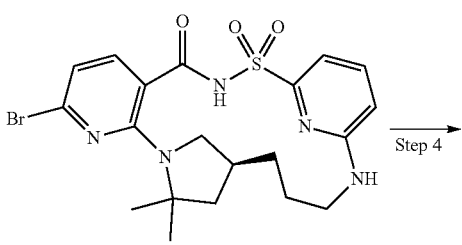

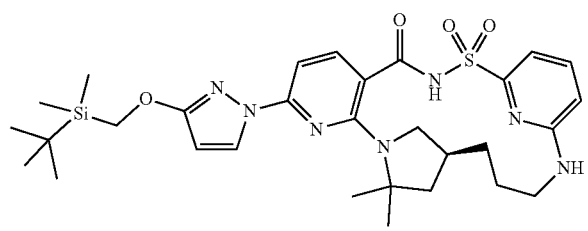 [SMILES: CC1(C)C[C@@H]2CCCNc3cccc(n3)S(=O)(=O)NC(=O)c3ccc(-n4ccc(OC[Si](C)(C)C5(C(F)(F)F)CC5)n4)nc3N1C2]

Step 1: [tert-Butyl(dimethyl)silyl]methanol

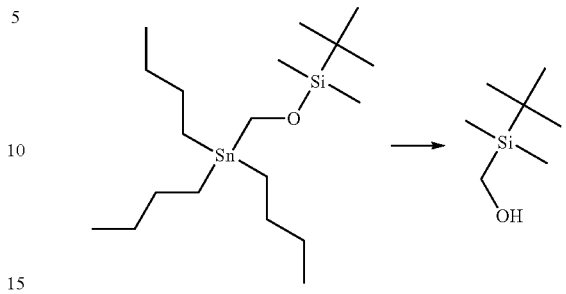

In a heat gun-dried round-bottom flask under nitrogen, n-butyl lithium (1 mL, 1.600 mmol, 1.6 M solution in hexanes) was combined with N,N,N',N'-tetramethylethane-1,2-diamine (200 μL, 1.325 mmol) in anhydrous THF (8 mL) at 0° C. in an ice-water bath. tert-Butyl-dimethyl-(tributylstannylmethoxy)silane (500 mg, 1.149 mmol) was then added dropwise by syringe over 1 minute. The reaction mixture was stirred for 2 minutes at 0° C. then quenched with acetic acid (200 μL, 3.517 mmol). The reaction mixture was then diluted with a saturated aqueous solution of sodium bicarbonate (10 mL), water (10 mL) and ethyl acetate (15 mL) and warmed to room temperature. The layers were separated and the aqueous phase was extracted by an additional 2×15 mL ethyl acetate. The combined organics were washed with brine, dried over sodium sulfate, and concentrated to give a colorless oil. This crude material was purified by chromatography on silica gel (1-70% ethyl acetate in hexanes gradient, with an initial hexane flush) to give as a white solid, [tert-butyl(dimethyl)silyl]methanol (95 mg, 57%). ¹HNMR (400 MHz, Chloroform-d) δ 3.46 (s, 2H), 0.90 (s, 9H), 0.00 (s, 6H). (alcohol OH not visible)

Step 2: tert-Butyl 3-[[tert-butyl(dimethyl)silyl]methoxy]pyrazole-1-carboxylate

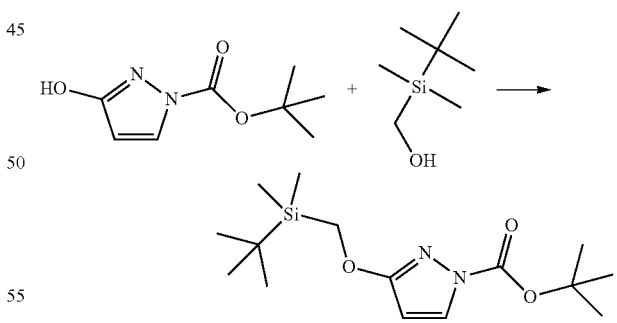

tert-Butyl 3-hydroxypyrazole-1-carboxylate (220 mg, 1.194 mmol), [tert-butyl(dimethyl)silyl]methanol (190 mg, 1.299 mmol), and triphenylphosphine (345 mg, 1.315 mmol) were combined in THF (2.5 mL) and cooled to 0° C. DIAD (255 μL, 1.317 mmol) was added dropwise and the reaction mixture was warmed to room temperature for 16 hours. The reaction mixture was then partitioned between 30 mL 1M NaOH (aq) and ethyl acetate (30 mL). The layers were separated and the aqueous phase was extracted with an additional 2×30 mL ethyl acetate. The combined organics were washed with brine, dried over sodium sulfate and concentrated. The resulting crude material was purified by flash chromatography on silica gel, eluting with a gradient of 0-50% ethyl acetate in hexanes (initially very shallow, compound eluted just before 10%) to give as a colorless oil, tert-butyl 3-[[tert-butyl(dimethyl) silyl]methoxy]pyrazole-1-carboxylate (242 mg, 65%). $^1$HNMR (400 MHz, Chloroform-d) δ 7.81 (d, J=2.7 Hz, 1H), 5.85 (d, J=2.8 Hz, 1H), 4.06 (s, 2H), 1.61 (s, 9H), 0.94 (s, 9H), 0.06 (s, 6H). ESI-MS m/z calc. 312.18692, found 313.3 (M+1)$^+$; Retention time: 0.88 minutes (LC method D).

Step 3: tert-Butyl-dimethyl-(1H-pyrazol-3-yloxymethyl)silane

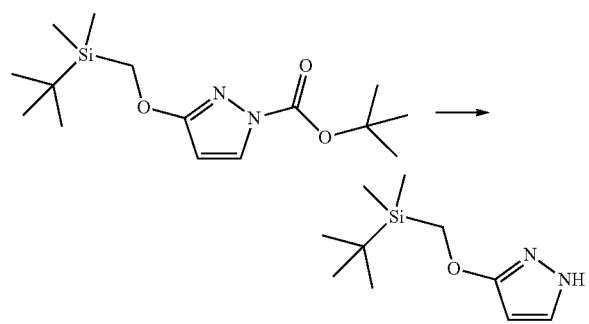

tert-Butyl 3-[[tert-butyl(dimethyl)silyl]methoxy]pyrazole-1-carboxylate (242 mg, 0.7744 mmol) was combined in DCM (2.5 mL) with TFA (750 μL, 9.735 mmol) at room temperature and stirred for 15 minutes. The reaction mixture was then evaporated under reduced pressure. The crude material was dissolved in 15 mL ethyl acetate and washed with 15 mL of saturated aqueous sodium bicarbonate. The aqueous layer was extracted with an additional 2×10 mL ethyl acetate, and the combined organics were washed with brine, dried over sodium sulfate, and concentrated to give a colorless oil, tert-Butyl-dimethyl-(1H-pyrazol-3-yloxymethyl)silane (161 mg, 98%). $^1$HNMR (400 MHz, Chloroform-d) δ 7.35 (d, J=2.4 Hz, 1H), 5.73 (d, J=2.5 Hz, 1H), 3.92 (s, 2H), 0.95 (s, 9H), 0.08 (s, 6H) (NH not visible). ESI-MS m/z calc. 212.13449, found 213.6 (M+1)$^+$; Retention time: 0.66 minutes (LC method D).

Step 4: (14S)-8-{3-[(tert-butyldimethylsilyl) methoxy]-1H-pyrazol-1-yl}-12,12-dimethyl-2λ$^6$-thia-3,9,11,18,23-pentaazatetracyclo[17.3.1.1$^{11,14}$.0$^{5,10}$]tetracosa-1(23),5(10),6,8,19,21-hexaene-2, 2,4-trione, Compound (1-2)

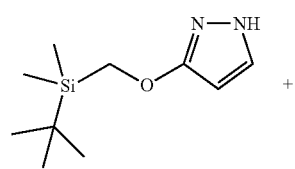

Copper(I) iodide (7 mg, 0.0368 mmol) was added to a degassed solution of (14S)-8-bromo-12,12-dimethyl-2λ$^6$-thia-3,9,11,18,23-pentaazatetracyclo[17.3.1.1$^{11,14}$.0$^{5,10}$] tetracosa-1(23),5(10),6,8,19,21-hexaene-2,2,4-trione (230 mg, 0.3861 mmol), tert-butyl-dimethyl-(1H-pyrazol-3-yloxymethyl)silane (100 mg, 0.4709 mmol), (1R,2R)—N1, N2-dimethylcyclohexane-1,2-diamine (31.500 mg, 35 μL, 0.2215 mmol) and potassium carbonate (120 mg, 0.8683 mmol) in butyl acetate (3 mL) and dimethyl sulfoxide (0.9 mL). The reaction mixture was warmed at 120° C. for 6 hours. The reaction was cooled down to room temperature and the mixture was filtered over Celite, eluting with Me-THF (20 mL). The filtrate was washed with water (25 mL) and brine (3×25 mL). The organic phase was dried over sodium sulfate, filtered and concentrated to dryness. The crude product was purified by normal phase chromatography (10+12 g SiO$_2$, eluting 20 to 100% ethyl acetate in hexanes) and by reverse phase chromatography on C18 (30 g, eluting 50 to 100% acetonitrile in water) and freeze-dried to give (14S)-8-{3-[(tert-butyldimethylsilyl)methoxy]-1H-pyrazol-1-yl}-12,12-dimethyl-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (103 mg, 43%) as a white solid. $^1$HNMR (400 MHz, DMSO-d$_6$) δ 12.48 (br. s., 1H), 8.20 (d, J=2.7 Hz, 1H), 7.81 (d, J=8.3 Hz, 1H), 7.57 (t, J=7.8 Hz, 1H), 7.05 (d, J=7.1 Hz, 1H), 7.02-6.86 (m, 2H), 6.71 (d, J=8.6 Hz, 1H), 6.12 (d, J=2.7 Hz, 1H), 4.03 (s, 2H), 3.93-3.90 (m, 1H), 3.19-3.13 (m, 1H), 2.95-2.93 (m, 1H), 2.76-2.65 (m, 1H), 2.18-2.07 (m, 1H), 1.87-1.83 (m, 1H), 1.76-1.70 (m, 1H), 1.66-1.45 (m, 9H), 1.37-1.23 (m, 1H), 0.94 (s, 9H), 0.07 (s, 6H). ESI-MS m/z calc. 625.2867, found 626.3 (M+1)$^+$; Retention time: 5.49 minutes (LC method K).

Example 5: Preparation of (14S)-8-{3-[(3,3-dimethylbutyl)dimethylsilyl]-1H-pyrazol-1-yl}-12,12-dimethyl-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione, Compound (1-4)

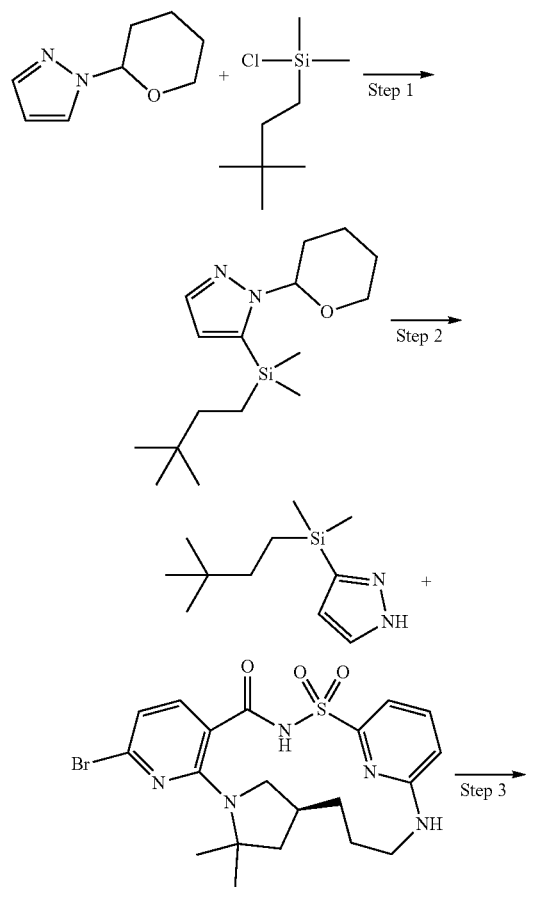

Step 1: 3,3-dimethylbutyl-dimethyl-(2-tetrahydropyran-2-ylpyrazol-3-yl)silane

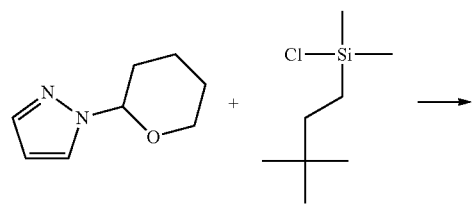

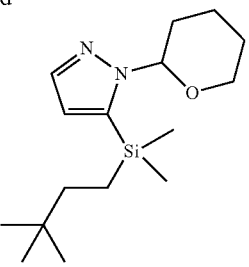

To a stirred solution of 1-tetrahydropyran-2-ylpyrazole (3 g, 19.71 mmol) in anhydrous tetrahydrofuran (25 mL) was added n-butyllitium (1.6 M in hexanes) (15 mL, 24.00 mmol) dropwise from a dropping funnel over 6 min at −35° C. under nitrogen. After the addition was complete, the resulting solution was stirred for an additional 1 h at −35° C. Then a solution of chloro-(3,3-dimethylbutyl)-dimethyl-silane (3.90 g, 21.82 mmol) in anhydrous tetrahydrofuran (1 mL) was added dropwise from the dropping funnel over 5 min. After the end of the addition, the reaction was stirred for an additional 10 min at that temperature, and then the bath was removed and allowed to warm to room temperature. Then after stirring for another 3 h, saturated ammonium chloride solution (30 mL) was added and the mixture was extracted with ether (3×30 mL). The combined organics were washed with brine (20 mL), dried over sodium sulfate, filtered and concentrated under reduced pressure. The crude material (light orange light oil), 3,3-dimethylbutyl-dimethyl-(2-tetrahydropyran-2-ylpyrazol-3-yl)silane (5.79 g, 100%), was used in the subsequent step without further purification. ¹HNMR (400 MHz, Chloroform-d) δ 7.57 (d, J=1.7 Hz, 1H), 6.39 (d, J=1.7 Hz, 1H), 5.29 (dd, J=9.8, 2.6 Hz, 1H), 4.08-3.98 (m, 1H), 3.62 (td, J=11.2, 2.6 Hz, 1H), 2.57-2.42 (m, 1H), 2.13-2.07 (m, 1H), 2.03-1.96 (m, 1H), 1.77-1.63 (m, 2H), 1.61-1.56 (m, 1H), 1.19-1.12 (m, 2H), 0.85 (s, 9H), 0.76-0.70 (m, 2H), 0.30 (s, 6H). ESI-MS m/z calc. 294.21274, found 295.2 (M+1)⁺; Retention time: 2.21 minutes (LC method A).

Step 2: 3,3-dimethylbutyl-dimethyl-(1H-pyrazol-3-yl)silane

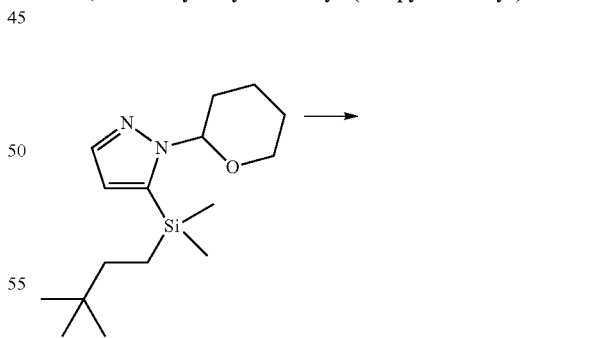

To a stirred solution of 3,3-dimethylbutyl-dimethyl-(2-tetrahydropyran-2-ylpyrazol-3-yl)silane (5.2 g, 17.66 mmol) in ethanol (15 mL) was added aqueous hydrochloric acid (11 mL of 5.0 M, 55.00 mmol) and stirred at 50° C. for 4 h. The reaction was allowed to cool to ambient temperature and a saturated aq. NaHCO$_3$solution was added slowly (vigorous CO$_2$ gas evolution) to quench the acid, and the resulting solution was extracted with ethyl acetate (3×30 mL). The combined organics were washed with brine (20 mL), dried over sodium sulfate, filtered and concentrated under reduced pressure. The crude material (thick oil) upon standing at ambient temperature became a brownish solid that was 3,3-dimethylbutyl-dimethyl-(1H-pyrazol-3-yl)silane (3.64 g, 98%). It was used in the subsequent reaction without further purification. $^1$HNMR (400 MHz, Methanol-d4) δ 8.18 (d, J=2.4 Hz, 1H), 6.84 (d, J=2.4 Hz, 1H), 1.22-1.15 (m, 2H), 0.87 (s, 9H), 0.86-0.79 (m, 2H), 0.39 (s, 6H). ESI-MS m/z calc. 210.15523, found 211.1 (M+1)$^+$; Retention time: 1.66 minutes (LC method A).

Step 3: (14S)-8-{3-[(3,3-dimethylbutyl)dimethylsilyl]-1H-pyrazol-1-yl}-12,12-dimethyl-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione, Compound (1-4)

{3-[(3,3-dimethylbutyl)dimethylsilyl]-1H-pyrazol-1-yl}-12,12-dimethyl-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (33 mg, 31%) as a white solid. $^1$HNMR (400 MHz, DMSO-d$_6$) δ 12.55 (br. s., 1H), 8.40 (d, J=2.4 Hz, 1H), 7.86 (d, J=8.3 Hz, 1H), 7.58 (t, J=7.8 Hz, 1H), 7.15 (d, J=8.1 Hz, 1H), 7.06 (d, J=7.3 Hz, 1H), 6.99-6.97 (m, 1H), 6.71 (d, J=8.6 Hz, 1H), 6.68 (d, J=2.4 Hz, 1H), 3.97-3.88 (m, 1H), 3.20-3.15 (m, 1H), 2.95 (d, J=13.0 Hz, 1H), 2.74-2.66 (m, 1H), 2.18-2.07 (m, 1H), 1.89-1.85 (m, 1H), 1.81-1.71 (m, 1H), 1.67-1.49 (m, 9H), 1.39-1.27 (m, 1H), 1.25-1.18 (m, 2H), 0.84 (s, 9H), 0.73-0.66 (m, 2H), 0.27 (s, 6H). ESI-MS m/z calc. 623.3074, found 624.3 (M+1)$^+$; Retention time: 4.47 minutes. (LC method J).

Example 6: Preparation of: (14S)-12,12-dimethyl-8-{3-[(trimethylsilyl)methoxy]-1H-pyrazol-1-yl}-2λ$^6$-thia-3,9,11,18,23-pentaazatetracyclo[17.3.1.1$^{11,14}$.0$^{5,10}$]tetracosa-1(22),5(10),6,8,19(23),20-hexaene-2,2,4-trione, Compound (1-8)

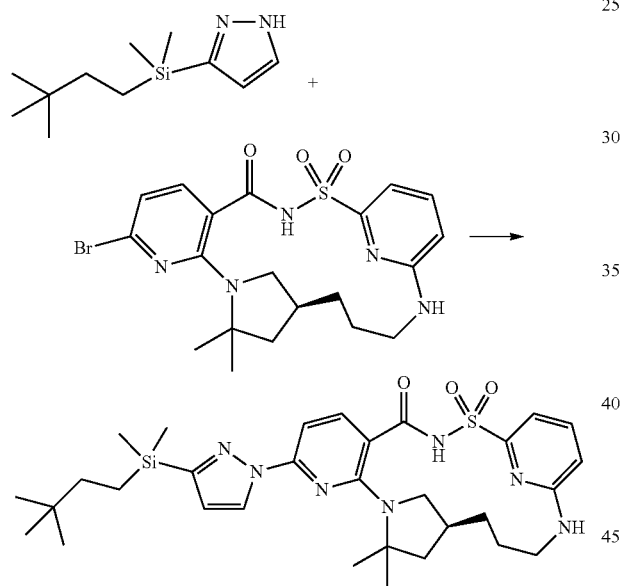

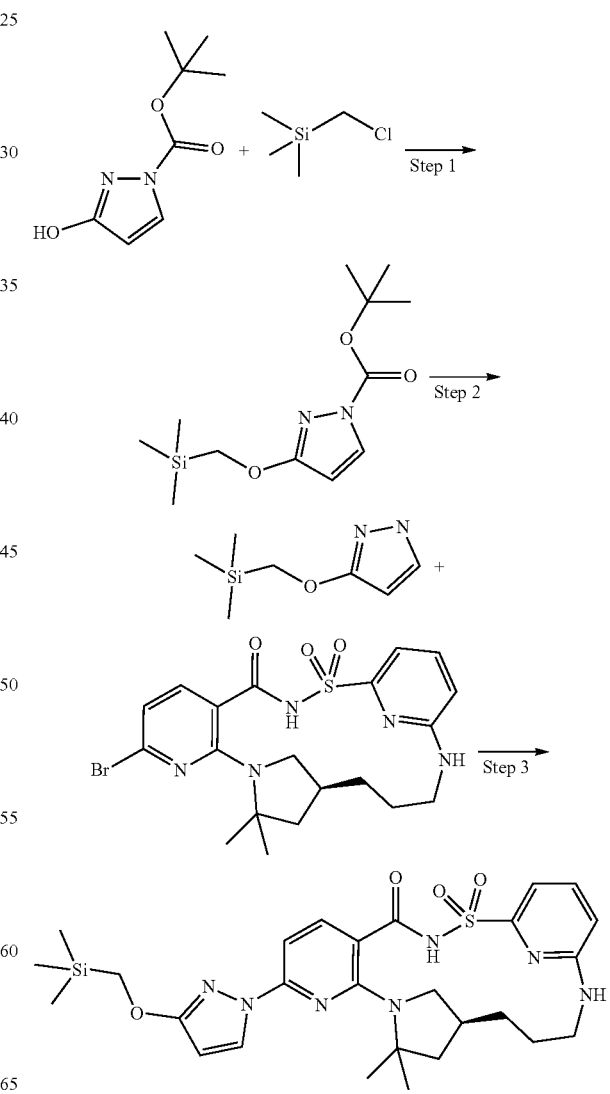

In a sealed tube, (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (100 mg, 0.1679 mmol), 3,3-dimethylbutyl-dimethyl-(1H-pyrazol-3-yl)silane (39 mg, 0.1854 mmol), copper(I) iodide (3 mg, 0.0158 mmol), potassium carbonate (52 mg, 0.3762 mmol) and (1R,2R)—N1,N2-dimethylcyclohexane-1,2-diamine (12.600 mg, 14 μL, 0.0886 mmol) were mixed in butyl acetate (0.7 mL) and dimethyl sulfoxide (0.2 mL). The mixture was degassed using 3 cycles of vacuum/nitrogen backfilling. The reaction was stirred at 120° C. for 5 hours. The reaction was cooled down to room temperature and the mixture was filtered over diatomaceous earth, eluting with MeTHF (10 mL). DMSO was added (0.5 mL) and the volatiles were removed under vacuum. The crude mixture was purified by reverse phase chromatography using a 12 g C18 Agela cartridge, eluting with a gradient of MeCN in 0.1% formic acid aqueous solution (5% for 2 CV then 50% to 100% in 15 CV). Afforded after lyophilization (14S)-8-

Step 1: tert-Butyl 3-(trimethylsilylmethoxy)pyrazole-1-carboxylate

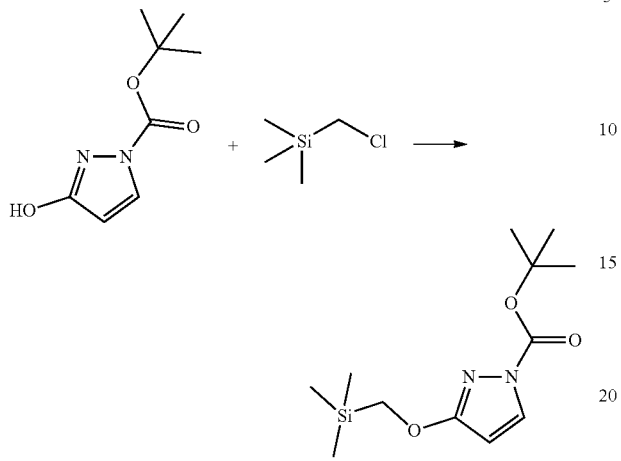

A 5 mL microwave vial was charged with tert-butyl 3-hydroxypyrazole-1-carboxylate (2 g, 10.86 mmol), chloromethyl(trimethyl)silane (1.6 mL, 11.46 mmol), potassium carbonate (3.00 g, 21.71 mmol) and DMA (20 mL). The reaction was heated at 120° C. for 16 hours. The reaction was diluted with water (50 mL) and ethyl acetate (50 mL). After separation of the two layers, the aqueous layer was extracted with ethyl acetate (2×50 mL). The combined organic layers were washed with brine (3×50 mL), dried over anhydrous sodium sulfate and concentrated under vacuum. The residue was dissolved in THF (20 mL). TEA (4.6 mL, 33.00 mmol) and Boc$_2$O (4.75 g, 21.764 mmol) were added to the reaction mixture, followed by a catalytic amount of DMAP (157 mg, 1.285 mmol). The reaction was stirred at rt for 16 hours. All the volatiles were removed under vacuum. The residue was purified by silica gel chromatography using 0 to 10% diethyl ether in hexane to furnish tert-butyl 3-(trimethylsilylmethoxy)pyrazole-1-carboxylate (2.146 g, 72%) as a clear oil. $^1$HNMR (250 MHz, Chloroform-d) δ 7.82 (d, J=2.9 Hz, 1H), 5.86 (d, J=2.9 Hz, 1H), 3.98 (s, 2H), 1.61 (s, 9H), 0.11 (s, 9H). ESI-MS m/z calc. 270.14, found 270.9 (M+1)$^+$; Retention time: 6.62 minutes (LC method C).

Step 2: Trimethyl(1H-pyrazol-3-yloxymethyl)silane

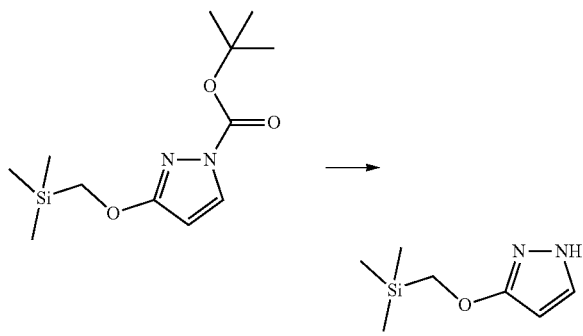

Into a solution of tert-butyl 3-(trimethylsilylmethoxy)pyrazole-1-carboxylate (2.146 g, 7.78 mmol) in DCM (24 mL) was added TFA (12 mL, 155.76 mmol). The reaction was stirred at rt for 2 hours. All the volatiles were removed under vacuum to furnish trimethyl(1H-pyrazol-3-yloxymethyl)silane (trifluoroacetate salt) (3.03 g, 100%) as a clear oil. $^1$HNMR (250 MHz, Chloroform-d) δ 7.72 (d, J=2.9 Hz, 1H), 5.95 (d, J=2.9 Hz, 1H), 3.92 (s, 2H), 0.17 (s, 9H). ESI-MS m/z calc. 170.0875, found 171.3 (M+1)$^+$; Retention time: 3.85 minutes (LC method C).

Step 3: (14S)-12,12-dimethyl-8-{3-[(trimethylsilyl)methoxy]-1H-pyrazol-1-yl}-2λ$^6$-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione, Compound (1-8)

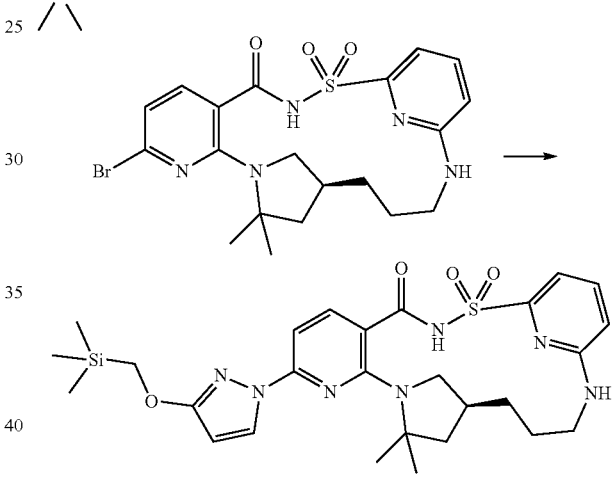

To a solution of trimethyl(1H-pyrazol-3-yloxymethyl)silane (56 mg, 0.3289 mmol), (14S)-8-bromo-12,12-dimethyl-2λ$^6$-thia-3,9,11,18,23-pentaazatetracyclo[17.3.1.1¹¹,14.0⁵,¹⁰]tetracosa-1(23),5(10),6,8,19,21-hexaene-2,2,4-trione (150 mg, 0.2518 mmol), L-proline (12 mg, 0.1042 mmol), and K$_2$CO$_3$ (105 mg, 0.7597 mmol) in DMSO (1 mL) was added CuI (10 mg, 0.0525 mmol). The solution was cycled with vacuum/N$_2$ 3 times, then sealed and heated at 110° C. for 18 h. The reaction was diluted into 10 mL water, aqueous 2M HCl was added until the pH was acidic, and the reaction was extracted with DCM (3×20 mL). The combined organic layers were washed with brine (2×20 mL), dried over Na$_2$SO$_4$, and concentrated under reduced pressure. Column chromatography (silica, 12 g) eluting with 10-50% acetone in hexanes followed by reverse phase HPLC using 0 to 100% acetonitrile in water (buffered with 0.1% TFA) yields (14S)-12,12-dimethyl-8-{3-[(trimethylsilyl)methoxy]-1H-pyrazol-1-yl}-2λ$^6$-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (28.1 mg, 19%) as a white solid. $^1$HNMR (500 MHz, DMSO-d$_6$) δ 12.50 (s, 1H), 8.21 (d, J=2.8 Hz, 1H), 7.82 (d, J=8.2 Hz, 1H), 7.58 (dd, J=8.5, 7.2 Hz, 1H), 7.06 (d, J=7.3 Hz, 1H), 6.99 (d, J=8.8 Hz, 1H), 6.94 (d, J=8.2 Hz, 1H), 6.72 (dd, J=8.5, 0.8 Hz, 1H), 6.13 (d, J=2.7 Hz, 1H), 3.96 (s, 3H), 3.16 (s, 1H), 3.00-2.90 (m, 1H), 2.77-2.63 (m, 1H), 2.13 (s, 1H), 1.91-1.83 (m, 1H), 1.83-1.70 (m, 1H), 1.62-1.51 (m, 9H), 1.39-1.26 (m, 1H), 0.12 (s, 9H). ESI-MS m/z calc. 583.2397, found 584.2 (M+1)⁺; Retention time: 3.33 minutes (LC method H).

Example 7: Preparation of (14S)-12,12-dimethyl-8-{3-[2-(trimethylsilyl)ethoxy]-1H-pyrazol-1-yl}-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione, Compound (1-7)

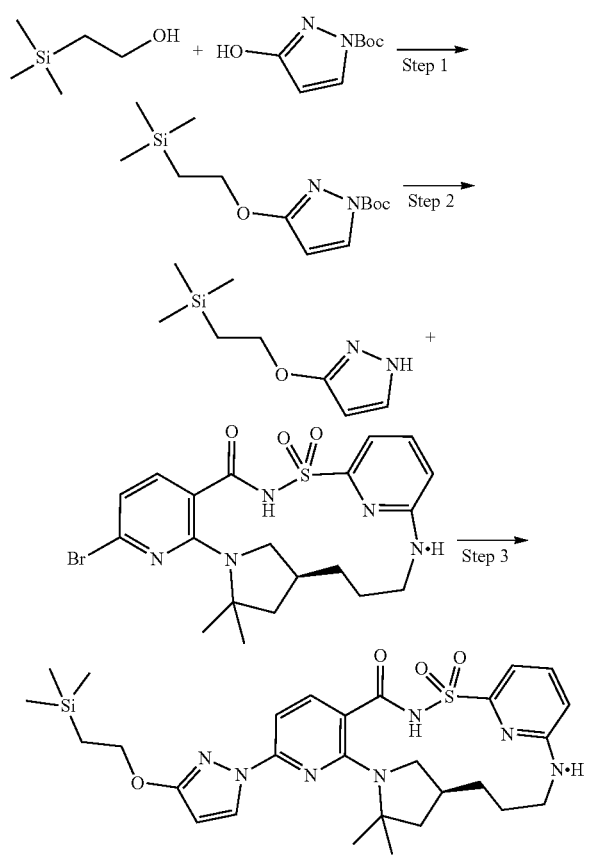

Step 1: tert-Butyl 3-(2-trimethylsilylethoxy)pyrazole-1-carboxylate

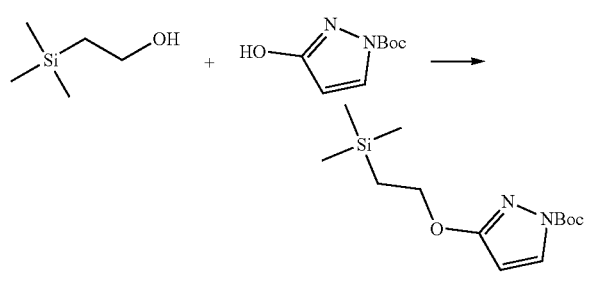

Into a solution of tert-butyl 3-hydroxypyrazole-1-carboxylate (5.01 g, 27.20 mmol) and triphenylphosphine (14.3 g, 54.52 mmol) in anhydrous THF (50 mL) was added DIAD (10.5 mL, 54.21 mmol) at 0° C. The reaction was stirred at rt overnight. The reaction was concentrated under vacuum to remove most of THF. The residue was diluted with ethyl acetate (300 mL), and washed with brine (100 mL). The organic layer was dried over anhydrous sodium sulfate and concentrated under vacuum. The residue was suspended in a 20% diethyl ether in hexane solution (400 mL). The solid was filtered off. The filtrate was concentrated under vacuum and purified by silica gel chromatography using 0 to 10% ethyl acetate in hexane to furnish tert-butyl 3-(2-trimethylsilylethoxy)pyrazole-1-carboxylate (4.559 g, 59%) as a clear oil. ESI-MS m/z calc. 284.1556, found 285.1 (M+1)⁺; Retention time: 6.7 minutes (LC method C).

Step 2: Trimethyl-[2-(1H-pyrazol-3-yloxy)ethyl]silane

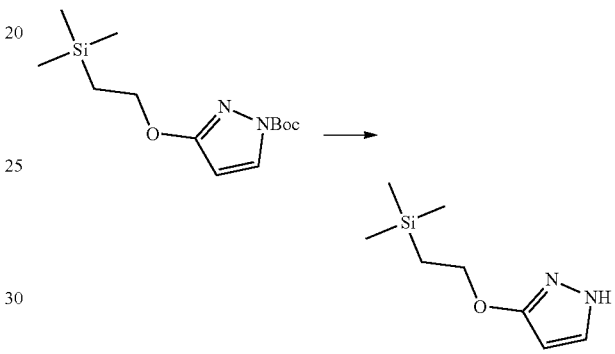

Into a solution of tert-butyl 3-(2-trimethylsilylethoxy)pyrazole-1-carboxylate (4.076 g, 14.33 mmol) in a solvent mixture of THF (29 mL) and EtOH (58 mL) was added an aqueous solution of NaOH (14.5 mL of 2 M, 29.00 mmol). The reaction was stirred at rt for 3 hours. The reaction was diluted with water (100 mL), and extracted with ethyl acetate (3×100 mL). The combined organic layers were washed with brine (100 mL), dried over anhydrous sodium sulfate and concentrated under vacuum to furnish trimethyl-[2-(1H-pyrazol-3-yloxy)ethyl]silane (2.919 g, 99%) as a clear oil. The product was used in the next step without purification. ¹HNMR (250 MHz, Chloroform-d) δ 7.36 (d, J=1.7 Hz, 1H), 5.72 (d, J=1.8 Hz, 1H), 4.35-4.14 (m, 2H), 1.21-1.03 (m, 2H), 0.06 (s, 9H). ESI-MS m/z calc. 184.1032, found 185.4 (M+1)⁺; Retention time: 4.44 minutes (LC method C).

Step 3: (14S)-12,12-dimethyl-8-{3-[2-(trimethylsilyl)ethoxy]-1H-pyrazol-1-yl}-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione, Compound(1-7)

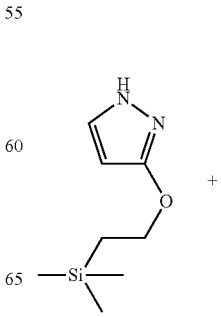

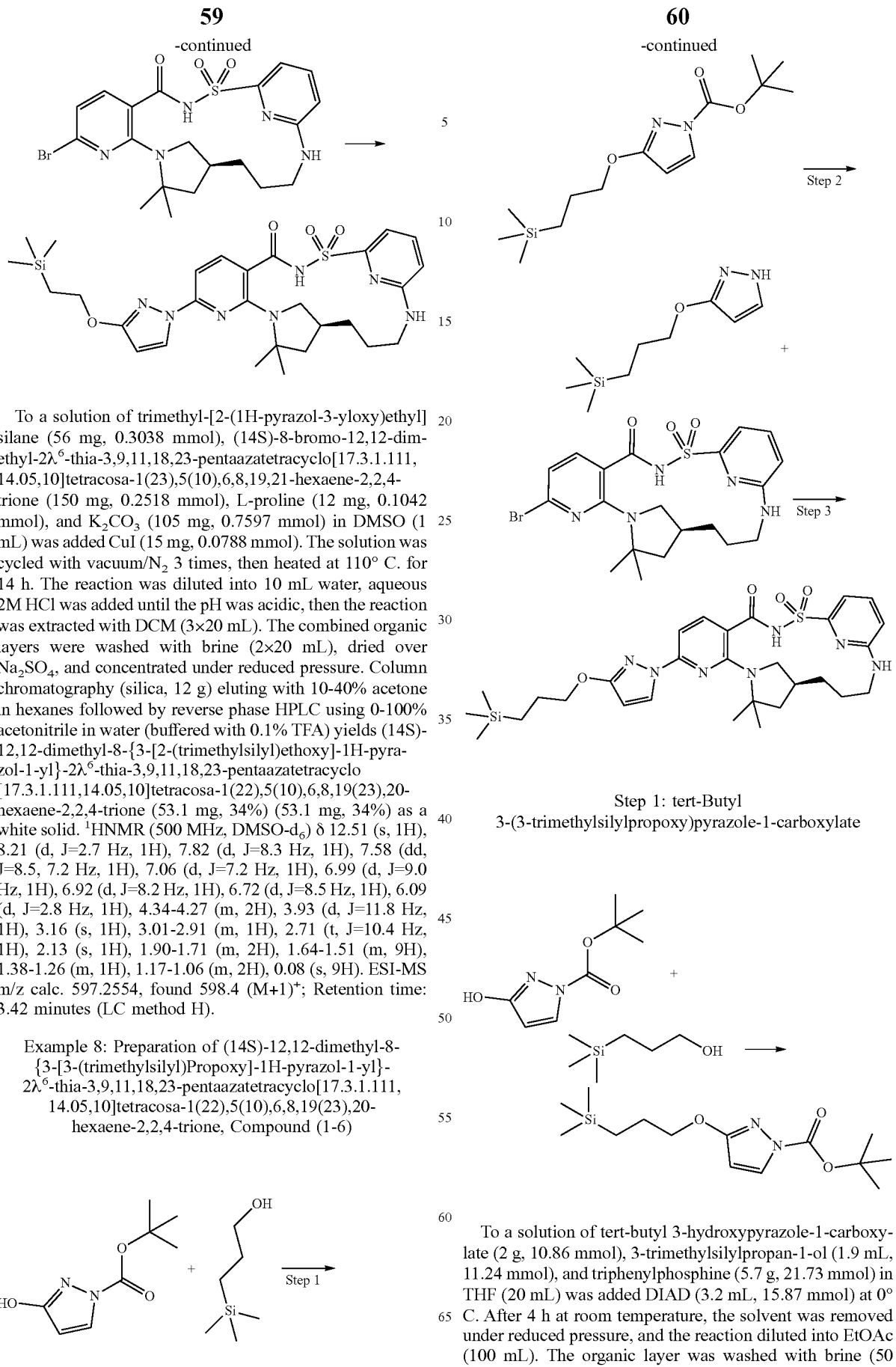

To a solution of trimethyl-[2-(1H-pyrazol-3-yloxy)ethyl]silane (56 mg, 0.3038 mmol), (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (150 mg, 0.2518 mmol), L-proline (12 mg, 0.1042 mmol), and K₂CO₃ (105 mg, 0.7597 mmol) in DMSO (1 mL) was added CuI (15 mg, 0.0788 mmol). The solution was cycled with vacuum/N₂ 3 times, then heated at 110° C. for 14 h. The reaction was diluted into 10 mL water, aqueous 2M HCl was added until the pH was acidic, then the reaction was extracted with DCM (3×20 mL). The combined organic layers were washed with brine (2×20 mL), dried over Na₂SO₄, and concentrated under reduced pressure. Column chromatography (silica, 12 g) eluting with 10-40% acetone in hexanes followed by reverse phase HPLC using 0-100% acetonitrile in water (buffered with 0.1% TFA) yields (14S)-12,12-dimethyl-8-{3-[2-(trimethylsilyl)ethoxy]-1H-pyrazol-1-yl}-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (53.1 mg, 34%) (53.1 mg, 34%) as a white solid. ¹HNMR (500 MHz, DMSO-d₆) δ 12.51 (s, 1H), 8.21 (d, J=2.7 Hz, 1H), 7.82 (d, J=8.3 Hz, 1H), 7.58 (dd, J=8.5, 7.2 Hz, 1H), 7.06 (d, J=7.2 Hz, 1H), 6.99 (d, J=9.0 Hz, 1H), 6.92 (d, J=8.2 Hz, 1H), 6.72 (d, J=8.5 Hz, 1H), 6.09 (d, J=2.8 Hz, 1H), 4.34-4.27 (m, 2H), 3.93 (d, J=11.8 Hz, 1H), 3.16 (s, 1H), 3.01-2.91 (m, 1H), 2.71 (t, J=10.4 Hz, 1H), 2.13 (s, 1H), 1.90-1.71 (m, 2H), 1.64-1.51 (m, 9H), 1.38-1.26 (m, 1H), 1.17-1.06 (m, 2H), 0.08 (s, 9H). ESI-MS m/z calc. 597.2554, found 598.4 (M+1)⁺; Retention time: 3.42 minutes (LC method H).

Example 8: Preparation of (14S)-12,12-dimethyl-8-{3-[3-(trimethylsilyl)Propoxy]-1H-pyrazol-1-yl}-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione, Compound (1-6)

Step 1: tert-Butyl 3-(3-trimethylsilylpropoxy)pyrazole-1-carboxylate

To a solution of tert-butyl 3-hydroxypyrazole-1-carboxylate (2 g, 10.86 mmol), 3-trimethylsilylpropan-1-ol (1.9 mL, 11.24 mmol), and triphenylphosphine (5.7 g, 21.73 mmol) in THF (20 mL) was added DIAD (3.2 mL, 15.87 mmol) at 0° C. After 4 h at room temperature, the solvent was removed under reduced pressure, and the reaction diluted into EtOAc (100 mL). The organic layer was washed with brine (50 mL), dried over Na$_2$SO$_4$, and concentrated under reduced pressure. The crude was then suspended in 10:1 hexanes: Et$_2$O (v:v) (150 mL) and filtered. The solvent was removed from the supernatant under reduced pressure. Column chromatography (silica, 120 g) eluting with 0-10% EtOAc in hexanes yielded tert-butyl 3-(3-trimethylsilyl propoxy)pyrazole-1-carboxylate (3.3 g, 53%) as a clear oil. $^1$HNMR (250 MHz, CDCl$_3$) δ 7.83 (d, J=3.0 Hz, 1H), 5.86 (d, J=3.0 Hz, 1H), 4.24 (t, J=6.9 Hz, 2H), 1.84-1.67 (m, 2H), 1.62 (s, 9H), 0.71-0.46 (m, 2H), 0.01 (s, 9H). ESI-MS m/z calc. 298.1713, found 299.3 (M+1)$^+$; Retention time: 4.02 minutes (LC method B).

Step 2: Trimethyl-[3-(1H-pyrazol-3-yloxy)propyl]silane

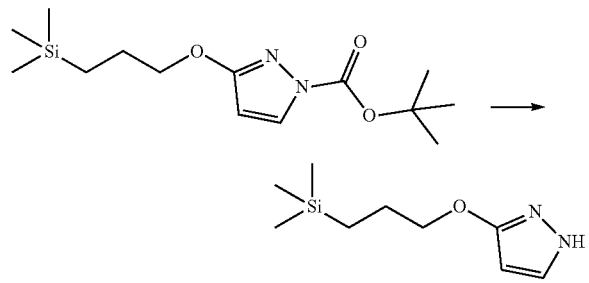

To a solution of tert-butyl 3-(3-trimethylsilylpropoxy)pyrazole-1-carboxylate (3.1 g, 5.67 mmol) in THF (25 mL) and EtOH (50 mL) was added aqueous NaOH (10.5 mL of 2 M, 21.00 mmol) at room temperature. The reaction was stirred at room temperature for 4 h, then diluted into water (100 mL), and extracted with EtOAc (3×100 mL). The organic portions were washed with brine (100 mL), dried over Na$_2$SO$_4$, filtered and concentrated under reduced pressure. Column chromatography (silica, 120 g) eluting with 10-50% EtOAc in hexanes yielded trimethyl-[3-(1H-pyrazol-3-yloxy)propyl]silane (877 mg, 77%) as a clear liquid. $^1$HNMR (250 MHz, CDCl$_3$) δ 7.36 (d, J=2.4 Hz, 1H), 5.91-5.52 (m, 1H), 4.24-3.92 (m, 2H), 1.76 (m, 2H), 0.71-0.44 (m, 2H), 0.18--0.19 (m, 9H). ESI-MS m/z calc. 198.1188, found 199.3 (M+1)$^+$; Retention time: 2.94 minutes (LC method B).

Step 3: (14S)-12,12-dimethyl-8-{3-[3-(trimethylsilyl)propoxy]-1H-pyrazol-1-yl}-2λ$^6$-thia-3,9,11,18,23-pentaazatetracyclo[17.3.1.1$^{11,14}$.0$^{5,10}$]tetracosa-1(22),5(10),6,8,19(23),20-hexaene-2,2,4-trione, Compound (1-6)

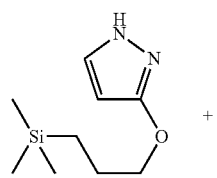

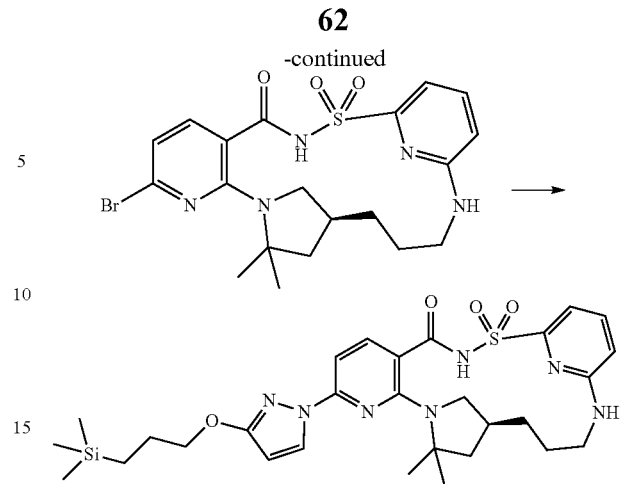

To a solution of trimethyl-[3-(1H-pyrazol-3-yloxy)propyl]silane (50 mg, 0.2521 mmol), (14S)-8-bromo-12,12-dimethyl-2λ$^6$-thia-3,9,11,18,23-pentaazatetracyclo [17.3.1.1$^{11,14}$.0$^{5,10}$]tetracosa-1(23),5(10),6,8,19,21-hexaene-2,2,4-trione (150 mg, 0.2518 mmol), L-proline (7 mg, 0.0608 mmol), and K$_2$CO$_3$ (106 mg, 0.7670 mmol in DMSO (2 mL) was added CuI (7 mg, 0.0368 mmol). The solution was bubbled with nitrogen for 30 min, then heated at 100° C. for 24 h. The reaction was diluted into 10 mL water, and 2M HCl was added until the pH was acidic, and the reaction was extracted with DCM (3×20 mL). The combined organic layers were washed with brine (2×20 mL), dried over Na$_2$SO$_4$, and concentrated under reduced pressure. Column chromatography (silica, 12 g) eluting with 20-50% acetone in hexanes, followed by reverse phase HPLC using 0 to 100% acetonitrile in water (buffered with 0.1% TFA) yields (14S)-12,12-dimethyl-8-{3-[3-(trimethylsilyl)propoxy]-1H-pyrazol-1-yl}-2λ$^6$-thia-3,9,11,18,23-pentaazatetracyclo[17.3.1.1$^{11,14}$.0$^{5,10}$]tetracosa-1(22),5(10),6,8,19(23),20-hexaene-2,2,4-trione (12.4 mg, 8%) (12.4 mg, 8%) as a white solid. $^1$HNMR (500 MHz, DMSO-d$_6$) δ 12.52 (s, 1H), 8.21 (d, J=2.8 Hz, 1H), 7.82 (d, J=8.3 Hz, 1H), 7.58 (dd, J=8.5, 7.2 Hz, 1H), 7.06 (d, J=7.1 Hz, 1H), 6.99 (d, J=8.2 Hz, 1H), 6.92 (d, J=8.3 Hz, 1H), 6.72 (d, J=8.4 Hz, 1H), 6.11 (d, J=2.7 Hz, 1H), 4.16 (t, J=6.8 Hz, 2H), 3.93 (d, J=11.8 Hz, 1H), 3.15 (s, 1H), 2.96 (d, J=13.3 Hz, 1H), 2.77-2.65 (m, 1H), 2.11 (d, J=23.4 Hz, 1H), 1.90-1.83 (m, 1H), 1.80-1.69 (m, 3H), 1.64-1.49 (m, 9H), 1.39-1.25 (m, 1H), 0.63-0.56 (m, 2H) 0.02 (s, 9H). ESI-MS m/z calc. 611.271, found 612.5 (M+1)+; Retention time: 3.55 minutes (LC method H).

Example 9: Preparation of (14S)-12,12-dimethyl-8-{3-[(trimethylgermyl)methoxy]-1H-pyrazol-1-yl}-2λ$^6$-thia-3,9,11,18,23-pentaazatetracyclo[17.3.1.1$^{11}$,$^{14}$.0$^{5,10}$]tetracosa-1(23),5(10),6,8,19,21-hexaene-2,2,4-trione, Compound (2-1)

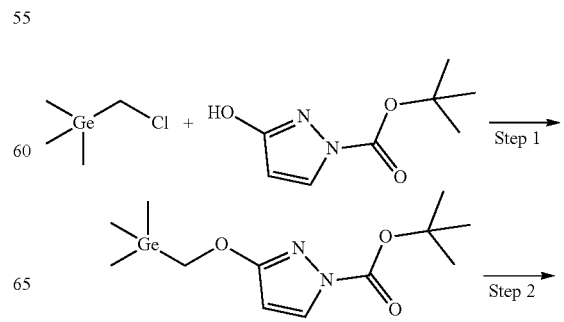

Step 2: Trimethyl(1H-pyrazol-3-yloxymethyl)germane

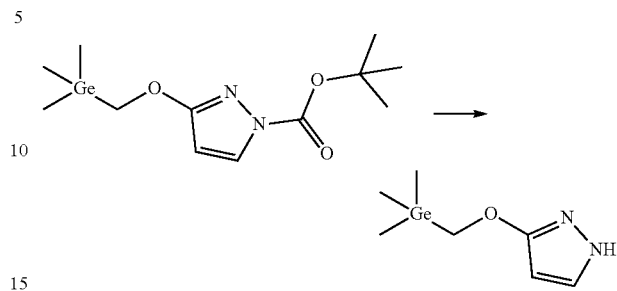

Into a solution of tert-butyl 3-(trimethylgermylmethoxy)pyrazole-1-carboxylate (2.56 g, 7.97 mmol) in DCM (25 mL) was added TFA (12.5 mL). The reaction was stirred at rt for 1 hour. All the volatiles were removed and EtOAc was added. The resulting mixture was then washed once with saturated aqueous NaHCO$_3$, dried over sodium sulfate, filtered and concentrated to afford crude trimethyl(1H-pyrazol-3-yloxymethyl)germane (1.7 g, 94%) as a yellow oil which was used directly in the next step. $^1$HNMR (250 MHz, CDCl$_3$) δ 7.35 (d, J=2.4 Hz, 1H), 5.73 (d, J=2.5 Hz, 1H), 4.06 (s, 2H), 0.25 (s, 9H).

Step 3: (14S)-12,12-dimethyl-8-{3-[(trimethylgermyl)methoxy]-1H-pyrazol-1-yl}-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione, Compound (2-1)

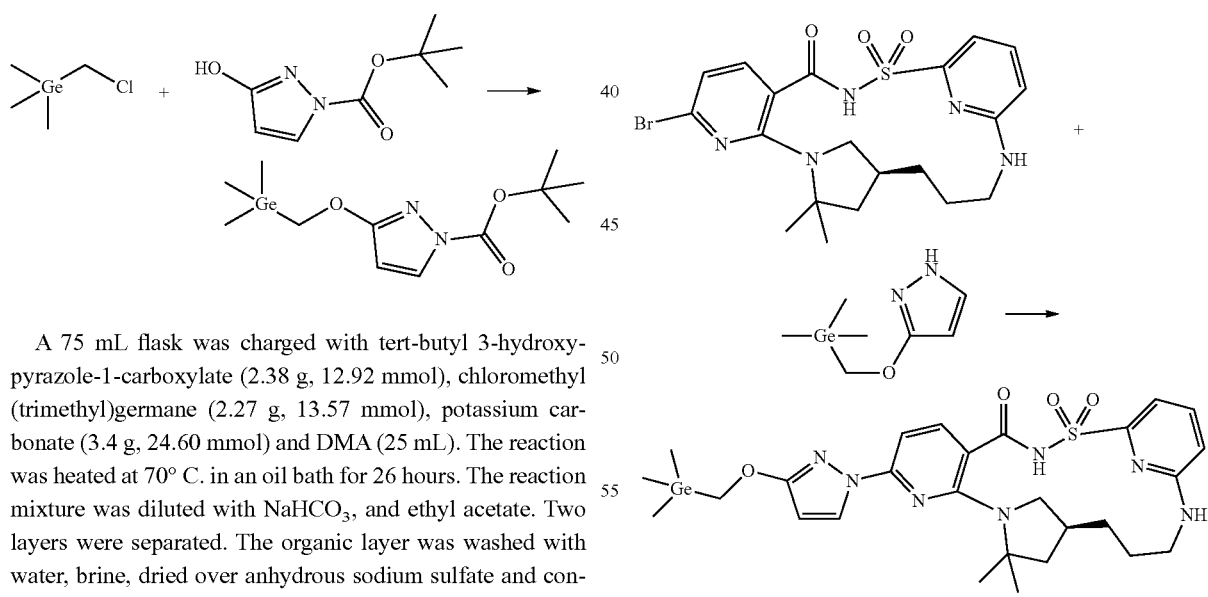

CuI (4.3 mg, 0.0226 mmol) was added to a degassed solution of (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (140 mg, 0.2350 mmol), trimethyl(1H-pyrazol-3-yloxymethyl)germane (61 mg, 0.2839 mmol), (1R,2R)—N1,N2-dimethylcyclohexane-1,2-diamine (19.800 mg, 22 μL, 0.1392 mmol) and potas-

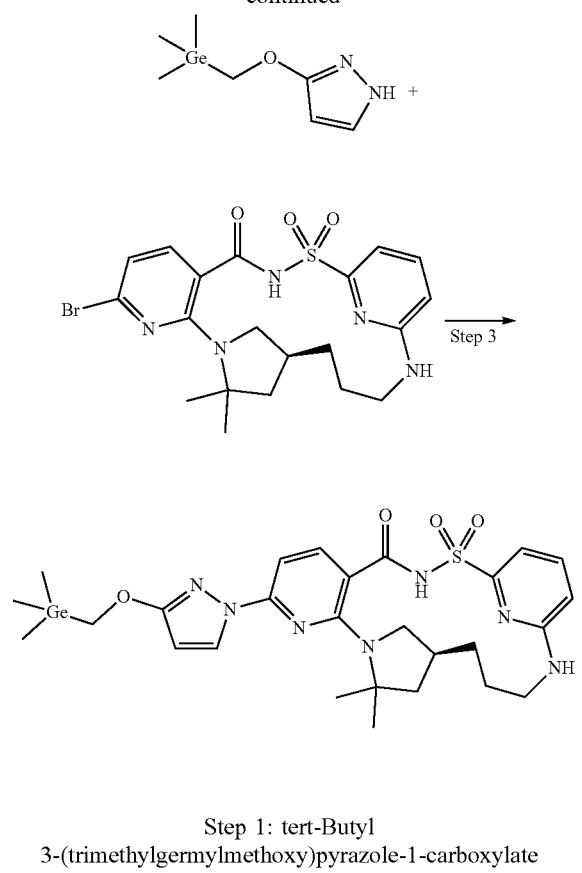

Step 1: tert-Butyl 3-(trimethylgermylmethoxy)pyrazole-1-carboxylate

A 75 mL flask was charged with tert-butyl 3-hydroxypyrazole-1-carboxylate (2.38 g, 12.92 mmol), chloromethyl(trimethyl)germane (2.27 g, 13.57 mmol), potassium carbonate (3.4 g, 24.60 mmol) and DMA (25 mL). The reaction was heated at 70° C. in an oil bath for 26 hours. The reaction mixture was diluted with NaHCO$_3$, and ethyl acetate. Two layers were separated. The organic layer was washed with water, brine, dried over anhydrous sodium sulfate and concentrated to give a crude material which was purified by chromatography to afford tert-butyl 3-(trimethylgermylmethoxy)pyrazole-1-carboxylate (2.57 g, 62%) as a clear oil. $^1$HNMR (250 MHz, CDCl$_3$) δ 7.83 (d, J=3.0 Hz, 1H), 5.85 (d, J=3.1 Hz, 1H), 4.20 (s, 2H), 1.61 (s, 9H), 0.23 (s, 9H). ESI-MS m/z calc. 316.0842, found 317.0 (M+1)$^+$; Retention time: 3.33 minutes (LC method B).

sium carbonate (86 mg, 0.6223 mmol) in butyl acetate (1.9 mL) and DMSO (0.56 mL). The reaction mixture was warmed at 120° C. for 6 hours. The reaction was cooled down to room temperature and the mixture was filtered over Celite, eluting with MeTHF (20 mL). The filtrate was washed with water (25 mL) and brine (3×25 mL). The organic phase was dried over sodium sulfate, filtered and concentrated to dryness. The crude product was purified by normal phase chromatography (10+12 g SiO$_2$, eluting 20 to 100% ethyl acetate in hexanes) and by reverse phase chromatography on C18 (30 g, eluting 50 to 100% acetonitrile in water) and freeze-dried to give (14S)-12,12-dimethyl-8-{3-[(trimethylgermyl)methoxy]-1H-pyrazol-1-yl}-2λ-thia-3,9,11,18,23-pentaazatetracyclo[17.3.1.111,14.05,10]tetracosa-1(23),5(10),6,8,19,21-hexaene-2,2,4-trione (67.3 mg, 46%) as a white fluffy solid. $^1$HNMR (400 MHz, DMSO-d$_6$) δ 12.48 (br. s., 1H), 8.20 (d, J=2.7 Hz, 1H), 7.81 (d, J=8.1 Hz, 1H), 7.57 (t, J=7.9 Hz, 1H), 7.05 (d, J=7.1 Hz, 1H), 7.02-6.95 (m, 1H), 6.93 (d, J=8.3 Hz, 1H), 6.71 (d, J=8.6 Hz, 1H), 6.10 (d, J=2.7 Hz, 1H), 4.22-4.14 (m, 2H), 3.99-3.85 (m, 1H), 3.22-3.10 (m, 1H), 2.95 (d, J=13.0 Hz, 1H), 2.78-2.65 (m, 1H), 2.13 (br. s., 1H), 1.86 (dd, J=11.6, 5.0 Hz, 1H), 1.82-1.69 (m, 1H), 1.66-1.53 (m, 6H), 1.51 (s, 3H), 1.38-1.25 (m, 1H), 0.23 (s, 9H). ESI-MS m/z calc. 629.184, found 630.2 (M+1)+; Retention time: 3.75 minutes (LC method J).

Example 10: Preparation of (14S)-8-[3-({dimethyl[1-(trifluoromethyl)cyclopropyl]silyl}methoxy)-1H-pyrazol-1-yl]-12,12-dimethyl-2λ$^6$-thia-3,9,11,18,23-pentaazatetracyclo[17.3.1.111,14.05,10]tetracosa-1(22),5(10),6,8,19(23),20-hexaene-2,2,4-trione, Compound (1-1)

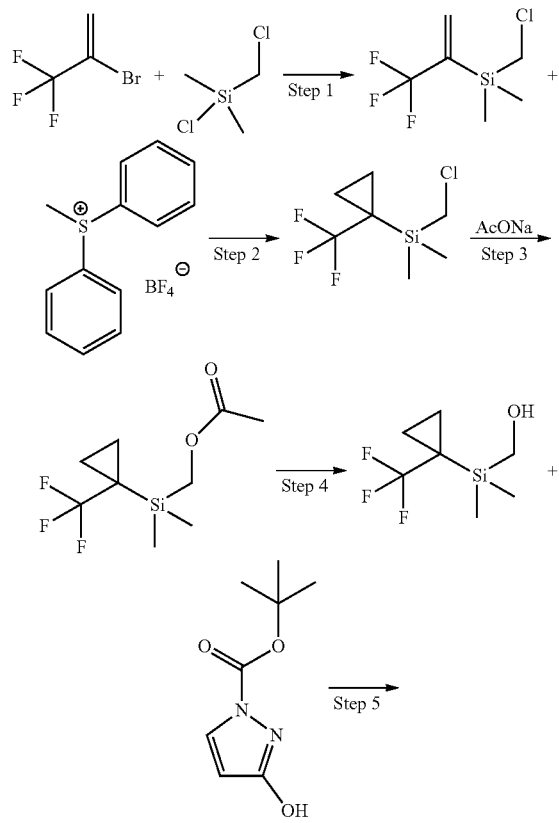

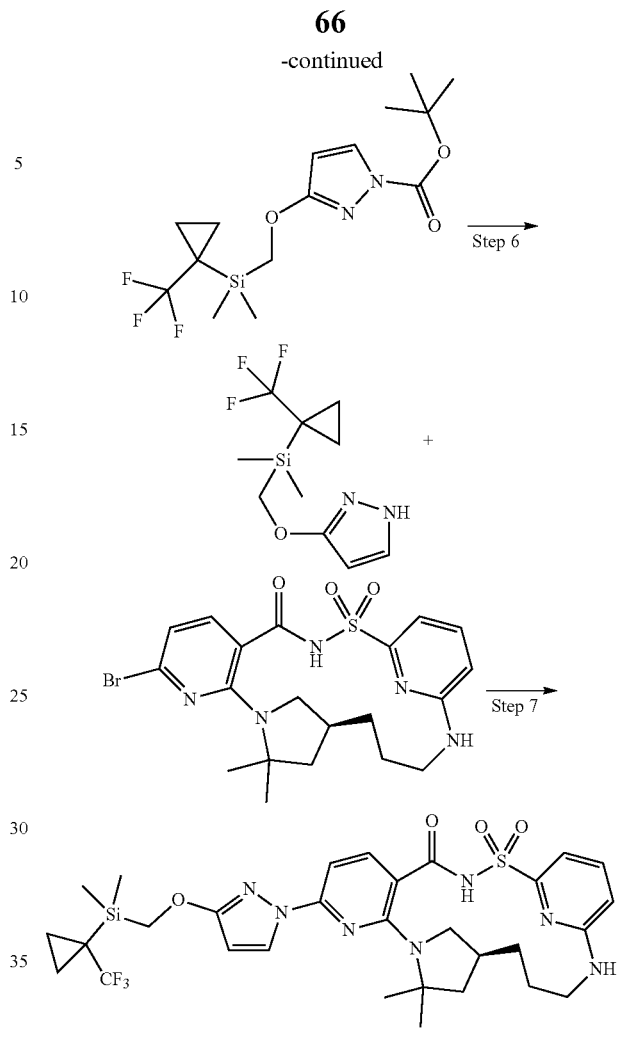

Step 1: Chloromethyl-dimethyl-[1-(trifluoromethyl)vinyl]silane

2-Bromo-3,3,3-trifluoro-prop-1-ene (3.28 g, 18.186 mmol) and chloro-(chloromethyl)-dimethyl-silane (1.0604 g, 1 mL, 7.2627 mmol) were weighted in a round bottom flask. Diethylether (80 mL) was added. The septum sealed flask was placed under a nitrogen balloon and cooled in an ethanol/liquid nitrogen bath. A thermo couple thermometer reading was used to control the reaction temperature. The bath was maintained at −115° C. and stirred for 15 min. t-BuLi (10.8 mL of 1.7 M, 18.360 mmol) was then added dropwise via a syringe along the inner wall of the reaction flask. The temperature was maintained below −110° C. for 15 min, and then allowed to warm to −60° C. over 60 min. Dry ice was added to the cooling ethanol to keep the temperature below −60° C. during the later stage of cooling. NH$_4$Cl (5 mL, sat. aq.) was added, followed by water (10 mL). The mixture was let warm up to ~0° C. Layers were separated. The ether layer was washed with brine, dried over anhydrous MgSO₄, filtered and concentrated (>150 mm Hg, 25° C. bath temperature) to afford chloromethyl-dimethyl-[1-(trifluoromethyl)vinyl]silane (1.4 g, 76%) as a pale yellow oil. ¹HNMR (250 MHz, Chloroform-d) δ 6.47 (s, 1H), 5.95 (s, 1H), 2.91 (s, 2H), 0.35 (s, 6H).

Step 2: Chloromethyl-dimethyl-[1-(trifluoromethyl)cyclopropyl]silane

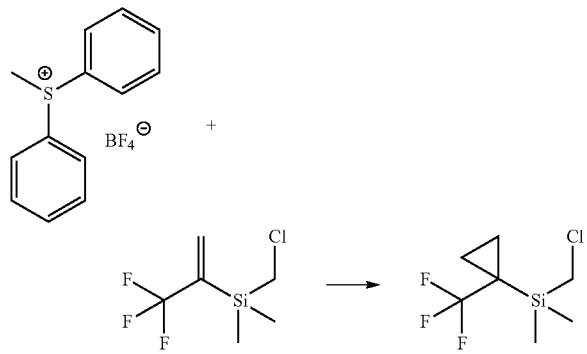

Chloromethyl-dimethyl-[1-(trifluoromethyl)vinyl]silane (1.4 g, 5.5260 mmol) was dissolved in THF (20 mL). Methyl(diphenyl)sulfonium; tetrafluoroborate (2.5 g, 8.2433 mmol) was added. The mixture was cooled in a dry ice acetone (~-75° C. bath temp). LiHMDS (16 mL of 1 M THF solution, 16.0 mmol) was added dropwise. The mixture was then allowed to slowly warm up to rt and stirred for 15 h. The mixture was loaded onto a ~80 g silica gel pre-column and purified with a 80 g silica gel column, using 100% pentane to afford the crude product, chloromethyl-dimethyl-[1-(trifluoromethyl)cyclopropyl]silane (720 mg, 48%), as a pale yellow oil. ¹HNMR (250 MHz, Chloroform-d) δ 2.92 (s, 2H), 1.1-0.94 (m, 2H), 0.79-0.59 (m, 2H), 0.27-0.03 (m, 6H).

Step 3: [Dimethyl-[1-(trifluoromethyl)cyclopropyl]silyl]methyl acetate

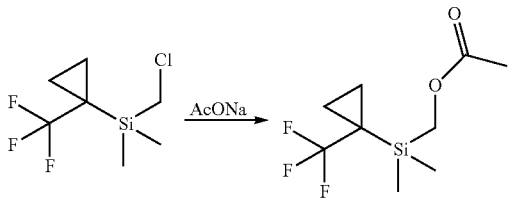

Chloromethyl-dimethyl-[1-(trifluoromethyl)cyclopropyl]silane (610 mg, 2.3927 mmol) was dissolved in DMF (5 mL) at RT. NaOAc (196.28 mg, 2.3927 mmol) was added in one portion. The mixture was sealed with a septum and placed in a 100° C. oil bath under stirring for 20 h. It was then cooled to RT and partitioned between diethylether (50 mL) and water (50 mL). The layers were separated and the ether layer was washed with water (30 mL×3), brine (30 mL), dried over anhydrous MgSO₄ and filtered. The filtrate was concentrated at >120 mm Hg (<26° C. oil bath). The light brown crude product (containing diethylether), [dimethyl-[1-(trifluoromethyl)cyclopropyl]silyl]methyl acetate (1.18 g, 99%), was used in the next step without further purification. ¹HNMR (250 MHz, Chloroform-d) δ 3.86 (s, 2H), 2.06 (s, 3H), 1.07-0.95 (m, 2H), 0.77-0.59 (m, 2H), 0.15 (s, 6H).

Step 4: [Dimethyl-[1-(trifluoromethyl)cyclopropyl]silyl]methanol

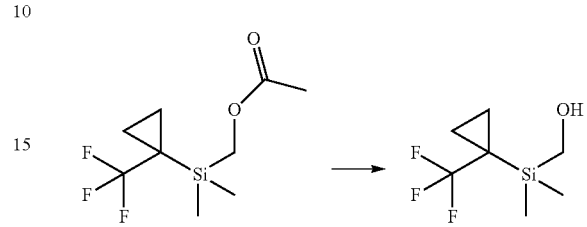

[Dimethyl-[1-(trifluoromethyl)cyclopropyl]silyl]methyl acetate (1.18 g, 2.3571 mmol) was dissolved in diethylether (15 mL) and cooled in ice water bath, stirred under a nitrogen atmosphere. LAH (100 mg, 0.1091 mL, 2.6347 mmol) was added in small portions. The mixture was stirred without external cooling. After 2h, Rochelle's salt (sat. aq. 10 mL) was added via a pipette. The mixture was stirred at RT for 30 min. The layers were separated and the aqueous layer was extracted with more ether (15 mL). The combined ether solution was dried over anhydrous MgSO₄, filtered and concentrated to afford crude [dimethyl-[1-(trifluoromethyl)cyclopropyl]silyl]methanol (800 mg, 86%) as a colorless oil. ¹HNMR (250 MHz, Chloroform-d) δ 1.07-0.95 (m, 2H), 0.81-0.61 (m, 2H), 0.34-0.04 (m, 6H) (missing CH₂ protons likely overlapped with residual diethyl ether peak).

Step 5: tert-Butyl 3-[[dimethyl-[1-(trifluoromethyl)cyclopropyl]silyl]methoxy]pyrazole-1-carboxylate

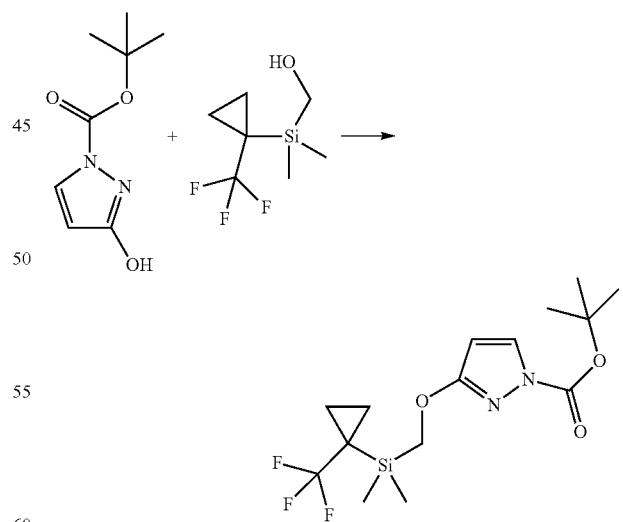

[Dimethyl-[1-(trifluoromethyl)cyclopropyl]silyl]methanol (800 mg, 2.02 mmol) was dissolved in THF (10 mL) at RT. tert-Butyl 3-hydroxypyrazole-1-carboxylate (405 mg, 2.20 mmol), PPh₃ (529 mg, 2.02 mmol) and DIAD (0.39 mL, 2.0176 mmol) were added. The mixture was stirred at RT for 30 min. HPLC analysis showed formation of the desired product. The mixture was stirred for another 12 h under nitrogen. It was then concentrated and the residue was purified by silica gel chromatography (40 g column), using 0-15% EtOAc in hexanes to afford a clear (tinged with yellow) oil. The product, tert-butyl 3-[[dimethyl-[1-(trifluoromethyl)cyclopropyl]silyl]methoxy]pyrazole-1-carboxylate (380 mg, 51%), solidified upon storage in a freezer to a pale yellow solid. ¹HNMR (250 MHz, Chloroform-d) δ 7.83 (d, J=3.0 Hz, 1H), 5.85 (d, J=3.0 Hz, 1H), 4.07 (s, 2H), 1.61 (s, 9H), 1.12-0.84 (m, 2H), 0.84-0.58 (m, 2H), 0.19 (s, 6H). ESI-MS m/z calc. 364.143, found 365.5 (M+1)⁺; Retention time: 4.04 minutes (LC method B).

Step 6: Dimethyl-(1H-pyrazol-3-yloxymethyl)-[1-(trifluoromethyl)cyclopropyl]silane

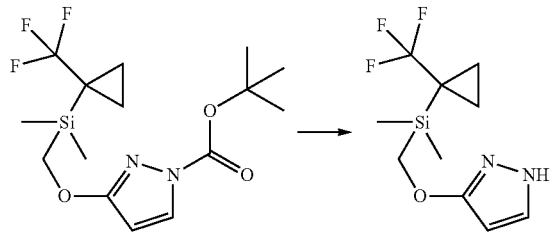 [SMILES: CC(C)(C)OC(=O)n1ccc(OC[Si](C)(C)C2(C(F)(F)F)CC2)n1 ; C[Si](C)(COc1cc[nH]n1)C1(C(F)(F)F)CC1]

tert-Butyl 3-[[dimethyl-[1-(trifluoromethyl)cyclopropyl] silyl]methoxy]pyrazole-1-carboxylate (550 mg, 1.43 mmol) was dissolved in DCM (20 mL) at rt. TFA (10 mL, 129.80 mmol) was added in one portion. The mixture was stirred for 90 min. It was then diluted with DCM (20 mL) and treated with NaHCO₃(10 mL, sat. aq.). The layers were separated and the DCM layer was dried over anhydrous Na₂SO₄, filtered and concentrated to afford dimethyl-(1H-pyrazol-3-yloxymethyl)-[1-(trifluoromethyl)cyclopropyl]silane (390 mg, 98%) as a colorless oil. ESI-MS m/z calc. 264.0906, found 265.3 (M+1)⁺; Retention time: 3.16 minutes (LC method B).

Step 7: (14S)-8-[3-({dimethyl[1-(trifluoromethyl) cyclopropyl]silyl}methoxy)-H-pyrazol-1-yl]-12,12-dimethyl-2λ⁶-thia-3,9,11,18,23-pentaazatetracyclo [17.3.1.1¹¹,¹⁴.0⁵,¹⁰]tetracosa-1(22),5(10),6,8,19 (23),20-hexaene-2,2,4-trione, Compound (1-1)

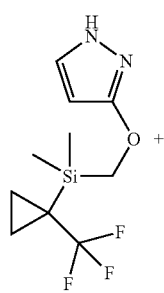 +

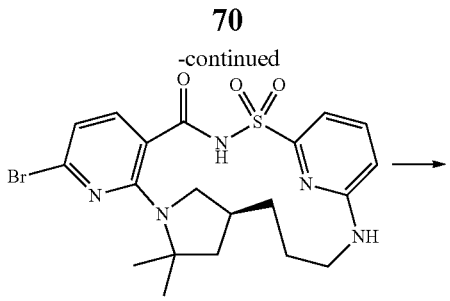

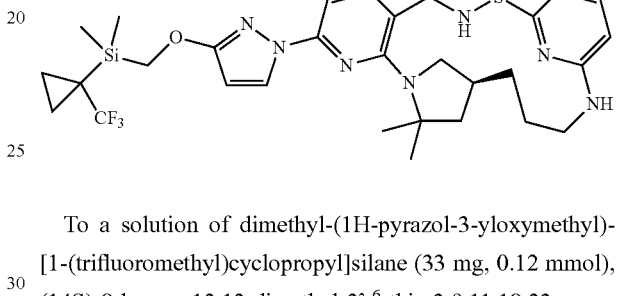

To a solution of dimethyl-(1H-pyrazol-3-yloxymethyl)-[1-(trifluoromethyl)cyclopropyl]silane (33 mg, 0.12 mmol), (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5(10), 6,8,19,21-hexaene-2,2,4-trione (55 mg, 0.106 mmol), L-proline (15 mg, 0.1303 mmol), and Na₂CO₃ (70 mg, 0.66 mmol) in DMSO (1 mL) was added CuI (12 mg, 0.06 mmol). The solution was purged with vacuum/N2 three times, then sealed and heated at 110° C. for 18 h. The reaction was diluted into 10 mL water, aqueous 3M HCl was added until the pH was acidic, and the product was extracted with ethyl acetate (2×50 mL). The combined organic layers were washed with brine (2×20 mL), dried over Na₂SO₄, and concentrated under reduced pressure. The residue was purified by prep.-HPLC using 30 to 80% acetonitrile in water buffered with 0.1% TFA to give: (14s)-8-[3-({dimethyl[1-(trifluoromethyl)cyclopropyl]silyl}methoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5(10),6,8,19(23), 20-hexaene-2,2,4-trione (6.4 mg, 9%) as a beige powder. ¹HNMR (400 MHz, DMSO-d₆) δ 12.49 (s, 1H), 8.21 (s, 1H), 7.82 (d, J=8.2 Hz, 1H), 7.58 (s, 1H), 7.05 (d, J=7.1 Hz, 1H), 6.98 (d, J=8.6 Hz, 1H), 6.94 (d, J=8.2 Hz, 1H), 6.71 (d, J=8.5 Hz, 1H), 6.13 (s, 1H), 4.05 (s, 2H), 3.93 (s, 1H), 3.15 (s, 1H), 2.97 (s, 1H), 2.71 (s, 1H), 2.12 (s, 1H), 1.75 (s, 2H), 1.61-151 (m, 9H), 1.33 (s, 1H), 0.98 (s, 2H), 0.89 (s, 2H), 0.19 (s, 6H). ESI-MS m/z calc. 677.2427, found 678.5 (M+1)⁺; Retention time: 3.83 minutes (LC Method H).

Example 11: Preparation of (14S)-8-[3-(2-{dispiro[2.0.2⁴.1³]heptan-7-yl}ethoxy)-1H-pyrazol-1-yl]-12,12-dimethyl-7-(trimethylsilyl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione, Compound (1-9)
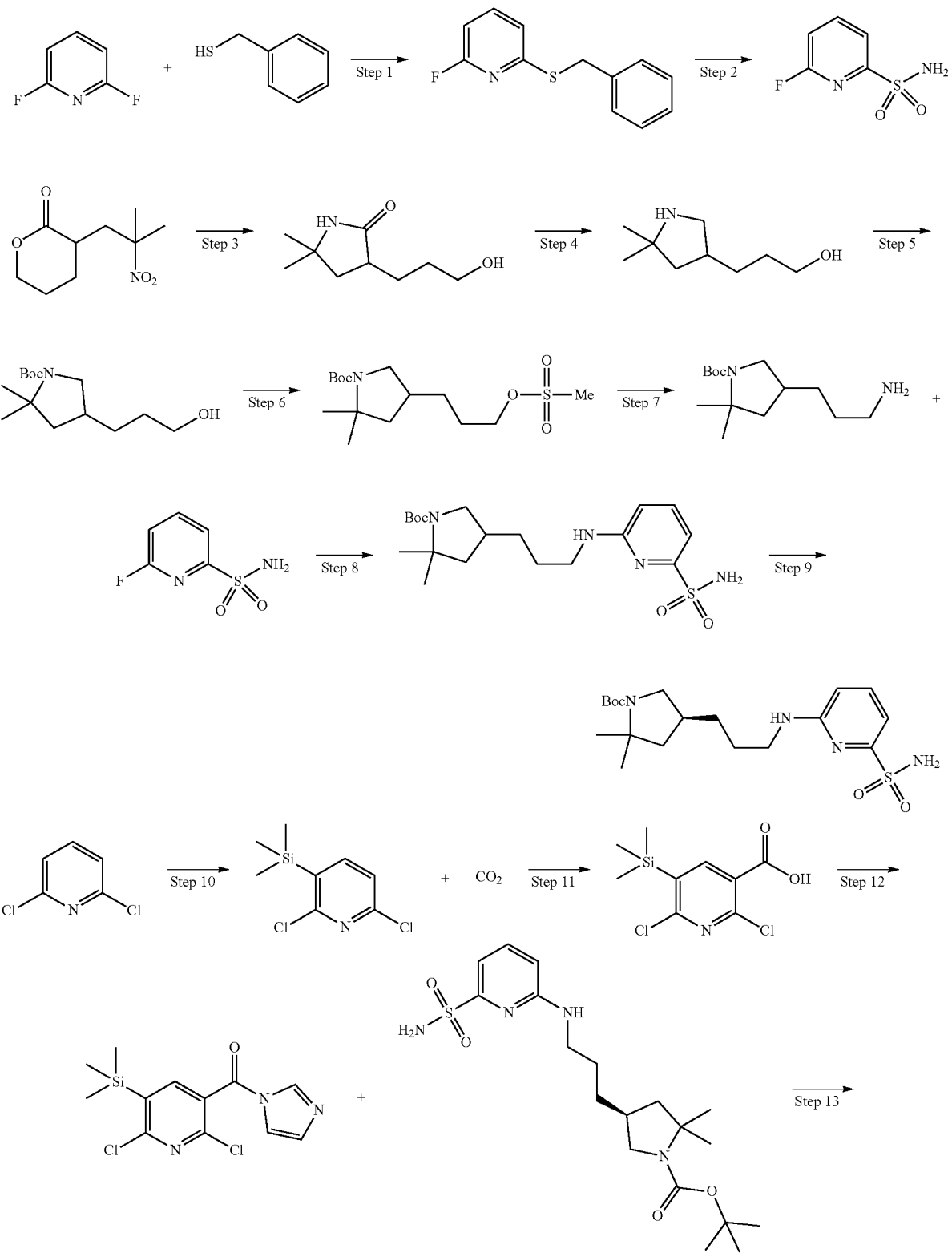

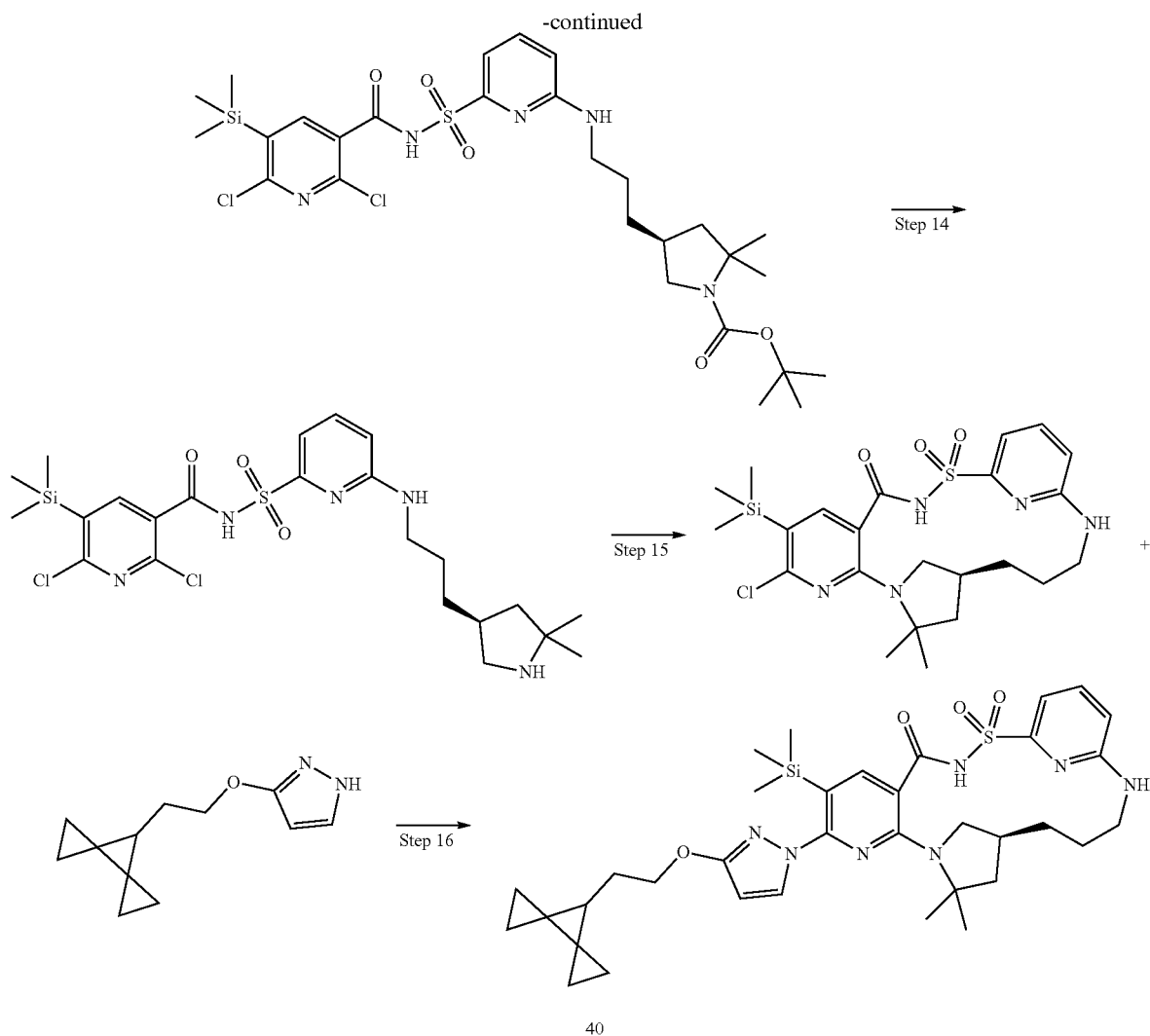

Step 1: 2-Benzylsulfanyl-6-fluoro-pyridine

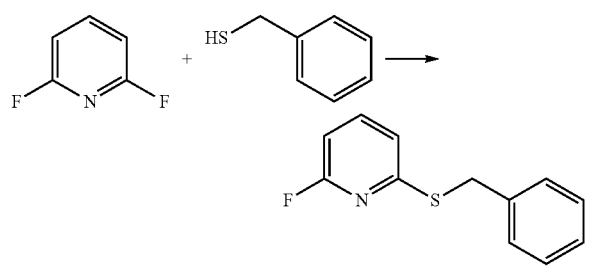

2,6-Difluoropyridine (200 g, 1.738 mol) was dissolved in dimethyl sulfoxide (2 L) in a 5 L three-necked round-bottomed flask equipped with an overhead stirrer, temperature probe and addition funnel. Cesium carbonate (572.4 g, 1.757 mol) was added. Phenylmethanethiol (206 mL, 1.755 mol) was added dropwise via addition funnel. An exotherm was observed during the addition. The temperature rose to approximately 40° C. The reaction was stirred overnight at room temperature. The reaction was poured into water and extracted with dichloromethane. The extract was washed twice with water and filtered over a small plug of silica gel. The plug was eluted with dichloromethane and the filtrate was evaporated in vacuo to afford 2-benzylsulfanyl-6-fluoro-pyridine (366 g, 96%) as a peach-colored oil that solidified under vacuum to huge blocky plates. $^1$H NMR (400 MHz, Chloroform-d) δ 7.58 (q, J 7.9 Hz, 1H), 7.48-7.41 (m, 2H), 7.36-7.25 (m, 3H), 7.06 (dd, J 7.6, 2.1 Hz, 1H), 6.62 (dd, J 7.9, 2.6 Hz, 1H), 4.43 (s, 2H).

Step 2: 6-Fluoropyridine-2-sulfonamide

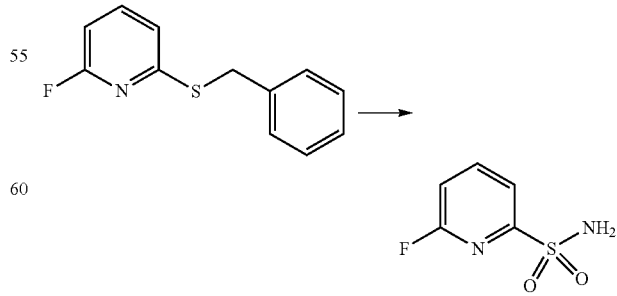

2-Benzylsulfanyl-6-fluoro-pyridine (303.2 g, 1.383 mol) was dissolved in chloroform (2.0 L) in a 12 L three-necked round-bottomed flask equipped with an overhead stirrer and temperature probe. Water (1.5 L) was added and the mixture was cooled in an ice bath to 0° C. and vigorously stirred. Chlorine gas from a lecture bottled was bubbled vigorously into the reaction by way of a Pasteur pipet inserted through a septum on the third neck of the flask. A white precipitate rapidly formed. An exotherm was observed during the addition. The chlorine addition was stopped when the temperature rose to 20° C. The reaction was allowed to cool again before the addition of more chlorine gas. Dosing was continued until the reaction turned a yellowish-green color and stayed that way after stirring for 30 min. At this point, no further exotherms were observed. The reaction was poured into a solution of 40% aqueous sodium bisulfite. The organic layer was separated and the aqueous was extracted with another portion of chloroform. The organic layers were combined, dried over magnesium sulfate, filtered, and evaporated in vacuo to afford a slightly yellow oil. The oil was dissolved in dichloromethane (1.5 L) and added dropwise to ammonium hydroxide (1.5 L of 40% w/v, 17.12 mol) in a 12 L three-necked round-bottomed flask equipped with an overhead stirrer, temperature probe, and addition funnel. The ammonium hydroxide solution was cooled to 0° C. in an ice-bath before the addition. The addition rate was adjusted so the temperature of the reaction stayed below 10° C. The resulting greenish-yellow solution was stirred for an hour and poured into ice. The layers were separated (the organic layer was dark green) and the aqueous layer was extracted with more dichloromethane. The organic layers were discarded. The aqueous layer was cooled in an ice bath and concentrated aqueous hydrochloric acid was added in portions to the aqueous layer until the pH was strongly acidic. The resulting mixture was stirred as each portion was added. The resulting aqueous solution was extracted twice with ethyl acetate. The organic layers were combined, dried over magnesium sulfate, filtered, and evaporated in vacuo to afford a light brown solid. The solid was mixed with dichloromethane (approximately 500 mL) and stirred with a magnetic stirbar until most of the large clumps had broken up. Approximately 1.5 L of pentane was added which precipitated a lot of light brown solid. The resulting mixture was stirred briefly and then filtered. The filter cake was washed with pentane and dried in vacuo to afford 6-fluoro-pyridine-2-sulfonamide (204.1 g, 84%) as a light brown solid. $^1$H NMR (300 MHz, dimethyl sulfoxide-d6) δ 8.52-8.11 (m, 1H), 7.89 (dd, J 7.8, 2.7 Hz, 1H), 7.67 (s, 2H), 7.57-7.44 (m, 1H).

Step 3:
3-(3-Hydroxypropyl)-5,5-dimethyl-pyrrolidin-2-one

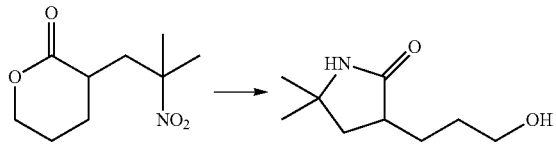

A 1000 mL, 3-neck round bottom flask was fitted with a Teflon stir bar, a heating mantle, a J-Kem temperature probe/controller and rubber septa. The vessel was charged with 3-(2-methyl-2-nitro-propyl)tetrahydropyran-2-one (25 g, 124.2 mmol) and ethyl alcohol (375 mL) which provided a white suspension. Stirring was commenced and the suspension was heated to 40° C. for 10 min which provided a clear colorless solution. The vessel was then fitted with a gas dispersion tube and the solution was degased with nitrogen for 15 min. The vessel was then charged with Raney Nickel (8.019 g of 50% w/w, 68.31 mmol) and the vessel was then fitted with the septa. The vessel was evacuated and placed under a hydrogen atmosphere. The process was repeated for three cycles. The vessel was then placed under 1 atmosphere of hydrogen and the reaction mixture was gradually heated to 60° C. The reaction was continued to stir at 60° C. for 24 h. After cooling to room temperature, the vessel was fitted with a gas dispersion tube and the reaction mixture was degased with nitrogen for 15 min. The mixture was vacuum filtered through a glass frit Buchner funnel with a 20 mm layer of celite. The filter cake was displacement washed with ethanol (2×100 mL) and pulled until slightly ethyl alcohol wet, then wetted with water and the used Raney nickel catalyst was discarded under water. The clear pale amber filtrate was concentrated under reduced pressure to a clear viscous light amber oil. The oil was diluted with methyl tert-butyl ether (1500 mL) and the cloudy solution was concentrated under reduced pressure to a volume of about 150 mL which provided a suspension. The mixture was again diluted with methyl tert-butyl ether (1500 mL) and concentrated under reduced pressure to a volume of about 150 mL. The resulting suspension was allowed to stand at room temperature overnight (about 12 h). The solid was collected by vacuum filtration in a glass frit Buchner funnel and the filter cake was displacement washed with cold methyl tert-butyl ether (2×50 mL) and then pulled for 30 min. The material was further dried in a vacuum oven at 45° C. for 3 h to provide a white solid (19 g, 0.111 mol, 89% yield) as the product, 3-(3-hydroxypropyl)-5,5-dimethyl-pyrrolidin-2-one. $^1$H NMR (400 MHz, dimethyl sulfoxide-d6) δ 7.63 (s, 1H), 3.38 (t, J 6.5 Hz, 2H), 2.37 (tdd, J 9.8, 8.5, 4.4 Hz, 1H), 2.02 (dd, J 12.3, 8.6 Hz, 1H), 1.72 (tdd, J 9.6, 7.5, 4.4 Hz, 1H), 1.52-1.32 (m, 3H), 1.28-1.03 (m, 7H).

Step 4: 3-(5,5-dimethylpyrrolidin-3-yl)propan-1-ol

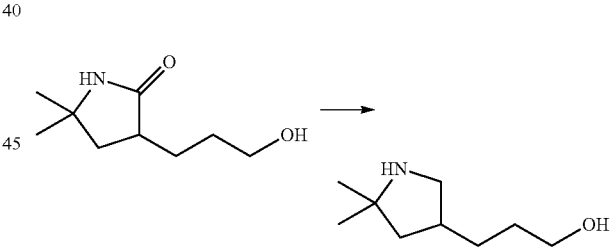

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with lithium aluminum hydride pellets (19.39 g, 510.9 mmol). The vessel was then charged with tetrahydrofuran (500 mL, 20 mL/g). Stirring was commenced and the pot temperature was recorded at 20° C. The mixture was allowed to stir at room temperature for 0.5 h to allow the pellets to dissolve. The pot temperature of the resulting grey suspension was recorded at 24° C. The addition funnel was charged with a solution of 3-(3-hydroxypropyl)-5,5-dimethyl-pyrrolidin-2-one (25 g, 146.0 mmol) in tetrahydrofuran (500 mL) and the clear pale yellow solution was added dropwise over 90 min. Slight heating was required to achieve homogeneity. After the completed addition the pot temperature of the resulting greyish suspension was recorded at 24° C. The mixture was then heated to a pot temperature of 65° C. and the condition was maintained for 72 h. Analysis of the reaction mixture at this point indicated some residual starting material still remaining and no change in product formation. The reaction was subsequently stopped at this point. The heating mantle was removed and the vessel was fitted with a cooling bath. The suspension was cooled to 0° C. with a crushed ice/water cooling bath and then quenched by the very slow dropwise addition of water (19.93 mL), followed by 15 wt % sodium hydroxide solution (19.93 mL) and then finally with water (59.79 mL). The pot temperature of the resulting white suspension was recorded at 5° C. The cooling bath was removed and the vessel was again fitted with a heating mantle. The suspension was warmed to 60° C. and the condition was maintained for 30 min. The warm suspension was vacuum filtered through a glass frit Buchner funnel with a 20 mm layer of celite. The filter cake was then displacement washed with 60° C. tetrahydrofuran (2×250 mL) and then pulled for 30 min. The clear filtrate was concentrated under reduced pressure to provide (23.5 g, 0.149 mol, 99% yield) of a clear light yellow viscous oil as the desired product, 3-(5,5-dimethylpyrrolidin-3-yl)propan-1-ol. $^1$H NMR (400 MHz, dimethyl sulfoxide-d6) δ 3.37 (dt, J 8.3, 6.4 Hz, 3H), 2.95 (dd, J 10.6, 7.6 Hz, 1H), 2.40 (dd, J 10.7, 7.7 Hz, 1H), 2.04 (dt, J 16.1, 8.1 Hz, 1H), 1.69 (dd, J 12.2, 8.2 Hz, 1H), 1.50-1.24 (m, 5H), 1.11-0.94 (m, 7H).

Step 5: tert-Butyl 4-(3-hydroxypropyl)-2,2-dimethyl-pyrrolidine-1-carboxylate

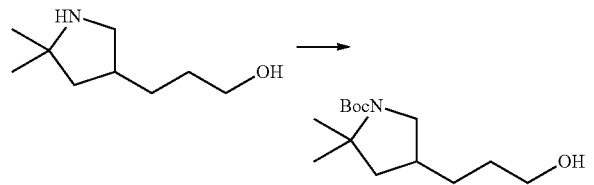

A 1 L, 3-neck round bottom flask was fitted with a mechanical stirrer, a cooling bath, an addition funnel, a J-Kem temperature probe and a nitrogen inlet/outlet. The vessel was charged under a nitrogen atmosphere with 3-(5,5-dimethylpyrrolidin-3-yl)propan-1-ol (15 g, 95.39 mmol) and dichloromethane (225 mL, 15 mL/g) which provided a clear light yellow solution. Stirring was commenced and the pot temperature was recorded at 19° C. The cooling bath was charged with crushed ice/water and the pot temperature was lowered to 0° C. The addition funnel was charged with triethylamine (12.55 g, 124.0 mmol) which was subsequently added neat dropwise over 5 min. No exotherm was observed. The addition funnel was then charged with di-tert-butyl dicarbonate (22.89 g, 104.9 mmol) dissolved in dichloromethane (225 mL). The clear pale yellow solution was then added dropwise over 30 min which resulted in gentle gas evolution. No exotherm was observed. The cooling bath was removed and the resulting clear light yellow solution was allowed to warm to room temperature and continue to stir at room temperature for 3 h. The reaction mixture was transferred to a separatory funnel and partitioned with water (75 mL). The organic was removed and washed with saturated sodium chloride solution (75 mL), dried over sodium sulfate (150 g) and then filtered through a glass frit Buchner funnel. The filtrate was concentrated under reduced pressure to provide (30 g) of a clear light yellow oil as the desired crude product. The material was purified by silica gel column flash chromatography (liquid load with dichloromethane) eluting with a gradient of 100% dichloromethane to 10% methyl alcohol in dichloromethane over 60 min collecting 50 mL fractions. The desired product fractions were combined and concentrated under reduced pressure to provide tert-butyl 4-(3-hydroxypropyl)-2,2-dimethyl-pyrrolidine-1-carboxylate (22 g, 0.0855 mol, 90% yield) as a clear pale yellow viscous oil. $^1$H NMR (400 MHz, DMSO-d$_6$) δ 4.38 (td, J 5.2, 1.4 Hz, 1H), 3.54 (dt, J 10.3, 6.7 Hz, 1H), 3.38 (td, J 6.6, 3.5 Hz, 2H), 2.76 (q, J 10.3 Hz, 1H), 2.07 (td, J 11.6, 5.7 Hz, 1H), 1.87 (ddd, J 16.7, 12.1, 6.0 Hz, 1H), 1.37 (dd, J 14.2, 10.4 Hz, 17H), 1.24 (s, 3H).

Step 6: tert-Butyl 2,2-dimethyl-4-(3-methylsulfonyl oxypropyl)pyrrolidine-1-carboxylate

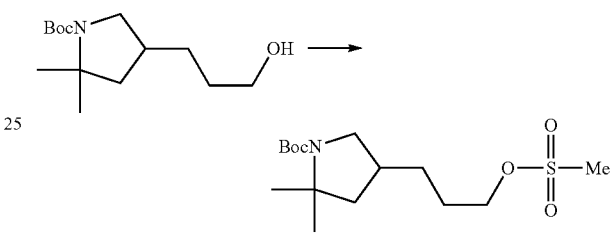

tert-Butyl 4-(3-hydroxypropyl)-2,2-dimethyl-pyrrolidine-1-carboxylate (50.5 g, 196.22 mmol) and triethylamine (39.711 g, 54.698 mL, 392.44 mmol) were dissolved in dichloromethane (500 mL) and the resulting solution was cooled in an ice water bath for 30 min. Mesyl chloride (24.725 g, 16.706 mL, 215.84 mmol) was added dropwise over a 30 min period, then the ice bath was removed and the mixture stirred at room temperature for one hour. The reaction was then quenched with saturated sodium bicarbonate solution (200 mL). The phases were separated and the organic phase was extracted with saturated sodium bicarbonate (200 mL) and water (2×100 mL). The aqueous phases were discarded and the organic phase was dried over sodium sulfate, filtered and concentrated in vacuo to obtain tert-butyl 2,2-dimethyl-4-(3-methylsulfonyl oxypropyl)pyrrolidine-1-carboxylate (64.2 g, 93%) as a pale yellow oil. ESI-MS m/z calc. 335.1766, found 336.4 (M+1)$^+$; Retention time: 5.54 min (LC Method C).

Step 7: tert-Butyl 4-(3-aminopropyl)-2,2-dimethyl-pyrrolidine-1-carboxylate

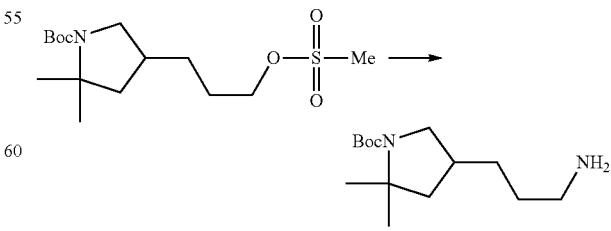

tert-Butyl 2,2-dimethyl-4-(3-methylsulfonyloxypropyl)pyrrolidine-1-carboxylate (64.2 g, 191.38 mmol) was dissolved in dioxane (650 mL) and then ammonium hydroxide (650 mL) was added and the resulting mixture heated to 45° C. for 18 h. After 18 h, the reaction was cooled to room temperature. The solution was diluted with 1M sodium hydroxide (200 mL) and then extracted with diethyl ether (3×650 mL). The aqueous phase was discarded and the combined organic phases were extracted with water (2×200 mL). The aqueous phases were discarded and the organic phase was dried over sodium sulfate, filtered and concentrated in vacuo to afford tert-butyl 4-(3-aminopropyl)-2,2-dimethyl-pyrrolidine-1-carboxylate (48.9 g, 95%) as a pale yellow oil. ESI-MS m/z calc. 256.2151, found 257.3 (M+1)$^+$; Retention time: 3.70 min (LC Method C).

Step 8: tert-Butyl 2,2-dimethyl-4-[3-[(6-sulfamoyl-2-pyridyl)amino]propyl]pyrrolidine-1-carboxylate

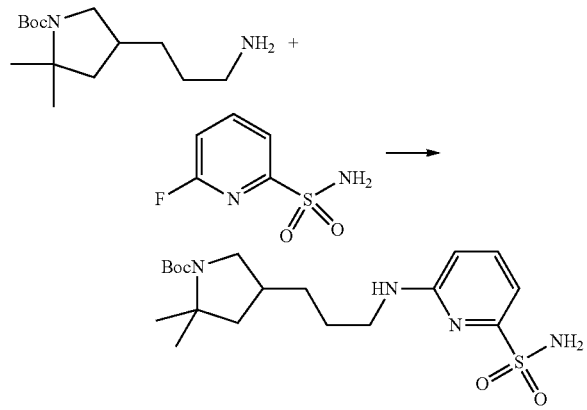

To tert-butyl 4-(3-aminopropyl)-2,2-dimethyl-pyrrolidine-1-carboxylate (8.91 g, 34.8 mmol) and 6-fluoropyridine-2-sulfonamide (6.13 g, 34.8 mmol) in dimethyl sulfoxide (75 mL) was added potassium carbonate (4.91 g, 35.5 mmol) and the mixture stirred at 100° C. for 12 h and then allowed to cool to ambient temperature and stirred for an additional 4 h (16 h total). The reaction mixture was slowly poured into hydrochloric acid (35 mL of 1 M, 35.00 mmol) in water (200 mL) (some foaming) and diluted with ethyl acetate (250 mL). The organic phase was separated and washed with 100 mL of brine. The organic phase was dried over magnesium sulfate, filtered over celite, and concentrated in vacuo to afford a dark yellow oil. The crude product was purified by silica gel chromatography eluting with 0%-100% ethyl acetate in hexanes. Collected both pure (9.0 g) and impure (3 g) fractions. Purified the impure fractions by silica gel chromatography eluting with 0%-100% ethyl acetate in hexanes affording, in total, tert-butyl 2,2-dimethyl-4-[3-[(6-sulfamoyl-2-pyridyl)amino]propyl]pyrrolidine-1-carboxylate (10.0 g, 69%). $^1$H NMR (400 MHz, dimethyl sulfoxide-d6) δ 7.52 (dd, J 8.5, 7.2 Hz, 1H), 7.07 (s, 2H), 6.95 (dd, J 7.2, 0.7 Hz, 2H), 6.61 (d, J 8.5 Hz, 1H), 3.55 (q, J 9.1 Hz, 1H), 3.32-3.24 (m, 2H), 2.79 (q, J 10.0 Hz, 1H), 2.13 (d, J 16.1 Hz, 1H), 1.96-1.82 (m, 1H), 1.51 (dt, J 18.0, 9.3 Hz, 2H), 1.37 (dd, J 12.9, 10.6 Hz, 15H), 1.24 (s, 3H). ESI-MS m/z calc. 412.21442, found 413.1 (M+1)$^+$; Retention time: 2.34 min (LC Method M).

Step 9: tert-Butyl(4S)-2,2-dimethyl-4-[3-[(6-sulfamoyl-2-pyridyl)amino]propyl]pyrrolidine-1-carboxylate

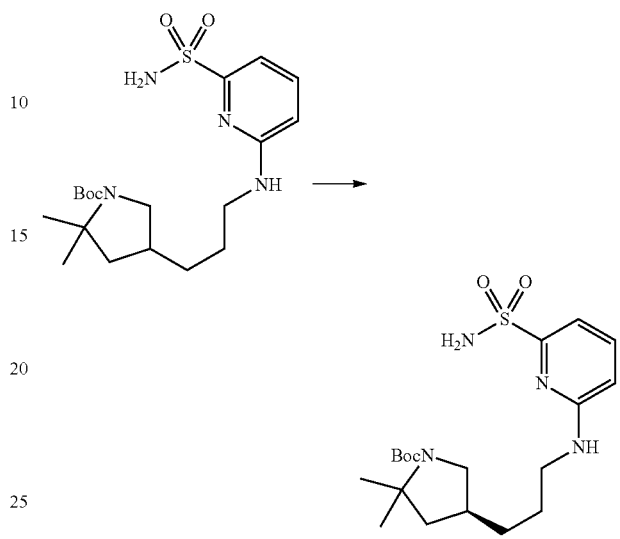

Subjected racemic tert-butyl 2,2-dimethyl-4-[3-[(6-sulfamoyl-2-pyridyl)amino]propyl]pyrrolidine-1-carboxylate (7 g, 16.97 mmol) to chiral separation by SFC chromatography using a ChiralPak IG (250×21.2 mm column, 5 μm particle size) with 40% methanol/60% carbon dioxide mobile phase at 70 mL/min over 11.0 min (injection volume=500 μL of 32 mg/mL solution in methanol) giving as the first peak to elute, tert-butyl (4S)-2,2-dimethyl-4-[3-[(6-sulfamoyl-2-pyridyl)amino]propyl]pyrrolidine-1-carboxylate (3.4481 g, 99%). ESI-MS m/z calc. 412.21442, found 413.2 (M+1)$^+$; Retention time: 0.63 min (LC Method N).

Step 10: (2,6-Dichloro-3-pyridyl)-trimethyl-silane

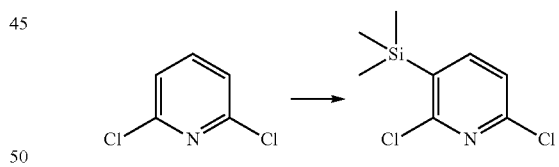

2,6-Dichloropyridine (4.01 g, 27.10 mmol) was dissolved in THF (80 mL) and cooled in a dry ice/acetone bath. LDA in THF/heptane/ethylbenzene (15 mL of 2 M, 30.00 mmol) was added slowly and the reaction was stirred at −75° C. for 1 h. At this point, TMS-Cl (3.5 mL, 27.58 mmol) was added and the reaction mixture was stirred at −75° C. for an additional 1 h. The reaction was quenched with aq HCl (50 mL of 1 M, 50.00 mmol) and allowed to warm to room temperature. The layers were separated, and the aqueous layer was further extracted with diethyl ether. The organics were combined, washed with brine, dried over sodium sulfate and evaporated. The crude liquid was purified by silica gel chromatography eluting with 0-10% ethyl acetate in hexanes to yield (2,6-dichloro-3-pyridyl)-trimethyl-silane (3.933 g, 66%) as a clear liquid. $^1$H NMR (400 MHz, DMSO-d$_6$) δ 7.93 (d, J 7.7 Hz, 1H), 7.56 (d, J 7.7 Hz, 1H), 0.36 (s, 9H). ESI-MS m/z calc. 219.00378, found 220.1 (M+1)⁺; Retention time: 0.76 minutes (LC method D).

Step 11: 2,6-Dichloro-5-trimethylsilyl-pyridine-3-carboxylic Acid

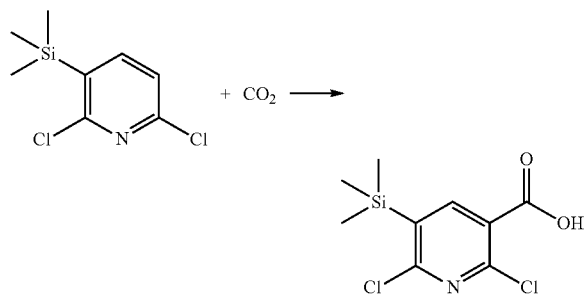

(2,6-Dichloro-3-pyridyl)-trimethyl-silane (531 mg, 2.41 mmol) was dissolved in THF (10 mL) and cooled to −75° C. in a dry ice:acetone bath. LDA in THF/heptane/ethylbenzene (1.25 mL of 2 M, 2.50 mmol) was added slowly and the reaction mixture was stirred an additional 1 h. $CO_2$ gas was bubbled through the reaction mixture for 1 min. The reaction was allowed to warm to room temperature and stir for 15 min. The reaction mixture was diluted with ethyl acetate and washed with 1M aqueous HCl. The organics were separated, washed with brine, dried over sodium sulfate and evaporated. The crude material was triturated with hexanes and the resulting solid was collected by vacuum filtration. The solid was further dried to give 2,6-dichloro-5-trimethylsilyl-pyridine-3-carboxylic acid (353 mg, 55%) as a white solid. ¹H NMR (400 MHz, DMSO-d₆) δ 13.96 (s, 1H), 8.21 (s, 1H), 0.38 (s, 9H). ESI-MS m/z calc. 262.99362, found 264.1 (M+1)⁺; Retention time: 0.65 minutes (LC method A).

Step 12: (2,6-Dichloro-5-trimethylsilyl-3-pyridyl)-imidazol-1-yl-methanone

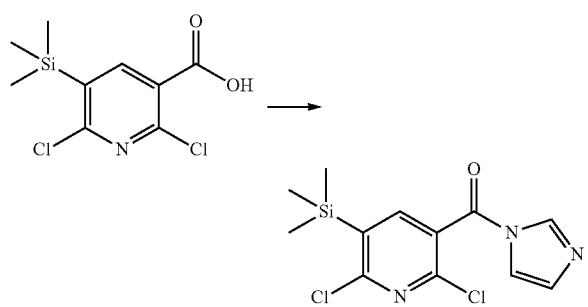

2,6-Dichloro-5-trimethylsilyl-pyridine-3-carboxylic acid (570 mg, 2.158 mmol) and CDI (530 mg, 3.269 mmol) were dissolved in THF (9 mL) and left to react overnight. The reaction mixture was concentrated under reduced pressure and the resulting residue was purified on silica gel using 0 to 60% ethyl acetate (the desired product eluted at around 40% ethyl acetate) to provide (2,6-dichloro-5-trimethylsilyl-3-pyridyl)-imidazol-1-yl-methanone (430 mg, 63%) as an oil that slowly crystallized on standing. ¹H NMR (400 MHz, CDCl₃) δ 7.93 (s, 1H), 7.86 (s, 1H), 7.44 (s, 1H), 7.20 (d, J 1.0 Hz, 1H), 0.48-0.34 (m, 9H). ESI-MS m/z calc. 313.0205, found 314.0 (M+1)⁺; Retention time: 1.91 minutes (LC method L).

Step 13: tert-Butyl (4S)-4-[3-[[6-[(2,6-dichloro-5-trimethylsilyl-pyridine-3-carbonyl)sulfamoyl]-2-pyridyl]amino]propyl]-2,2-dimethyl-pyrrolidine-1-carboxylate

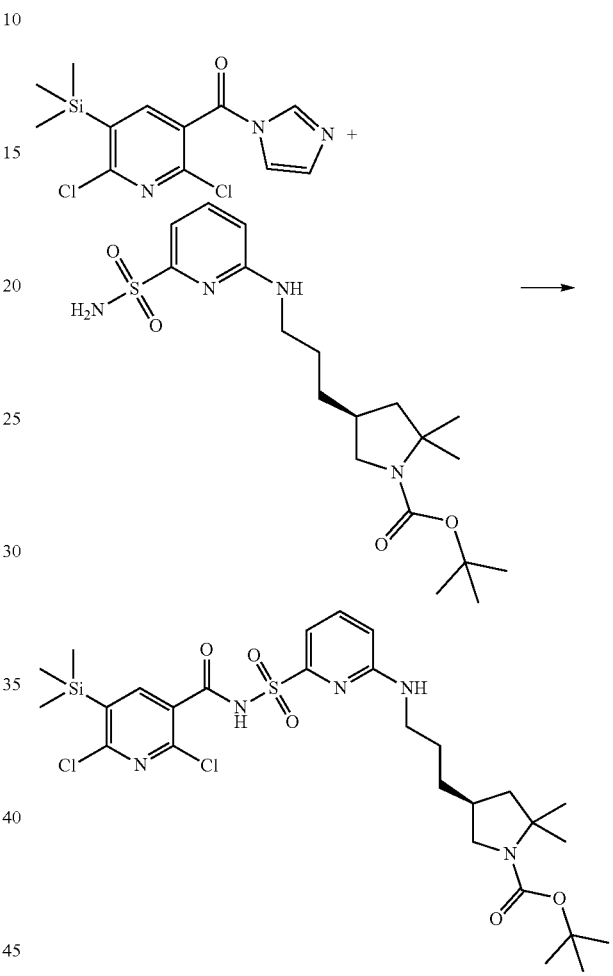

DBU (1.2 mL, 8.0243 mmol) was added to a solution of (2,6-dichloro-5-trimethylsilyl-3-pyridyl)-imidazol-1-yl-methanone (1.2 g, 3.8187 mmol) and tert-butyl (4S)-2,2-dimethyl-4-[3-[(6-sulfamoyl-2-pyridyl)amino]propyl]pyrrolidine-1-carboxylate (1.58 g, 3.830 mmol) dissolved in THF (72 mL) then stirred for 18 h at room temperature. The reaction mixture was concentrated under reduced pressure and the residue was purified directly by reverse phase chromatography on a C18 cartridge using 5 to 100% methanol in water (with 0.1% formic acid content) to provide tert-butyl (4S)-4-[3-[[6-[(2,6-dichloro-5-trimethylsilyl-pyridine-3-carbonyl)sulfamoyl]-2-pyridyl]amino]propyl]-2,2-dimethyl-pyrrolidine-1-carboxylate (1.41 g, 56%) as a beige powder. ¹H NMR (400 MHz, DMSO-d₆) δ 12.80 (br. s., 1H), 7.93 (d, J 2.7 Hz, 1H), 7.60 (t, J 7.8 Hz, 1H), 7.28-7.10 (m, 2H), 6.73 (d, J 8.6 Hz, 1H), 3.57-3.45 (m, 1H), 3.26-3.18 (m, 2H), 2.74 (t, J 10.3 Hz, 1H), 2.01 (br. s., 1H), 1.87-1.71 (m, 1H), 1.47 (br. s., 2H), 1.40-1.27 (m, 15H), 1.20 (s, 3H), 0.38 (s, 9H). ESI-MS m/z calc. 657.1975, found 558.2 (M-99)⁺; Retention time: 2.33 minutes (LC method L).

Step 14: 2,6-Dichloro-N-[[6-[3-[(3S)-5,5-dimethylpyrrolidin-3-yl]propylamino]-2-pyridyl]sulfonyl]-5-trimethylsilyl-pyridine-3-carboxamide

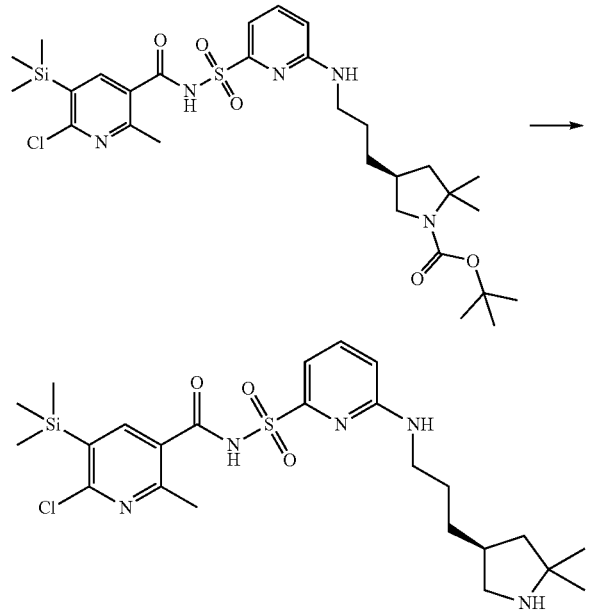

tert-Butyl (4S)-4-[3-[[6-[(2,6-dichloro-5-trimethylsilyl-pyridine-3-carbonyl)sulfamoyl]-2-pyridyl]amino]propyl]-2,2-dimethyl-pyrrolidine-1-carboxylate (1.41 g, 2.1405 mmol) was dissolved in DCM (110 mL) and 2,2,2-trifluoroacetic acid (28 mL, 365.89 mmol) was added. After stirring for 40 min. at room temperature, the solvents were evaporated under reduced pressure and the resulting residue was left under high vacuum for 1 h. The product was dissolved in DCM (150 mL) concentrated under reduced pressure then dried under high vacuum to provide 6-dichloro-N-[[6-[3-[(3S)-5,5-dimethylpyrrolidin-3-yl]propylamino]-2-pyridyl]sulfonyl]-5-trimethylsilyl-pyridine-3-carboxamide (trifluoroacetate salt) (2.2 g, 131%). This crude product was further purified by reverse-phase chromatography using 5 to 100% methanol in pure water to provide 2,6-dichloro-N-[[6-[3-[(3S)-5,5-dimethylpyrrolidin-3-yl]propylamino]-2-pyridyl]sulfonyl]-5-trimethylsilyl-pyridine-3-carboxamide (920 mg, 77%) as a yellow powder. $^1$H NMR (400 MHz, ACETONITRILE-d3) δ 7.82 (s, 1H), 7.45 (t, J 7.7 Hz, 1H), 7.07 (d, J 7.1 Hz, 1H), 6.52 (d, J 8.3 Hz, 1H), 5.63 (br. s., 1H), 3.97-3.79 (m, 1H), 3.58 (dd, J 13.3, 6.5 Hz, 1H), 3.18-2.98 (m, 2H), 2.71 (br. s., 1H), 1.85 (dd, J 12.5, 7.3 Hz, 1H), 1.64-1.33 (m, 8H), 1.24 (s, 3H), 0.35 (s, 9H). ESI-MS m/z calc. 557.145, found 558.2 (M+1)$^+$; Retention time: 1.51 minutes (LC method L).

Step 15: (14S)-8-Chloro-12,12-dimethyl-7-(trimethylsilyl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione

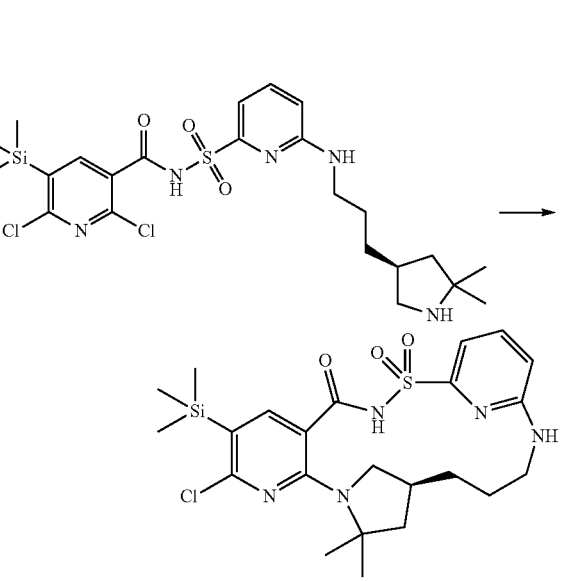

In a microwave vial, under nitrogen atmosphere, 2,6-dichloro-N-[[6-[3-[(3S)-5,5-dimethylpyrrolidin-3-yl]propylamino]-2-pyridyl]sulfonyl]-5-trimethylsilyl-pyridine-3-carboxamide (200 mg, 0.3580 mmol) was mixed with K$_2$CO$_3$ (50 mg, 0.362 mmol) in DMSO (3.2 mL), the microwave vial was capped then heated at 130° C. in an oil bath for 2 h. The reaction mixture was cooled down to room temperature, then injected directly on a Cis column and purified using a 10 to 100% gradient of methanol in water (containing 0.1% formic acid) to provide (14S)-8-chloro-12,12-dimethyl-7-(trimethylsilyl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (68 mg, 36%) as a pale yellow solid. $^1$H NMR (400 MHz, DMSO-d$_6$) δ 12.61 (br. s., 1H), 7.62 (s, 1H), 7.57 (t, J 7.8 Hz, 1H), 7.06 (d, J 7.3 Hz, 1H), 7.02-6.94 (m, 1H), 6.71 (d, J 8.6 Hz, 1H), 3.95-3.75 (m, 1H), 3.15-3.06 (m, 1H), 2.95 (d, J 13.2 Hz, 1H), 2.67-2.58 (m, 1H), 2.17-2.02 (m, 1H), 1.83 (dd, J 11.6, 4.8 Hz, 1H), 1.78-1.69 (m, 1H), 1.63-1.49 (m, 6H), 1.44 (s, 3H), 1.36-1.24 (m, 1H), 0.32 (s, 9H). ESI-MS m/z calc. 521.1684, found 522.2 (M+1)$^+$; Retention time: 2.1 minutes (LC method L).

Step 16: (14S)-8-[3-(2-{Dispiro[2.0.2$^4$.1$^3$]heptan-7-yl}ethoxy)-1H-pyrazol-1-yl]-12,12-dimethyl-7-(trimethylsilyl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione, Compound (1-9)

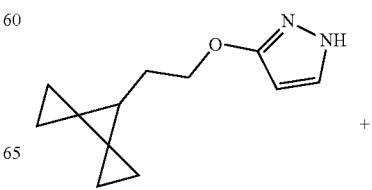

+

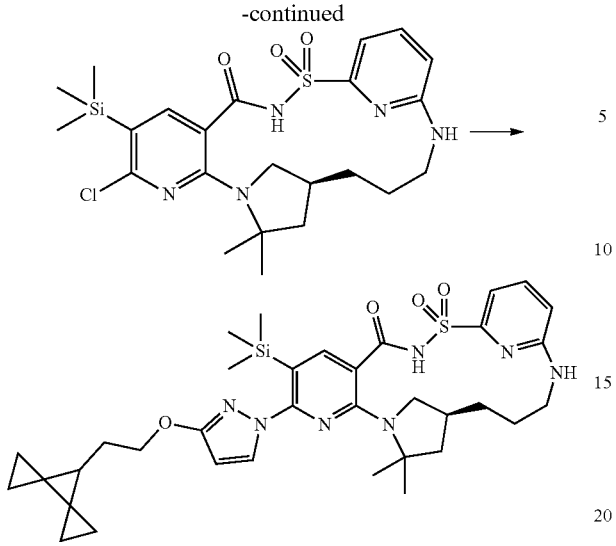

Under nitrogen (balloon) in a microwave vial, copper iodide (10 mg, 0.0525 mmol) was added to trans-N,N'-dimethylcyclohexane-1,2-diamine (8 mg, 0.0562 mmol), (14S)-8-chloro-12,12-dimethyl-7-(trimethylsilyl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (10 mg, 0.0192 mmol), 3-(2-dispiro[2.0.2$^4$.1$^3$]heptan-7-ylethoxy)-1H-pyrazole (12 mg, 0.0587 mmol) and potassium carbonate (9 mg, 0.0651 mmol) in DMSO (0.05 mL). The vial was heated at 130° C. over the week-end. The reaction mixture was cooled to room temperature and it was combined with the crude from another reaction run on 10 mg scale, and mixed with DMSO+acetonitrile, and was purified on a Cis column by reverse phase chromatography using 10 to 100% methanol in water (0.1% formic acid content) to provide (14S)-8-[3-(2-{dispiro[2.0.2$^4$.1$^3$]heptan-7-yl}ethoxy)-1H-pyrazol-1-yl]-12,12-dimethyl-7-(trimethylsilyl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (6.2 mg, 46%) as a white fluffy solid after lyophilization. $^1$H NMR (400 MHz, DMSO-d$_6$) δ 8.12 (br. s., 1H), 7.82 (s, 1H), 7.37 (t, J 7.3 Hz, 1H), 6.88 (d, J 6.6 Hz, 1H), 6.48-6.40 (m, 2H), 5.98 (br. s., 1H), 4.16 (t, J 6.7 Hz, 2H), 3.99-3.85 (m, 1H), 3.55-3.40 (m, 1H), 3.15-2.98 (m, 1H), 2.95-2.82 (m, 1H), 2.13-2.00 (m, 1H), 1.81 (q, J 6.6 Hz, 3H), 1.73-1.65 (m, 1H), 1.61-1.43 (m, 10H), 1.34-1.25 (m, J 9.8 Hz, 1H), 0.84-0.80 (m, 4H), 0.68-0.62 (m, 2H), 0.53-0.46 (m, 2H), 0.22 (s, 9H). ESI-MS m/z calc. 689.318, found 690.2 (M+1)$^+$; Retention time: 5.69 minutes (LC method F).

Example 12: Preparation of 2$^6$-(3-(2-(dispiro [2.0.2$^4$.1$^3$]heptan-7-yl)ethoxy)-1H-pyrazol-1-yl)-1$^5$, 1$^5$,9,9-tetramethyl-5-thia-4,7-diaza-9-sila-2(2,3),6(2,6)-dipyridina-1(1,3)-pyrrolidinacyclodecaphan-3-one 5,5-dioxide, Compound (1-10)

(1-10)

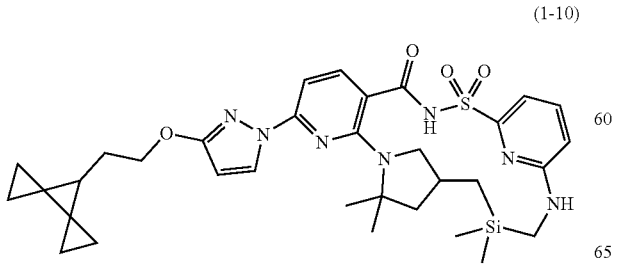

A synthetic route for Compound (1-10) is shown in the following scheme:

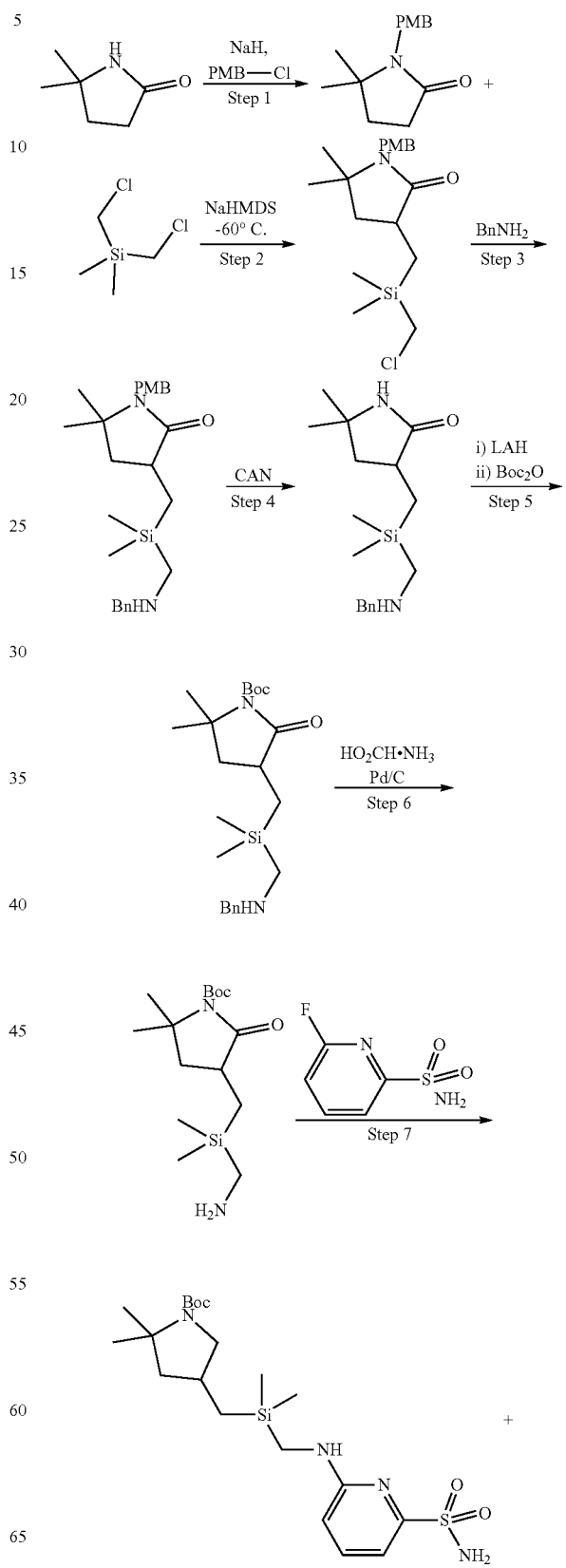

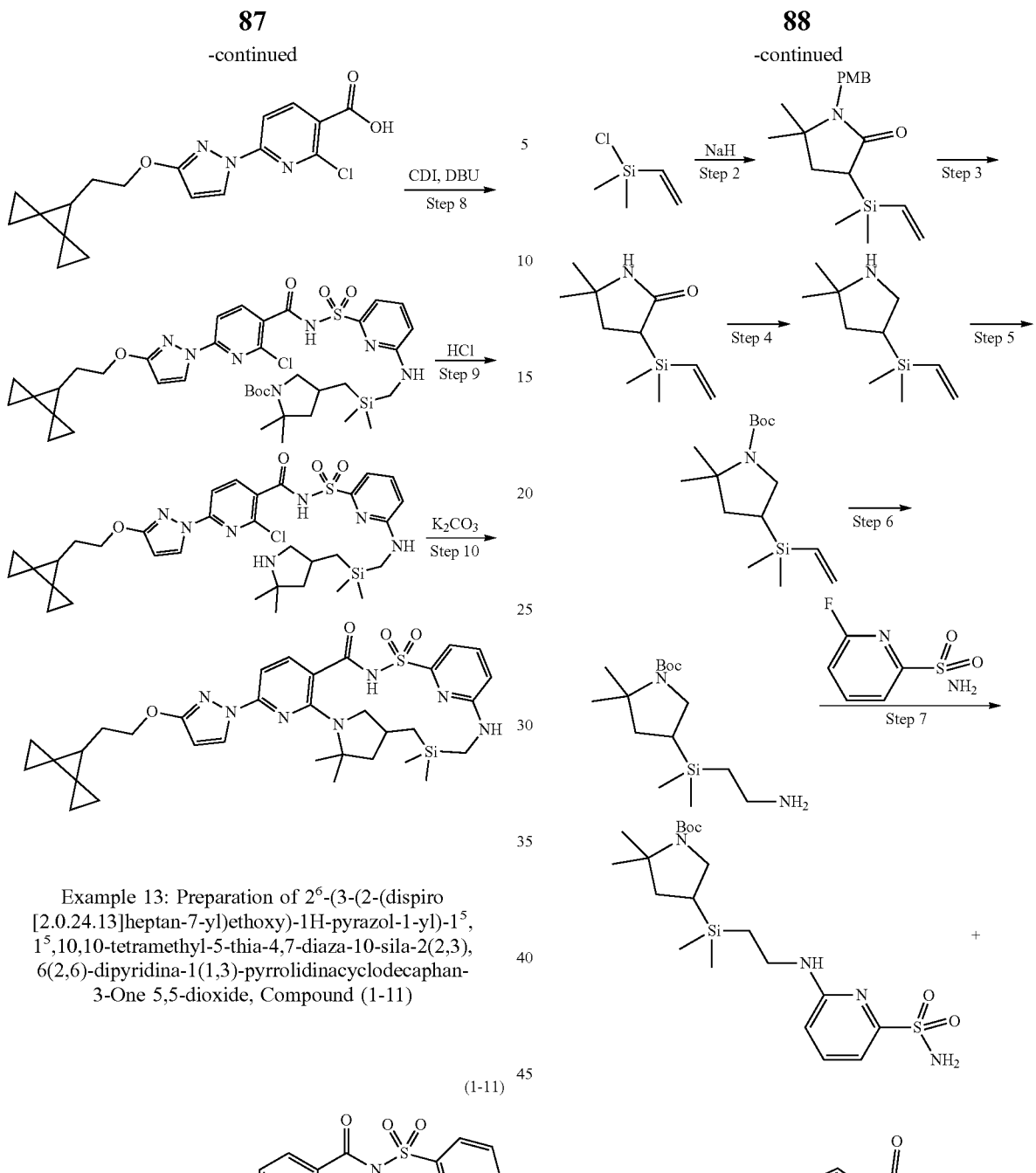
Example 13: Preparation of $2^6$-(3-(2-(dispiro[2.0.24.13]heptan-7-yl)ethoxy)-1H-pyrazol-1-yl)-$1^5$,$1^5$,10,10-tetramethyl-5-thia-4,7-diaza-10-sila-2(2,3),6(2,6)-dipyridina-1(1,3)-pyrrolidinacyclodecaphan-3-One 5,5-dioxide, Compound (1-11)
A synthetic route for Compound (1-11) is shown in the following scheme:
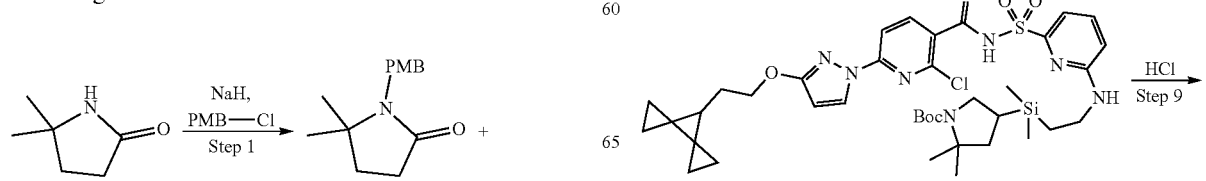

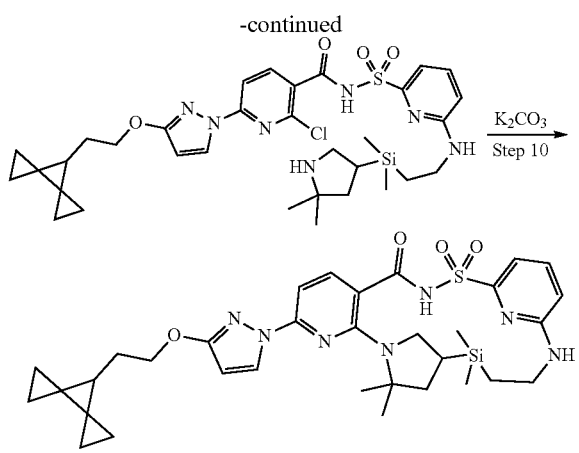

Example 14: Bioactivity Assays

Solutions

Base medium (ADF+++) consisted of Advanced DMEM/Ham's F12. 2 mM Glutamax, 10 mM HEPES, 1 μg/ml penicillin/streptomycin.

Intestinal enteroid maintenance medium (IEMM) consisted of ADF+++, 1×B27 supplement, 1×N2 supplement, 1.25 mM N-acetyl cysteine, 10 mM Nicotinamide, 50 ng/mL hEGF, 10 nM Gastrin, 1 μg/mL hR-spondin-1, 100 ng/mL hNoggin, TGF-b type 1 inhibitor A-83-01, 100 μg/mL Primocin, 10 μM P38 MAPK inhibitor SB202190.

Bath 1 Buffer consisted of 1 mM $MgCl_2$, 160 mM NaCl, 4.5 mM KCl, 10 mM HEPES, 10 mM Glucose, 2 mM $CaCl_2$).

Chloride Free Buffer consisted of 1 mM Magnesium Gluconate, 2 mM Calcium Gluconate, 4.5 mM Potassium Gluconate, 160 mM Sodium Gluconate, 10 mM HEPES, 10 mM Glucose.

Bath1 Dye Solution consisted of Bath 1 Buffer, 0.04% Pluronic F127, 20 μM Methyl Oxonol, 30 μM CaCCinh-AO1, 30 μM Chicago Sky Blue.

Chloride Free Dye Solution consisted of Chloride Free Buffer, 0.04% Pluronic F127, 20 μM Methyl Oxonol, 30 μM CaCCinh-AO1, 30 μM Chicago Sky Blue.

Chloride Free Dye Stimulation Solution consisted of Chloride Free Dye Solution, 10 μM forskolin, 100 μM IBMX, and 300 nM Compound III.

Cell Culture

Human intestinal epithelial enteroid cells were obtained from the Hubrecht Institute for Developmental Biology and Stem Cell Research, Utrecht, The Netherlands and expanded in T-Flasks as previously described (Dekkers J F, Wiegerinck C L, de Jonge H R, Bronsveld I, Janssens H M, de Winter-de Groot K M, Brandsma A M, de Jong N W M, Bijvelds M J C, Scholte B J, Nieuwenhuis E E S, van den Brink S, Clevers H, van der Ent C K, Middendorp S and M Beekman J M. A functional CFTR assay using primary cystic fibrosis intestinal organoids. Nat Med. 2013 July; 19(7):939-45.).

Enteroid Cell Harvesting and Seeding

Cells were recovered in cell recovery solution, collected by centrifugation at 650 rpm for 5 min at 4° C., resuspended in TryPLE and incubated for 5 min at 37° C. Cells were then collected by centrifugation at 650 rpm for 5 min at 4° C. and resuspended in IEMM containing 10 μM ROCK inhibitor (RI). The cell suspension was passed through a 40 μm cell strainer and resuspended at 1×106 cells/mL in IEMM containing 10 μM RI. Cells were seeded at 5000 cells/well into multi-well plates and incubated for overnight at 37° C., 95% humidity and 5% $CO_2$ prior to assay.

Membrane Potential Dye Assay

Enteroid cells were incubated with test compound in IEMM for 18-24 hours at 37° C., 95% humidity and 5% $CO_2$. Following compound incubations, a membrane potential dye assay was employed using a FLIPR Tetra to directly measure the potency and efficacy of the test compound on CFTR-mediated chloride transport following acute addition of 10 μM forskolin and 300 nM N-[2,4-bis(1,1-dimethylethyl)-5-hydroxyphenyl]-1,4-dihydro-4-oxoquinoline-3-carboxamide. Briefly, cells were washed 5 times in Bath 1 Buffer. Bath 1 Dye Solution was added and the cells were incubated for 25 min at room temperature. Following dye incubation, cells were washed 3 times in Chloride Free Dye Solution. Chloride transport was initiated by addition of Chloride Free Dye Stimulation Solution and the fluorescence signal was read for 15 min. The CFTR-mediated chloride transport for each condition was determined from the AUC of the fluorescence response to acute forskolin and 300 nM N-[2,4-bis(1,1-dimethylethyl)-5-hydroxyphenyl]-1,4-dihydro-4-oxoquinoline-3-carboxamide stimulation. Chloride transport was then expressed as a percentage of the chloride transport following treatment with 1 μM (14S)-8-[3-(2-{Dispiro[2.0.2.1]heptan-7-yl}ethoxy)-1H-pyrazol-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione, 3 μM (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide and 300 nM acute N-[2,4-bis(1,1-dimethylethyl)-5-hydroxyphenyl]-1,4-dihydro-4-oxoquinoline-3-carboxamide triple combination control (% Activity).

Table 3 represents CFTR modulating activity for representative compounds of the invention generated using one or more of the assays disclosed herein. (Max Activity: +++ is >60%; ++ is 30-60%; + is <30%. EC50: +++ is <1 μM; ++ is 1-3 μM; + is >3 μM; and ND is "not determined.")

TABLE 3

| Compound Number | Structure | EC$_{50}$ (μM) | Max Activity (%) |
|---|---|---|---|
| (1-1) | 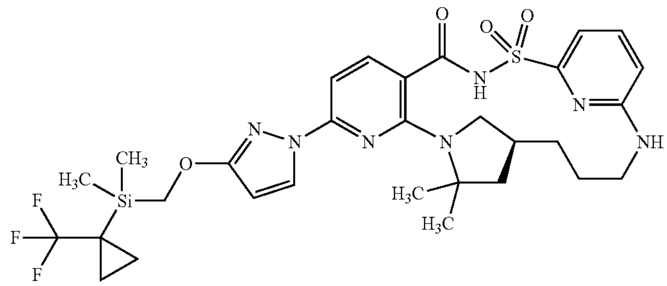 [SMILES: CC1(C)C[C@@H]2CCCNc3cccc(n3)S(=O)(=O)NC(=O)c3ccc(-n4ccc(OC[Si](C)(C)C5(C(F)(F)F)CC5)n4)nc3N1C2] | +++ | +++ |
| (2-1) | 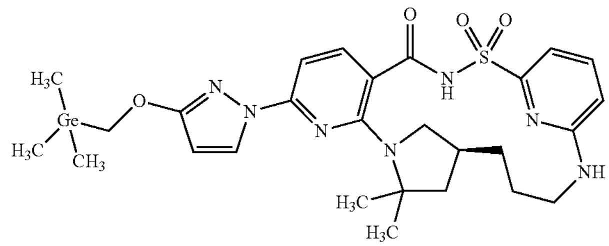 | +++ | +++ |
| (1-2) | 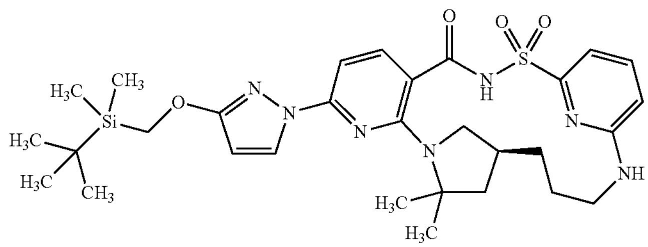 [SMILES: CC1(C)C[C@@H]2CCCNc3cccc(n3)S(=O)(=O)NC(=O)c3ccc(-n4ccc(OC[Si](C)(C)C(C)(C)C)n4)nc3N1C2] | +++ | +++ |
| (1-3) | 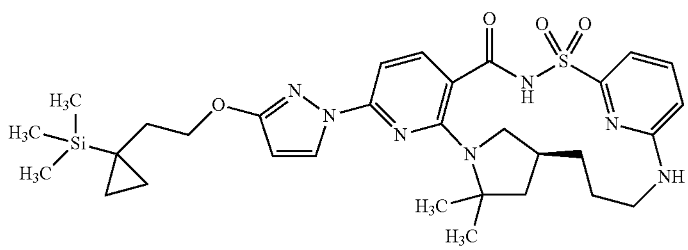 [SMILES: CC1(C)C[C@@H]2CCCNc3cccc(n3)S(=O)(=O)NC(=O)c3ccc(-n4ccc(OCCC5([Si](C)(C)C)CC5)n4)nc3N1C2] | +++ | +++ |
| (1-4) | 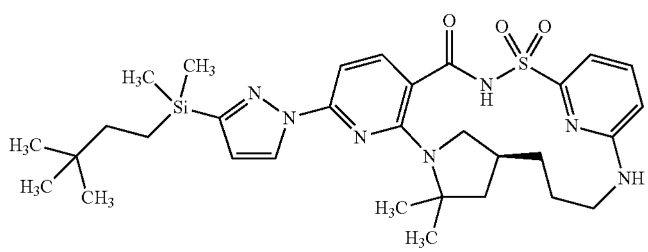 [SMILES: CC(C)(C)CC[Si](C)(C)c1ccn(-c2ccc3c(n2)N2C[C@@H](CCCNc4cccc(n4)S(=O)(=O)NC3=O)CC2(C)C)n1] | +++ | +++ |
| (1-5) | 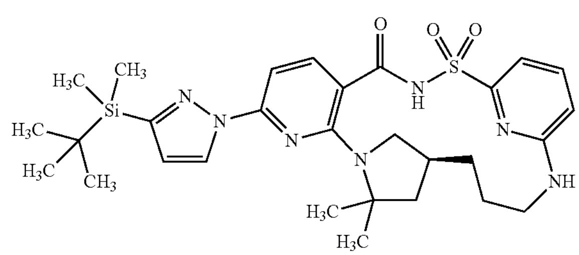 [SMILES: CC1(C)C[C@@H]2CCCNc3cccc(n3)S(=O)(=O)NC(=O)c3ccc(-n4ccc([Si](C)(C)C(C)(C)C)n4)nc3N1C2] | ND | ND |

TABLE 3-continued
| Compound Number | Structure | EC$_{50}$ (μM) | Max Activity (%) |
| --- | --- | --- | --- |
| (1-6) | 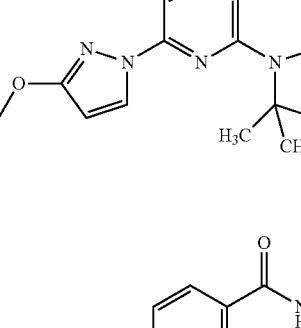 | +++ | +++ |
| (1-7) | 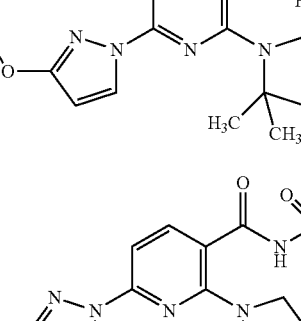 | +++ | +++ |
| (1-8) | 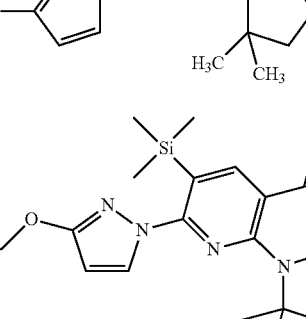 | +++ | +++ |
| (1-9) | 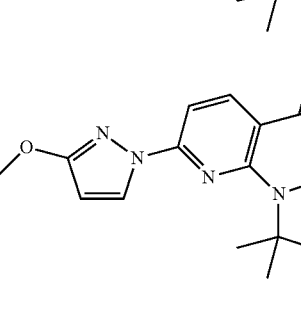 | ND | ND |
| (1-10) | 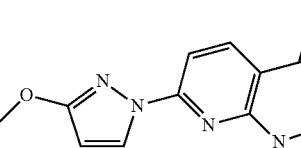 | ND | ND |
| (1-11) | 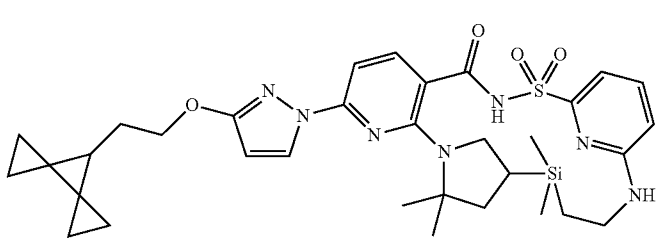 [SMILES: CC1(C)CC2CN1c1nc(-n3ccc(OCCC4C5(CC5)C45CC5)n3)ccc1C(=O)NS(=O)(=O)c1cccc(n1)NCC[Si]2(C)C] | ND | ND |

Other Embodiments

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A compound of Formula (1):

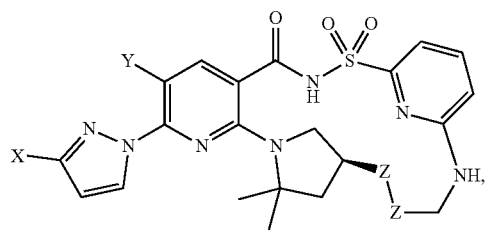

or a pharmaceutically acceptable salt or deuterated derivative thereof, wherein:

X is selected from $Si(R)_3$, $-(O)_n-(C_1-C_8$ alkyl), $-(O)_n-(C_3-C_{10}$ cycloalkyl), wherein:
 n is 0 or 1,
 each $C_1-C_8$ alkyl is substituted with 0, 1, 2, or 3 groups selected from halogen, hydroxy, oxo, $C_3-C_{10}$ cycloalkyl, $C_1-C_4$ haloalkyl, and $Si(R)_3$ groups,
 each $C_3-C_{10}$ cycloalkyl is substituted with 0, 1, 2, 3, or 4 groups selected from halogen, $C_1-C_4$ haloalkyl, $C_1-C_4$ alkyl, and $Si(R)_3$ groups, and one $-CH_2-$ in each $C_1-C_8$ alkyl is optionally replaced with $-Si(R)_2-$;

Y is selected from hydrogen and $-Si(R)_3$;

each Z is independently selected from $-CH_2-$ and $-Si(R)_2-$; and each R is independently selected from phenyl and $C_1-C_6$ alkyl groups; and wherein the compound of Formula (1) contains at least one Si atom.

2. The compound of claim 1, wherein X is selected from $Si(R)_3$,

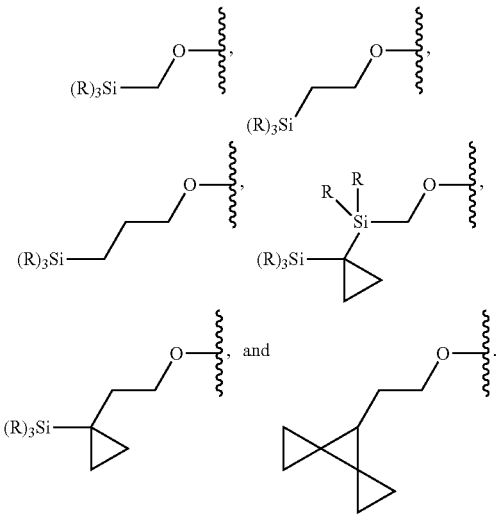

3. The compound of claim 1, wherein the compound is chosen from:

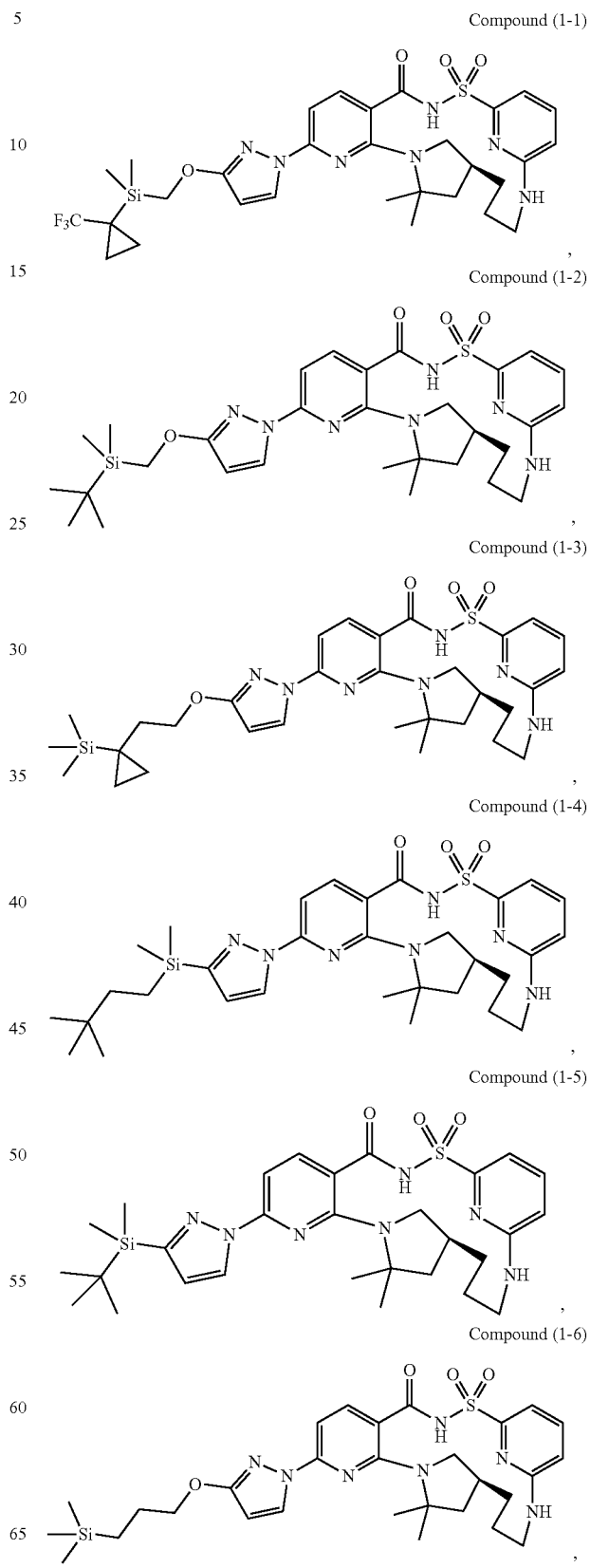

-continued

Compound (1-7)
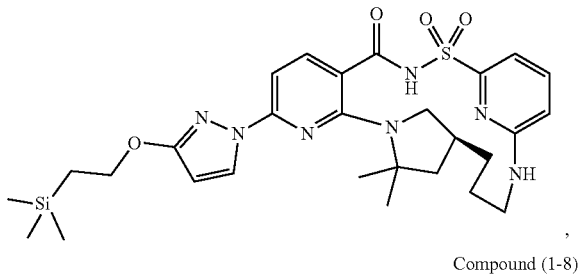

Compound (1-8)
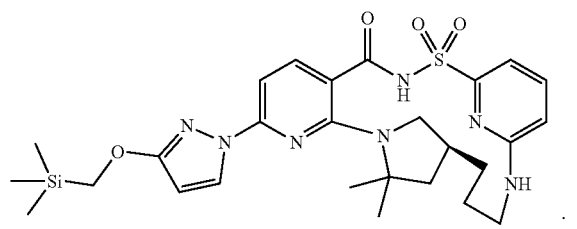

Compound (1-9)
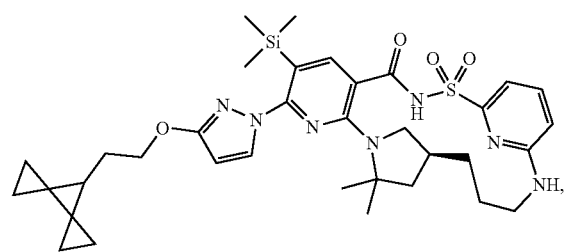

Compound (1-10)
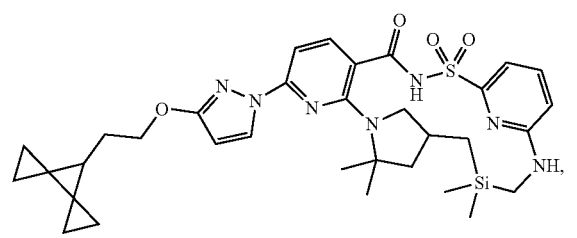

Compound (1-11)
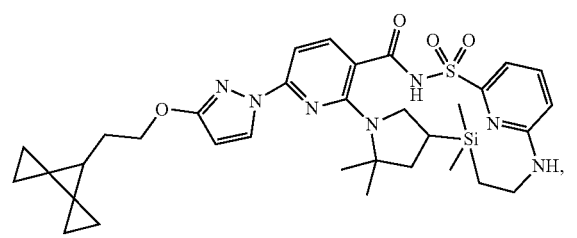

and pharmaceutically acceptable salts and deuterated derivatives thereof.

4. The compound of claim 1, wherein at least one hydrogen is replaced by deuterium.

5. The compound of claim 1, wherein the compound is a pharmaceutically acceptable salt.

6. A compound of Formula (2):

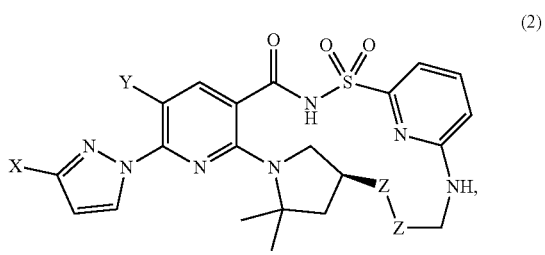

(2)

or a pharmaceutically acceptable salt or deuterated derivative thereof, wherein:

X is selected from Ge(R)$_3$, —(O)$_n$—(C$_1$-C$_8$ alkyl), —(O)$_n$—(C$_3$-C$_{10}$ cycloalkyl), wherein:
 n is 0 or 1,
 each C$_1$-C$_8$ alkyl is substituted with 0, 1, 2, or 3 groups selected from halogen, hydroxy, oxo, C$_3$-C$_{10}$ cycloalkyl, C$_1$-C$_4$ haloalkyl, and Ge(R)$_3$ groups,
 each C$_3$-C$_{10}$ cycloalkyl is substituted with 0, 1, 2, 3, or 4 groups selected from halogen, C$_1$-C$_4$ haloalkyl, C$_1$-C$_4$ alkyl, and Ge(R)$_3$ groups, and one —CH$_2$— in each C$_1$-C$_8$ alkyl is optionally replaced with —Ge(R)$_2$—;

Y is selected from hydrogen and —Ge(R)$_3$;

each Z is independently selected from —CH$_2$— and —Ge(R)$_2$—; and each R is independently selected from phenyl and C$_1$-C$_6$ alkyl groups; and wherein the compound of Formula (2) contains at least one Ge atom.

7. The compound of claim 6, wherein X is selected from Ge(R)$_3$,

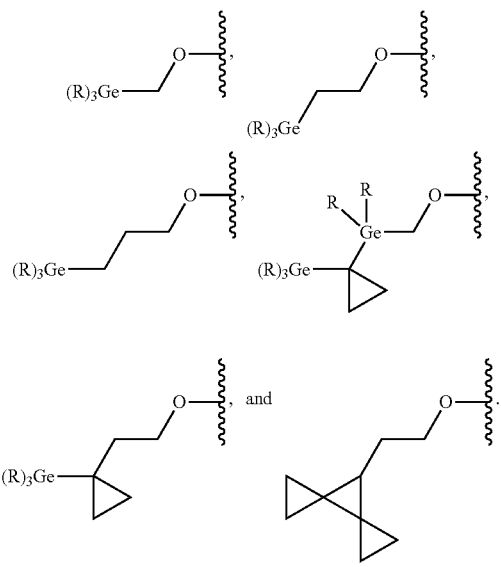

8. The compound of claim 6, wherein the compound is chosen from:

Compound (2-1)

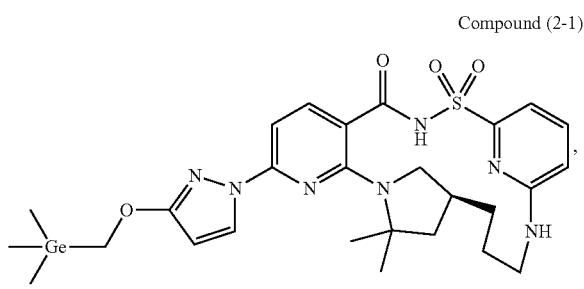

and pharmaceutically acceptable salts and deuterated derivatives thereof.

9. The compound of claim 6, wherein at least one hydrogen is replaced by deuterium.

10. The compound of claim 6, wherein the compound is a pharmaceutically acceptable salt.

11. A compound of Formula (3):

(3)

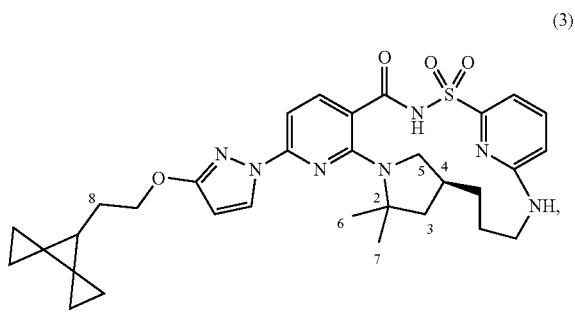 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

or a pharmaceutically acceptable salt or deuterated derivative thereof, wherein:

the carbon atom at position 2 of Formula (3) is replaced by a silicon atom;

at least one of the methyl groups at positions 6 and 7 of Formula (3) is replaced by a group chosen from —Si(R)$_3$ groups, —Si(R)$_2$(OR) groups, and —Si(R)(OR)$_2$ groups;

at least one of the methylene groups at positions 3, 5, and 8 of Formula (3) is replaced by a group chosen from >Si(R)$_2$ groups and >Si(R)(OR) groups; and/or the methine group at position 4 of Formula (3) is replaced by a group chosen from ≡Si(R) groups and ≡Si(OR) groups; and wherein each R is independently chosen from hydrogen, phenyl, and C$_1$-C$_6$ alkyl groups.

12. The compound of claim 11, wherein at least one hydrogen is replaced by deuterium.

13. The compound of claim 11, wherein the compound is a pharmaceutically acceptable salt.

14. A compound of Formula (4):

(4)

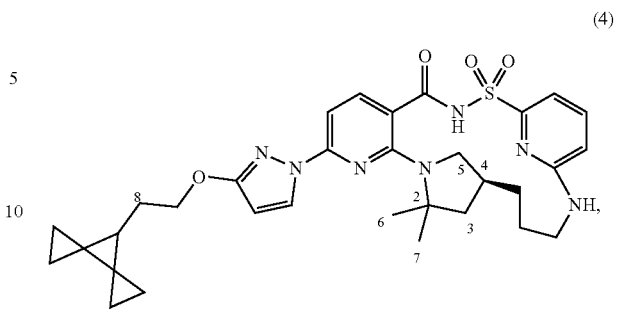

or a pharmaceutically acceptable salt or deuterated derivative thereof, wherein:

the carbon atom at position 2 of Formula (4) is replaced by a germanium atom;

at least one of the methyl groups at positions 6 and 7 of Formula (4) is replaced by a group chosen from —Ge(R)$_3$ groups, —Ge(R)$_2$(OR) groups, and —Ge(R)(OR)$_2$ groups;

at least one of the methylene groups at positions 3, 5, and 8 of Formula (4) is replaced by a group chosen from >Ge(R)$_2$ groups and >Ge(R)(OR) groups; and/or the methine group at position 4 of Formula (4) is replaced by a group chosen from ≡Ge(R) groups and ≡Ge(OR) groups; and wherein each R is independently chosen from hydrogen, phenyl, and C$_1$-C$_6$ alkyl groups.

15. The compound of claim 14, wherein at least one hydrogen is replaced by deuterium.

16. The compound of claim 14, wherein the compound is a pharmaceutically acceptable salt.

17. A pharmaceutical composition comprising a compound of claim 1 and a pharmaceutically acceptable carrier.

18. The pharmaceutical composition of claim 17, further comprising one or more additional therapeutic agent(s).

19. The pharmaceutical composition of claim 18, wherein the one or more additional therapeutic agent(s) comprise(s) a compound selected from:

Compound II

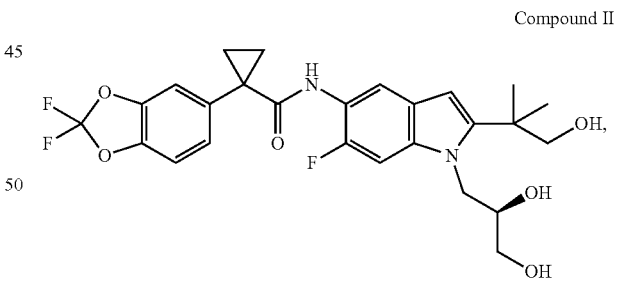

(a)

Compound III

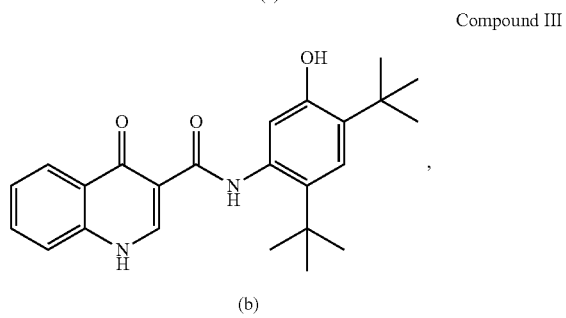

(b)

-continued

Compound III-d

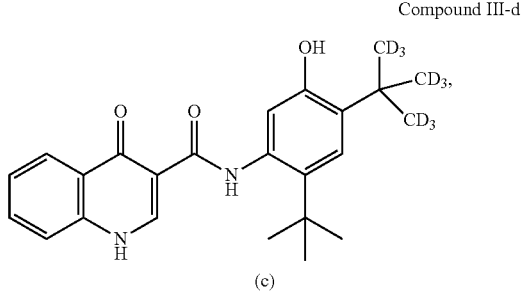

(c)

and (d) pharmaceutically acceptable salts thereof.

20. The pharmaceutical composition of claim 19, wherein the composition comprises Compound II and Compound III.

21. The pharmaceutical composition of claim 19, wherein the composition comprises Compound II and Compound III-d.

22. A pharmaceutical composition comprising:
(a) at least one compound chosen from compounds of claim 1;
(b) at least one pharmaceutically acceptable carrier; and optionally one or more of:
(c) (i) a compound chosen from Compound II:

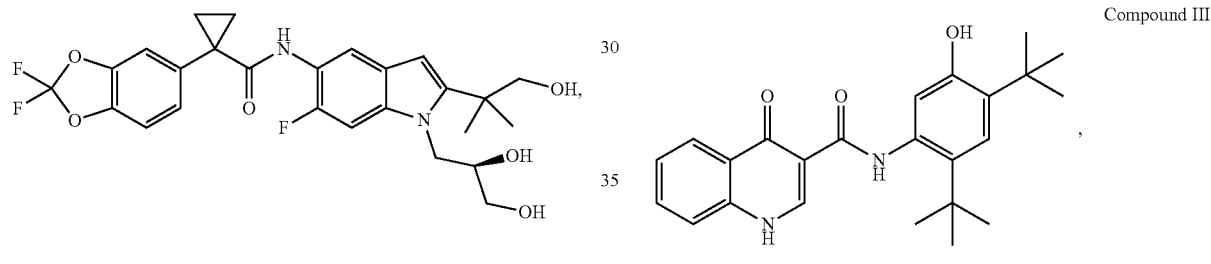

and pharmaceutically acceptable salts and deuterated derivatives thereof; and
(ii) a compound chosen from Compound III, Compound III-d:

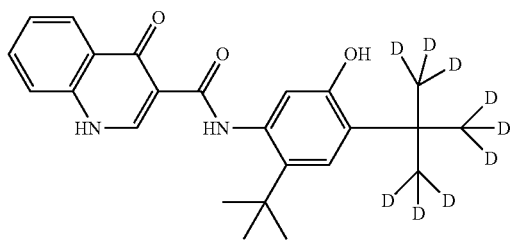

III

III-d and pharmaceutically acceptable salts and deuterated derivatives thereof.

23. A method of treating cystic fibrosis comprising administering to a patient in need thereof a compound of claim 1.

24. The method of claim 23, further comprising administering to the patient one or more additional therapeutic agent(s) prior to, concurrent with, or subsequent to the compound.

25. The method of claim 24, wherein the one or more additional therapeutic agent(s) comprise(s) a compound selected from:

Compound II

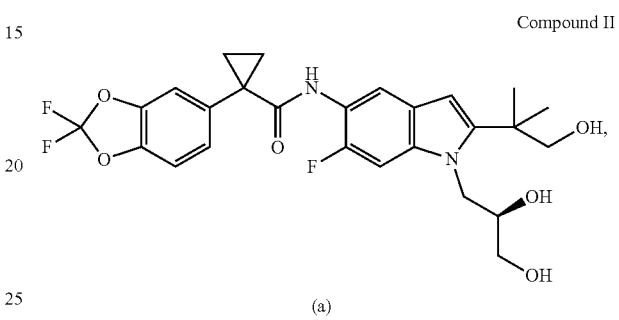

(a)

Compound III (b)

Compound III-d

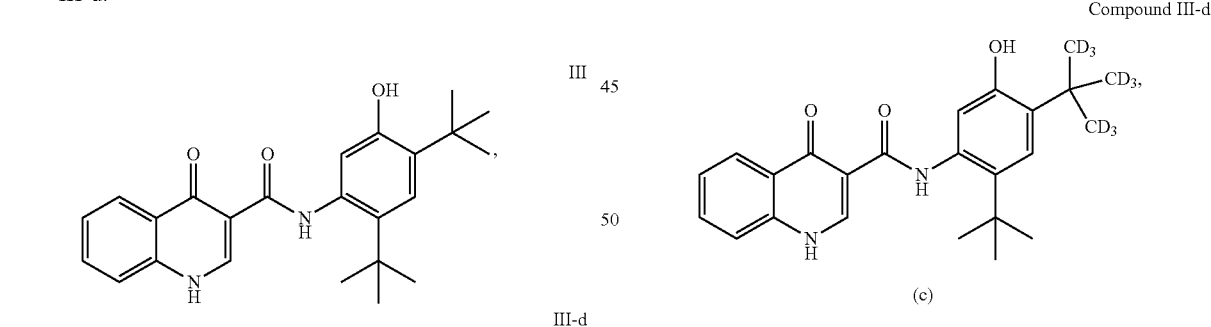

(c)

and (d) pharmaceutically acceptable salts thereof.

26. The method of claim 25, wherein the one or more additional therapeutic agent(s) comprise(s) Compound II and Compound III.

27. The method of claim 25, wherein the one or more additional therapeutic agent(s) comprise(s) Compound II and Compound III-d.

* * * * *